US007777008B2

(12) United States Patent
Ponath et al.

(10) Patent No.: US 7,777,008 B2
(45) Date of Patent: Aug. 17, 2010

(54) ILT3 BINDING MOLECULES AND USES THEREFOR

(75) Inventors: Paul Ponath, San Francisco, CA (US);
Michael Rosenzweig, Boston, MA (US);
Jose F. Ponte, South Boston, MA (US)

(73) Assignee: Tolerx, Inc., Cambridge, MA (US)

( * ) Notice: Subject to any disclaimer, the term of this patent is extended or adjusted under 35 U.S.C. 154(b) by 59 days.

(21) Appl. No.: 11/820,363

(22) Filed: Jun. 19, 2007

(65) Prior Publication Data
US 2008/0038260 A1 Feb. 14, 2008

Related U.S. Application Data

(60) Provisional application No. 60/814,931, filed on Jun. 19, 2006.

(51) Int. Cl.
*C07K 16/00* (2006.01)
*C12P 21/08* (2006.01)
*A61K 39/395* (2006.01)
*A61K 39/00* (2006.01)

(52) U.S. Cl. .............. 530/387.1; 530/387.3; 530/388.1; 424/130.1; 424/133.1; 424/141.1

(58) Field of Classification Search .................. None
See application file for complete search history.

(56) References Cited

U.S. PATENT DOCUMENTS

| | | | |
|---|---|---|---|
| 4,399,216 A | 8/1983 | Axel et al. |
| 4,444,878 A | 4/1984 | Paulus |
| 4,510,245 A | 4/1985 | Cousens et al. |
| 4,522,811 A | 6/1985 | Eppstein et al. |
| 4,634,665 A | 1/1987 | Axel et al. |
| 4,704,362 A | 11/1987 | Itakura et al. |
| 4,741,900 A | 5/1988 | Alvarez et al. |
| 4,745,055 A | 5/1988 | Schenk et al. |
| 4,816,397 A | 3/1989 | Boss et al. |
| 4,816,567 A | 3/1989 | Cabilly et al. |
| 4,968,615 A | 11/1990 | Koszinowski et al. |
| 5,168,062 A | 12/1992 | Stinski |
| 5,179,017 A | 1/1993 | Axel et al. |
| 5,225,539 A | 7/1993 | Winter |
| 5,304,489 A | 4/1994 | Rosen |
| 5,530,101 A | 6/1996 | Queen et al. |
| 5,585,089 A | 12/1996 | Queen et al. |
| 5,585,097 A | 12/1996 | Bolt et al. |
| 5,589,369 A | 12/1996 | Seidman et al. |
| 5,591,669 A | 1/1997 | Krimpenfort et al. |
| 5,658,570 A | 8/1997 | Newman et al. |
| 5,693,761 A | 12/1997 | Queen et al. |
| 5,693,762 A | 12/1997 | Queen et al. |
| 5,693,780 A | 12/1997 | Newman et al. |
| 5,741,957 A | 4/1998 | Deboer et al. |
| 5,756,096 A | 5/1998 | Newman et al. |
| 5,811,524 A | 9/1998 | Brams et al. |
| 5,837,821 A | 11/1998 | Wu |
| 5,849,992 A | 12/1998 | Meade et al. |
| 5,939,598 A | 8/1999 | Kucherlapati et al. |
| 5,959,083 A | 9/1999 | Bosslet et al. |
| 5,969,108 A | 10/1999 | McCafferty et al. |
| 6,075,181 A | 6/2000 | Kucherlapati et al. |
| 6,180,370 B1 | 1/2001 | Queen et al. |
| 6,384,203 B1 | 5/2002 | Anderson et al. |
| 6,448,035 B1 | 9/2002 | Cosman |
| 6,476,198 B1 | 11/2002 | Kang |
| 6,667,175 B1 | 12/2003 | Sucis-Foca et al. |
| 6,759,239 B2 | 7/2004 | Sucis-Foca et al. |
| 6,821,724 B1 | 11/2004 | Mittman et al. |
| 7,014,853 B2 | 3/2006 | Cosman |
| 7,144,728 B1 | 12/2006 | Sucis-Foca et al. |
| 7,285,631 B2 | 10/2007 | Bejanin et al. |
| 2002/0103345 A1 | 8/2002 | Zhu |
| 2002/0132983 A1 | 9/2002 | Junghans |
| 2003/0027358 A1 | 2/2003 | Cosman et al. |
| 2003/0060614 A1 | 3/2003 | Cosman et al. |
| 2003/0165875 A1 | 9/2003 | Colonna et al. |
| 2003/0166073 A1 | 9/2003 | Cosman |
| 2003/0198637 A1 | 10/2003 | Zhou et al. |
| 2004/0138126 A1 | 7/2004 | Cosman |
| 2004/0241167 A1 | 12/2004 | Suciu-Foca et al. |
| 2004/0253674 A1 | 12/2004 | Cosman |
| 2005/0214205 A1 | 9/2005 | Salcedo et al. |
| 2006/0078564 A1 | 4/2006 | Cosman |
| 2007/0041982 A1 | 2/2007 | Ponath et al. |

FOREIGN PATENT DOCUMENTS

EP          68763 B1          4/1987

(Continued)

OTHER PUBLICATIONS

Mac Callum, Martin, and Thornton. Antibody-antigen interactions: contact analysis and binding site topography. Journal of Molecular Biology, 1996. vol. 292, pp. 732-745.*

(Continued)

*Primary Examiner*—Larry R. Helms
*Assistant Examiner*—Anne M. Gussow
(74) *Attorney, Agent, or Firm*—Fish & Richardson P.C.

(57) ABSTRACT

The present invention provides binding molecules that specifically bind to ILT3, e.g., human ILT3 (hILT3), on antigen presenting cells, such as for example, monocytes, macrophages and dendritic cells (DC), e.g., monocyte-derived dendritic cells (MDDC). The binding molecules of the invention are characterized by binding to hILT3 with high affinity and downmodulating immune responses in vitro, e.g., downmodulating alloimmune responses; the production of inflammatory cytokines by dendritic cells, e.g., monocyte-derived dendritic cells (MDDC); the upregulation of costimulatory molecules by DC, e.g., MDDC; and/or calcium flux in monocytes. In addition, the binding molecules upregulate the expression of inhibitory receptors on dendritic cells, e.g., immature dendritic cells. Surprisingly, these same binding molecules which downmodulate immune responses in vitro, are immunostimulatory in vivo. Various aspects of the invention relate to binding molecules, and pharmaceutical compositions thereof. Methods of using the binding molecules of the invention to detect human ILT3 or to modulate human ILT3 activity, either in vitro or in vivo, are also encompassed by the invention.

28 Claims, 6 Drawing Sheets

FOREIGN PATENT DOCUMENTS

| EP | 255694 A1 | 2/1988 |
|---|---|---|
| EP | 125023 B1 | 6/1991 |
| EP | 120694 B1 | 7/1993 |
| EP | 368684 B1 | 3/1994 |
| EP | 266663 B1 | 1/1995 |
| EP | 256654 B1 | 9/1996 |
| WO | WO1987002671 A1 | 5/1987 |
| WO | WO1988003559 A1 | 5/1988 |
| WO | WO1988003565 A1 | 5/1988 |
| WO | WO199007861 A1 | 7/1990 |
| WO | WO1992022653 A1 | 12/1992 |
| WO | WO1994009817 A1 | 5/1994 |
| WO | WO-94/12661 A1 | 6/1994 |
| WO | WO-94/13805 A1 | 6/1994 |
| WO | WO-96/06863 A1 | 3/1996 |
| WO | WO-98/33919 A2 | 8/1998 |
| WO | WO-98/40488 A1 | 9/1998 |
| WO | WO2000006605 A2 | 2/2000 |
| WO | WO-01/83560 A1 | 11/2001 |
| WO | WO2002002781 A1 | 1/2002 |
| WO | WO-03/038043 A2 | 5/2003 |
| WO | WO-03/041650 A2 | 5/2003 |
| WO | WO-03/048321 A2 | 6/2003 |
| WO | WO-03/075846 A2 | 9/2003 |
| WO | WO-03/075855 A2 | 9/2003 |
| WO | WO2003000199 A3 | 1/2004 |
| WO | WO-2006/025060 A2 | 3/2006 |
| WO | WO-2006/033811 A2 | 3/2006 |
| WO | WO 2006033811 A2 * | 3/2006 |
| WO | WO 2007/089945 | 8/2007 |

OTHER PUBLICATIONS

De Pascalis, Iwahashi, Tamura, Padlan, Gonzales, Santos, Giuliano, Schuck, Scholm, and Kashmiri. Grafting of abbreviated complementary determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen binding site of an anti-ErbB2 antibody obtained by shotgun scanning mutagenesis. Journal of Molecular Biology, 2002. vol. 320, pp. 415-428.*
Wu, Nie, Huse, and Watkins. Humanization of a murine monoclonal antibody by simultaneous optimization of framework and CDR residues. Journal of Molecular Biology, 1999. vol. 294, pp. 151-162.*
Casset, Florence et al., "A peptide mimetic of an anti-CD4 monoclonal antibody by rational design," *Biochemical and Biophysical Research Communications*, vol. 307:198-205 (2003).
Chen, Yvonne et al., "Selection and Analysis of an Optimized Anti-VEGF Antibody: Crystal Structure of an Affinity-matured Fab in Complex with Antigen," *J. Mol. Biol.*, vol. 293:865-881 (1999).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," *The Journal of Immunology*, vol. 169:3076-3084 (2002).
Holm, Patrik et al., "Functional mapping and single chain construction of the anti-cytokeratin 8 monoclonal antibody TS1," *Molecular Immunology*, vol. 44:1075-1084 (2007).
MacCallum, Robert M. et al., "Antibody-antigen Interactions: Contact Analysis and Binding Site Topography," *J. Mol. Biol.*, vol. 262:732-745 (1996).
Rudikoff, Stuart et al., "Single amino acid substitution altering antigen-binding specificity," *Proc. Natl. Acad. Sci. USA*, vol. 79:1979-1983 (1982).
Vajdos, Felix F. et al., "Comprehensive Functional Maps of the Antigen-binding Site of an Anti-ErbB2 Antibody Obtained with Shotgun Scanning Mutagenesis," *J. Mol. Biol.*, vol. 320:415-428 (2002).
Wallet, Mark A. et al., "Immunoregulation of Dendritic Cells," *Clinical Medicine & Research*, vol. 3(3):166-175 (2005).
Wu, Herren et al., "Humanization of a Murine Monoclonal Antibody by Simultaneous Optimization of Framework and CDR Residues," *J. Mol. Biol.*, vol. 294:151-162 (1999).
International Search Report and Written Opinion for Application No. PCT/US06/24141, dated Oct. 18, 2007.
International Search Report and Written Opinion for Application No. PCT/US07/14239, dated Mar. 12, 2009.
Cella, Marina et al., "A Novel Inhibitory Receptor (ILT3) Expressed in Monocytes, Macrophages, and Dendritic Cells Involved in Antigen Processing," *J. Exp. Med.*, vol. 185(10):1743-1751 (1997).
Abass et al. (eds.), "Lymphocyte Specificity and Activation," *Cellular and Molecular Immunology*, 1991, W.B. Saunders, Philadelphia, PA, p. 54.
Boyer et al., "Relative Cytotoxic Activity of Immunotoxins Reactive with Different Epitopes on the Extracellular Domain of the c-*erb*B-2 (HER-2/*neu*) Gene Product p. 185," *Int. J. Cancer*, 1999, 82:525-531.
Bryceson et al., "The rat orthologue to the inhibitory receptor gp49B is expressed by neutrophils and monocytes, but not by NK cells or mast cells," *Eur. J. Immunol.*, 2005, 35(4):1230-1239.
Caldas et al., "Humanization of the anti-CD18 antibody 6.7: an unexpected effect of a framework residue in binding to antigen," *Mol. Immunol.*, 2003, 39(15):941-952.
Castells et al., "Cloning of the gp49B Gene of the Immunoglobulin Superfamily and Demonstration That One of Its Two Products Is an Early-expressed Mast Cell Surface Protein Originally Described as gp49," *J. Biol. Chem.*, 1994, 269(11):8393-8401.
Chien et al., "Significant structural and functional change of an antigen-binding site by a distant amino acid substitution: Proposal of a structural mechanism,"*Proc. Natl. Acad. Sci. USA*, 1989, 86(14):5532-5536.
Giusti et al., "Somatic diversification of S107 from an antiphosphocholine to an anti-DNA autoantibody is due to a single base change in its heavy chain variable region," *Proc. Natl. Acad. Sci. USA*, 1987, 84(9):2926-2930.
Güssow and Seemann, "Humanization of Monoclonal Antibodies," *Meth. Enzymol.*, 1991, 203:99-121.
Heinzmann et al., "Common polymorphisms and alternative splicing in the ILT3 gene are not associated with atopy," *Eur. J. Immunogenetics*, 2000, 27:121-127.
Jiang et al., "A Novel Peptide Isolated from a Phage Display Peptide Library with Trastuzumab Can Mimic Antigen Epitope of HER-2," *J. Biol. Chem.*, 2005, 280(6):4656-4662.
Katz et al., "Mouse mast cell gp41B1 contains two immunoreceptor tyrosine-based inhibition motifs and suppresses mast cell activation when colligated with the high-affinity Fc receptor for IgE," *Proc. Natl. Acad. Sci. USA*, 1996, 93:10809-10814.
Mariuzza et al., "The Structural Basis of Antigen-Antibody Recognition," *Annu. Rev. Biophys. Chem.*, 1987, 16:139-159.
Nunez and Filgueira, "Flow cytometric assessment of the reactivity of a panel of monoclonal antibodies (mAb) against two populations of human dendritic cells (DC)," *BMC Immunol.*, 2001, 2:1-7.
Penna et al., "Expression of the inhibitory receptor ILT3 on dendritic cells is dispensable for induction of $CD4^+Foxp3^+$ regulatory T cells by 1,25-dihydroxyvitamin $D_3$," *Blood*, 2005, 106:3490-3497.
Pettersen et al., "CD47 Signals T Cell Death," *J. Immunol.*, 1999, 162(12):7031-7040.
Riemer et al., "Matching of trastuzumab (Herceptin®) epitope mimics onto the surface of Her-2/neu—a new method of epitope definition," *Mol. Immunol.*, 2005, 42:1121-1124.
Stancovski et al., "Mechanistic aspects of the opposing effects of monoclonal antibodies to the ERBB2 receptor on tumor growth," *Proc. Natl. Acad. Sci. USA*, 1991, 88:8691-8695.
Suciu-Foca et al., "Soluble Ig-Like Transcript 3 Inhibits Tumor Allograft Rejection in Humanized SCID Mice and T Cell Responses in Cancer Patients," *J. Immunol.*, 2007, 178:7432-7441.
Wang et al., "Inducible Expression of the gp49B Inhibitory Receptor on NK Cells," *J. Immunol.*, 2000, 164(10):5215-5220.

International Preliminary Report on Patentability for Application No. PCT/US2006/024141, dated Dec. 17, 2007.
International Preliminary Report on Patentability for Application No. PCT/US2007/14239 mailed Apr. 9, 2009, 8 pages.
Restriction Requirement, U.S. Appl. No. 11/471,397 mailed Mar. 12, 2007, 10 pages.
Lahive & Cockfield, Response to Restriction Requirement, U.S. Appl. No. 11/471,397 mailed Sep. 12, 2007, 6 pages.
Office Action, U.S. Appl. No. 11/471,397 mailed Dec. 3, 2007, 12 pages.
Lahive & Cockfield, Response to Non-Final Office Action, U.S. Appl. No. 11/471,397 mailed Jun. 3, 2008, 19 pages.
Office Action, U.S. Appl. No. 11/471,397 mailed May 29, 2009, 36 pages.
Adelman et al., "In Vitro Deletional Mutagenesis for Bacterial Production of the 20,000-Dalton Form of Human Pituitary Growth Hormone," DNA, 1983, 2(3):183-193.
Amit et al., "Three-dimensional structure of an antigen-antibody complex at 2.8 A resolution," Science, 1986, 233:747-753.
Arthur and Mason, "T cells that help B cell responses to soluble antigen are distinguishable from those producing interleukin 2 on mitogenic or allogeneic stimulation," J Exp Med, 1986, 163(4):774-786.
Bird et al., "Single-Chain Antigen-Binding Proteins," Science, 1988, 242:423-426.
Boder et al., "Directed evolution of antibody fragments with monovalent femtomolar antigen-binding affinity," Proc Natl Acad Sci USA, 2000, 97(20):10701-10705.
Byrn et al., "Biological properties of a CD4 immunoadhesin," Nature, 1990, 344:667-670.
Chamow and Ashkenazi, "Immunoadhesins: principles and applications," Trends Biotechnol, 1996, 14(2):52-60.
Chang et al., "Tolerization of dendritic cells by Ts cells: the crucial role of inhibitory receptors ILT3 and ILT4," Nat Immunol, 2002, 3(3):237-243.
Cheung et al., "Epitope-specific antibody response to the surface antigen of duck hepatitis B virus in infected ducks," Virology, 1990, 176:546-552.
Chothia and Lesk, "Canonical structures for the hypervariable regions of immunoglobulins," J Mol Biol, 1987, 196:901-917.
Clackson et al., "Making antibody fragments using phage display libraries," Nature 1991, 352:624-628.
Co et al., "Chimeric and humanized antibodies with specificity for the CD33 antigen," J Immunol, 1992, 148 (4):1149-1154.
Connolly, "Analytical Molecular Surface Calculation," J Appl Cryst, 1983, 16:548-558.
Daugherty et al., "Flow cytometric screening of cell-based libraries," J Immunol Meth, 2000, 243:211-227.
Falkner and Zachau, "Expression of mouse immunoglobulin genes in monkey cells," Nature, 1982, 298:286-288.
Finkelman et al., "Il-4 is required to generate and sustain in vivo IgE responses," J Immunol, 1988, 141(7):2335-2341.
Hanes et al., "Picomolar affinity antibodies from a fully synthetic naïve library selected and evolved by ribosome display," Nat Biotechnol, 2000, 18(12):1287-1292.
Ho et al., "Site-directed mutagenesis by overlap extension using the polymerase chain reaction," Gene, 1989, 77:51-59.
Hoogenboom and Chames, "Natural and designer binding sites made by phage display technology," Immunol Today, 2000, 21:371-378.
Huie et al., "Antibodies to human fetal erythroid cells from a nonimmune phage antibody library," Proc Natl Acad Sci USA, 2001, 98(5):2682-2687.
Huston et al., "Protein engineering of antibody binding sites: recovery of specific activity in an anti-digoxin single-chain Fv analogue produced in Escherichia coli," Proc Natl Acad Sci USA, 1988, 85(16):5879-5883.
Hwang et al., "Use of human germline genes in a Cdr homology-based approach to antibody humanization," Methods, 2005, 36:35-42.
Irving et al., "Ribosome display and affinity maturation: from antibodies to single V-domains and steps towards cancer therapeutics," J Immunol Meth, 2001, 248:31-45.
Jendreyko et al., "Intradiabodies, bispecific, tetravalent antibodies for the simultaneous functional knockout of two cell surface receptors," J Biol Chem, 2003, 278(48):47812-47819.
Jones et al., "Replacing the complementarity-determining regions in a human antibody with those from a mouse," Nature, 1986, 321:522-525.
Kabat et al., "Unusual distributions of amino acids in complementarity-determining (hypervariable) segments of heavy and light chains of immunoglobulins and their possible roles in specificity of antibody-combining sites," J Biol Chem, 1977, 252(19):6609-6616.
Kaufman and Sharp, "Amplification and expression of sequences cotransfected with a modular dihydrofolate reductase complementary dna gene," J Mol Biol, 1982, 159(4):601-621.
Kettleborough et al., "Humanization of a mouse monoclonal antibody by CDR-grafting: the importance of framework residues on loop conformation," Protein Eng, 1991, 4(7):773-783.
Kirkland et al., "Analysis of the fine specificity and cross-reactivity of monoclonal anti-lipid A antibodies," J Immunol, 1986, 137(11):3614-3619.
Köhler and Milstein, "Continuous cultures of fused cells secreting antibody of a predefined specificity," Nature, 1975, 256:495-497.
Kolbinger et al., "Humanization of a mouse anti-human IgE antibody: a potential therapeutic for IgE-mediated allergies," Protein Eng, 1993, 6(8):971-980.
Lee and Richards, "The interpretation of protein structures: estimation of static accessibility," J Mol Biol, 1971, 55 (3):379-400.
Lui et al., J Mol Biol, 2002, 316:1063.
Marks et al., "By-passing Immunization. Human Antibodies from Vmart-gene Libraries Displayed on Phage," J Mol Biol, 1991, 222:581-597.
Marks et al., "By-passing immunization: building high affinity human antibodies by chain shuffling," Biotechnology, 1992, 10(7):779-783.
Martin and Thornton, "Structural families in loops of homologous proteins: automatic classification, modeling and application to antibodies," J Mol Biol, 1996, 263(5):800-815.
Milenic et al., "Construction, binding properties, metabolism, and tumor targeting of a single-chain Fv derived from the pancarcinoma monoclonal antibody CC49," Cancer Res, 1991, 51:6363-6371.
Moldenhauer et al., "Identity of Hml-1 antigen on intestinal intraepithelial T cells and of B-Iy7 antigen on hairy cell leukaemia," Scand J Immunol, 1990, 32(2):77-82.
Morel et al., "Monoclonal antibodies to bovine serum albumin: affinity and specificity determinations," Mol Immunol, 1988, 25:7-15.
Morrison et al., "Chimeric human antibody molecules: mouse antigen-binding domains with human constant region domains," Proc Natl Acad Sci USA, 1984, 81(21):6851-6855.
Morrison and Oi, "Transfer and expression of immunoglobulin genes," Annu Rev Immunol, 1984, 2:239-256.
Morrison, "Transfectomas Provide Novel Chimeric Antibodies," Science, 1985, 229:1202-1207.
Mosmann and Coffman, "TH1 and TH2 cells: different patterns of lymphokine secretion lead to different functional properties," Annu Rev Immunol, 1989, 7:145-173.
Nagy et al., "Fully human, HLA-DR-specific monoclonal antibodies efficiently induce programmed death of malignant lymphoid cells," Nat Med, 2002, 8:801-805.
Newman et al., ""Primatization" of recombinant antibodies for immunotherapy of human diseases: a macaque/human Chimeric antibody against human CD4," Biotechnol, 1992, 10:1455-1460.
Novotny and Haber, "Structural invariants of antigen binding: comparison of immunoglobulin VL-VH and VL-VL domain dimers," Proc Natl Acad Sci USA, 1985, 82:4592-4596.
Orlandi et al., "Cloning immunoglobulin variable domains for expression by the polymerase chain reaction," Proc Natl Acad Sci USA, 1989, 86:3833-3837.
Paliard et al., "Simultaneous production of IL-2, IL-4, and IFN-gamma by activated human CD4+ and CD8+ T cell clones," J Immunol, 1988, 141(3):849-855.
Pantoliano et al., "Conformational stability, folding, and ligand-binding affinity of single-chain Fv immunoglobulin fragments expressed in Escherichia coli," Biochemistry, 1991, 30(42):10117-10125.

Paul and Seder, "Lymphocyte responses and cytokines," Cell, 1994, 76:241-251.

Portolano et al., "Lack of Promiscuity in Autoantigen-Specific H and L Chain Combinations as Revealed by Human H and L Chain "Roulette"," J Immunol, 1993, 150(3):880-887.

Presta, "Antibody Engineering," Curr Op Struct Biol, 1992, 3(4):394-398.

Queen et al., "A humanized antibody that binds to the interleukin 2 receptor," Proc Natl Acad Sci USA, 1989, 86 (24):10029-10033.

Queen et al., "Cell-type specific regulation of a kappa immunoglobulin gene by promoter and enhancer elements," Immunol Rev, 1986, 89:49-68.

Rabin et al., "Chemokine receptor responses on T cells are achieved through regulation of both receptor expression and signaling," J Immunol, 1999, 162(7):3840-3850.

Riechmann et al., "Reshaping human antibodies for therapy," Nature, 1988, 332:323-327.

Santiago-Schwarz, "Dendritic cells: friend or foe in autoimmunity?" Rheum Dis Clin North Am, 2004, 30:115-134.

Stahli et al., "Distinction of epitopes by monoclonal antibodies," Meth Enzymol, 1983, 92:242-253.

Strejan et al., "Suppression of chronic-relapsing experimental allergic encephalomyelitis in strain-13 guinea pigs by administration of liposome-associated myelin basic protein," J Neuroimmunol, 1984, 7:27-41.

Takkinen et al., "An active single-chain antibody containing a cellulase linker domain is secreted by Escherichia coli," Protein Eng, 1991, 4(7):837-841.

Taylor et al., "A transgenic mouse that expresses a diversity of human sequence heavy and light chain immunoglobulins," Nucl Acids Res., 1992, 20(23):6287-6295.

Tramontano et al., "Framework residue 71 is a major determinant of the position and conformation of the second hypervariable region in the VH domains of immunoglobulins," J Mol Biol, 1990, 215:175-182.

Urlaub and Chasin, "Isolation of Chinese hamster cell mutants deficient in dihydrofolate reductase activity," Proc Natl Acad Sci USA, 1980, 77(7):4216-4220.

Verhoeyen et al., "Reshaping Human Antibodies: Grafting an Antilysozyme Activity," Science, 1988, 239:1534-1536.

Waldmann and Cobbold, "Regulating the immune response to transplants. A role for CD4+ regulatory cells?" Immunity, 2001, 14(4):399-406.

Wilson et al., "The use of mRNA display to select high-affinity protein-binding pep," Proc Natl Acad Sci USA, 2001, 98 (7):3750-3755.

Yang et al., "Identification of the Ebola virus glycoprotein as the main viral determinant of vascular cell cytotoxicity and injury," Nat Med, 2000, 6(8):886-889.

Youn et al., "Molecular cloning of leukotactin-1: a novel human beta-chemokine, a chemoattractant for neutrophils, monocytes, and lymphocytes, and a potent agonist at CC chemokine receptors 1 and 3," J Immunol, 1997, 159 (11):5201-5205.

Youn et al., "Characterization of CKbeta8 and CKbeta8-1: two alternatively spliced forms of human beta-chemokine, chemoattractants for neutrophils, monocytes, and lymphocytes, and potent agonists at CC chemokine receptor 1," Blood, 1998, 91(9):3118-3126.

Supplementary European Search Report in EP 06 78 5268 mailed Dec. 14, 2009, 7 pages.

* cited by examiner

ILT3 BINDING MOLECULES AND USES THEREFOR

RELATED APPLICATIONS

This application claims the benefit of priority to U.S. Provisional Application, U.S. Ser. No. 60/814,931, filed on Jun. 19, 2006, titled "ILT3 BINDING MOLECULES AND USES THEREFOR". The entire contents of this application are hereby incorporated by reference.

BACKGROUND OF THE INVENTION

Immunoglobulin-like transcript (ILT) 3 is a cell surface molecule that is a member of the immunoglobulin superfamily. ILT3 is selectively expressed by myeloid antigen presenting cells (APCs) such as monocytes, macrophages, and dendritic cells (DC). The cytoplasmic region of ILT3 contains putative immunoreceptor tyrosine-based inhibitory motifs (ITIMs). Co-ligation of ILT3 to stimulatory receptors expressed by APCs results in a blunting of the increased [Ca2+] flux and tyrosine phosphorylation triggered by these receptors. Signal extinction involves SH2-containing protein tyrosine phosphatase 1, which is recruited by ILT3 upon cross-linking. ILT3 can also function in antigen capture and presentation. It is efficiently internalized upon cross-linking and delivers its ligand to an intracellular compartment where it is processed and presented to T cells (Cella, et al. (1997) *J. Exp. Med.* 185:1743-1751).

Thus, ILT3 is an inhibitory receptor that can negatively regulate activation of APCs and can be used by APCs for antigen uptake. The development of agents useful in modulating signaling via ILT3 would be of great benefit in modulating immune responses.

SUMMARY OF THE INVENTION

The present invention provides binding molecules that specifically bind to ILT3, e.g., human ILT3 (hILT3), on cells, such as antigen presenting cells, e.g., monocytes, macrophages and dendritic cells, e.g., monocyte-derived dendritic cells. The binding molecules of the invention are characterized by binding to hILT3 with high affinity and downmodulating immune cell activation in vitro, e.g., downmodulating alloimmune responses; the production of inflammatory cytokines by dendritic cells, e.g., monocyte-derived dendritic cells (MDDC); the upregulation of costimulatory molecules by DC, e.g., MDDC; and/or calcium flux in monocytes. In addition, the binding molecules upregulate the expression of inhibitory receptors on dendritic cells, e.g., immature dendritic cells. Surprisingly, these same binding molecules which downmodulate immune cell activation in vitro, are immunostimulatory in vivo, e.g., upmodulate immune responses.

Accordingly, one aspect of the invention features a binding molecule comprising the amino acid sequence of SEQ ID NO: 1.

In another aspect, the invention features a binding molecule comprising the amino acid sequence of SEQ ID NO:2.

Yet another aspect of the invention features a binding molecule comprising at least one complementarity determining region (CDR) amino acid sequence selected from the group consisting of: SEQ ID NO:3, SEQ ID NO:4, and SEQ ID NO:5. In one embodiment, the binding molecule comprises at least two complementarity determining region (CDR) amino acid sequences selected from the group consisting of: SEQ ID NO:3, SEQ ID NO:4, and SEQ ID NO:5. In another embodiment, the binding molecule comprises at least three complementarity determining region (CDR) amino acid sequences selected from the group consisting of: SEQ ID NO:3, SEQ ID NO:4, and SEQ ID NO:5.

Another aspect of the invention features a binding molecule comprising at least one complementarity determining region (CDR) amino acid sequence selected from the group consisting of: SEQ ID NO:6, SEQ ID NO:7, and SEQ ID NO:8. In one embodiment, the binding molecule comprises at least two complementarity determining region (CDR) amino acid sequences selected from the group consisting of: SEQ ID NO:6, SEQ ID NO:7, and SEQ ID NO:8. In another embodiment, the binding molecule comprises at least three complementarity determining region (CDR) amino acid sequences selected from the group consisting of: SEQ ID NO:6, SEQ ID NO:7, and SEQ ID NO:8.

Another aspect of the invention features a binding molecule comprising the CDRs shown in SEQ ID NOs: 3-8.

One aspect of the invention features a binding molecule comprising a heavy chain variable region comprising the amino acid sequence of SEQ ID NO: 1 and further comprising a light chain variable region comprising the amino acid sequence of SEQ ID NO:2.

Another aspect of the invention features a binding molecule that binds to ILT3 on human monocyte-derived dendritic cells (MDDC) and has a binding constant (Kd) of $0.9 \times 10^{-9}$ or less.

In one embodiment, the binding molecule downmodulates immune cell activation in vitro.

In another embodiment, the binding molecule upmodulates immune response in vivo.

In yet another embodiment, the constant region of the binding molecule comprises an IgG1 heavy chain constant region.

In one embodiment, the binding molecule binds to human ILT3 on dendritic cells

In another embodiment, the binding molecule binds to human ILT3 on monocytes.

In yet another embodiment, the binding molecule downmodulates the production of inflammatory cytokines by dendritic cells in vitro.

In one embodiment, the binding molecule downmodulates the upregulation of costimulatory molecules on dendritic cells in vitro.

In another embodiment, the binding molecule upmodulates the expression of inhibitory receptors on dendritic cells in vitro.

In one embodiment, the binding molecule is a mouse antibody.

In another embodiment, the binding molecule is a monoclonal antibody or antigen binding fragment thereof.

In yet another embodiment, the binding molecule is a humanized or chimeric antibody.

Another aspect of the invention features a composition comprising a binding molecule of the invention and a pharmaceutically acceptable carrier.

In one embodiment, the composition further comprises at least one additional therapeutic agent which upmodulates an immune response in a subject.

One aspect of the invention features a method for upmodulating an immune response in a subject, comprising contacting a cell from the subject with an anti-ILT3 antibody that inhibits immune cell activation in vitro.

Another aspect of the invention features a method for downmodulating transplant rejection in a subject, comprising contacting a cell from the subject with a binding molecule of the invention, and re-introducing the cell into the subject at the time of or prior to transplantation such that transplant rejection in a subject is downmodulated.

Yet another aspect of the invention features a method for treating cancer in a subject, comprising contacting a cell with a binding molecule of the invention, such that cancer is treated in a subject.

In one embodiment, the type of cancer is selected from the group consisting of: pancreatic cancer, melanomas, breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

One aspect of the invention features an isolated nucleic acid molecule comprising a nucleotide sequence encoding a heavy chain variable region comprising the nucleotide sequence of SEQ ID NO:9.

Another aspect of the invention features an isolated nucleic acid molecule comprising a nucleotide sequence encoding a light chain variable region comprising the nucleotide sequence of SEQ ID NO:10.

Yet another aspect of the invention features an isolated nucleic acid molecule comprising a nucleotide sequence encoding at least one CDR selected from the group consisting of: SEQ ID NO:11, SEQ ID NO:12, and SEQ ID NO:13. In one embodiment, the isolated nucleic acid molecule comprises at least two CDRs. In another embodiment, the isolated nucleic acid molecule comprises three CDRs.

Another aspect of the invention features an isolated nucleic acid molecule comprising a nucleotide sequence encoding at least one CDR selected from the group consisting of: SEQ ID NO:14 SEQ ID NO:15 and SEQ ID NO:16. In one embodiment, the isolated nucleic acid molecule comprises at least two CDRs. In another embodiment, the isolated nucleic acid molecule comprises three CDRs.

One aspect of the invention features an isolated nucleic acid molecule comprising the nucleotide sequences shown in SEQ ID NOs: 11-16.

One aspect of the invention features a recombinant expression vector comprising the nucleic acid molecules of the invention. In one embodiment, a recombinant expression vector comprising a nucleic acid molecule having a nucleotide sequence encoding the binding molecule of the invention is featured. In another embodiment, the invention features a host cell into which the recombinant expression vector of the invention has been introduced. In another aspect the invention features a method for producing a binding molecule that binds human ILT3, comprising culturing the host cell of the invention in a culture medium until a binding molecule that binds human ILT3 is produced by the cell.

BRIEF DESCRIPTION OF THE DRAWINGS

FIG. 3 is a graph that demonstrates that MDDCs cultured in the presence of the 9B11 antibody are unable to produce IL-12, TNFα or IL-1α when stimulated with LPS.

FIG. 5 shows that addition of the 9B11 antibody to monocytes, induced by activating an immunoreceptor tyrosine-based activation motif (ITAM) in CD32, inhibits Ca+2 flux.

DETAILED DESCRIPTION OF THE INVENTION

Figure 1:
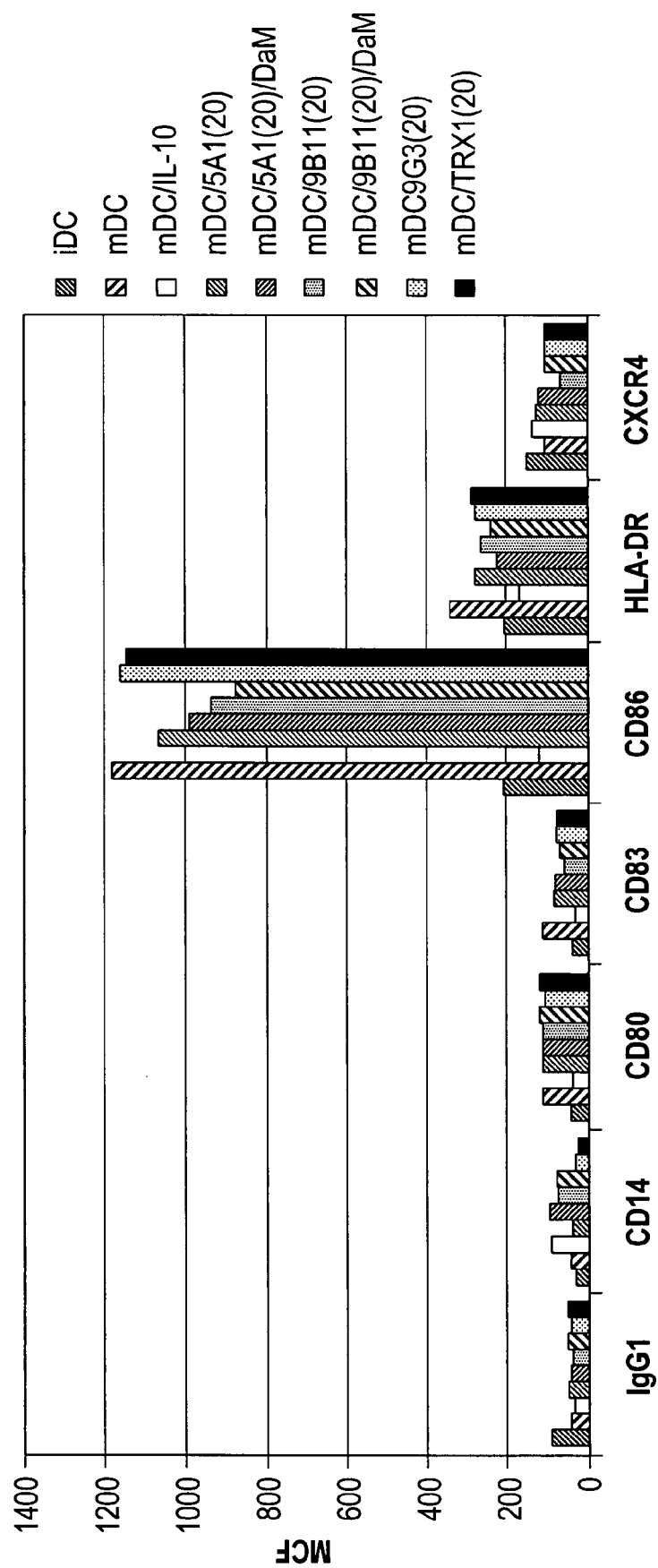
FIG. 1 is a graph demonstrating that monocyte-derived dendritic cells (MDDCs) differentiated in the presence of 9B11 exhibit a lower expression of cell surface co-stimulatory molecules, such as CD86, CD80, CD83 and HLA-DR, as measured by flow cytometry.

The present invention provides binding molecules that specifically bind to ILT3, e.g., human ILT3 (hILT3), on antigen presenting cells, such as for example, monocytes, macrophages and dendritic cells (DC), e.g., monocyte-derived dendritic cells (MDDC). The binding molecules of the invention are characterized by binding to hILT3 with high affinity and downmodulating immune responses in vitro, e.g., downmodulating alloimmune responses; the production of inflammatory cytokines by dendritic cells, e.g., monocyte-derived dendritic cells (MDDC); the upregulation of costimulatory molecules by DC, e.g., MDDC; and/or calcium flux in monocytes. In addition, the binding molecules upregulate the expression of inhibitory receptors on dendritic cells, e.g., immature dendritic cells. Surprisingly, these same binding molecules which downmodulate immune responses in vitro, are immunostimulatory in vivo.

Various aspects of the invention relate to binding molecules, and pharmaceutical compositions thereof, as well as nucleic acids encoding binding molecules, recombinant expression vectors and host cells for making such binding molecules. Methods of using a binding molecule of the invention to detect human ILT3 or to modulate human ILT3 activity, either in vitro or in vivo, are also encompassed by the invention.

In order that the present invention may be more readily understood, certain terms are first defined.

I. Definitions

The term "immunoglobulin-like transcript 3" (abbreviated herein as "ILT3" or "hILT3", and also known as CD85k), as used herein, refers to the human member of the immunoglobulin superfamily which is selectively expressed by myeloid antigen presenting cells (APCs) such as monocytes, macrophages, and dendritic cells, e.g., monocyte-derived dendritic cells differentiated in the presence of IL-10 or vitamin $D_3$. The ILT3 protein is a transmembrane protein of 447 amino acids with a predicted molecular mass of ~47 kD. The amino terminal portion of the ILT3 protein begins with a hydrophobic signal peptide of 23 amino acids followed by an extracellular region composed of two C2 type immunoglobulin superfamily domains. Each domain shows two characteristic cysteines that are 49 and 50 residues apart from each other, flanked by conserved residues (Val-x-Leu/Ile-x-Cys and His/Tyr-x-Gly-x-Tyr-x-Cys-Tyr/Phe, respectively, where x is any amino acid). The putative transmembrane domain of ILT3 consists of 21 amino acids, followed by a long cytoplasmic region of 167 amino acids, which is characterized by the presence of one Tyr-x-x-Val motif followed by two Tyr-x-x-Leu motifs spaced by 26 amino acid residues. These Tyr-x-x-Leu pairs and their spacing are reminiscent of the Tyr-x-x-Leu motifs (also referred to as immunoreceptor tyrosine-based inhibitory motifs or ITIMs) identified in KIRs (natural-killer cell Ig receptors) as binding sites for protein tyrosine phosphatase SHP-1.

The putative immunoreceptor tyrosine-based inhibitory motifs in the cytoplasmic region of ILT3 suggest an inhibitory function of ILT3. As such, ILT3 behaves as an inhibitory receptor when cross-linked to a stimulatory receptor.

The nucleic acid sequence of human (hILT3) ILT3 is set forth in SEQ ID NO:17 and the amino acid sequence is set forth in SEQ ID NO:18.

The term "binding molecule" as used herein includes molecules that contain at least one antigen binding site that specifically binds to ILT3. By "specifically binds" it is meant that the binding molecules exhibit essentially background binding to non-ILT3 molecules. An isolated binding molecule that specifically binds ILT3 may, however, have cross-reactivity to ILT3 molecules from other species.

The binding molecules of the invention may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. Binding molecules may have both a heavy and a light chain. As used herein, the term binding molecule also includes, antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, so long as they exhibit the desired activity, e.g., binding to ILT3.

An "antigen" is an entity (e.g., a proteinaceous entity or peptide) to which a binding molecule specifically binds.

The term "epitope" or "antigenic determinant" refers to a site on an antigen to which a binding molecule specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, X-ray crystallography and 2-dimensional nuclear magnetic resonance. See, e.g., *Epitope Mapping Protocols in Methods in Molecular Biology*, Vol. 66, G. E. Morris, Ed. (1996).

Binding molecules that recognize the same epitope can be identified in a simple immunoassay showing the ability of one antibody to block the binding of another antibody to a target antigen, i.e., a competitive binding assay. Competitive binding is determined in an assay in which the binding molecule being tested inhibits specific binding of a reference binding molecule to a common antigen, such as ILT3. Numerous types of competitive binding assays are known, for example: solid phase direct or indirect radioimmunoassay (RIA); solid phase direct or indirect enzyme immunoassay (EIA) sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test binding molecule and a labeled reference binding molecule. Competitive inhibition is measured by determining the amount of label bound to the solid surface or cells in the presence of the test binding molecule. Usually the test binding molecule is present in excess. Usually, when a competing binding molecule is present in excess, it will inhibit specific binding of a reference binding molecule to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

The term "monoclonal binding molecule" as used herein refers to a binding molecule obtained from a population of substantially homogeneous binding molecules. Monoclonal binding molecules are highly specific, being directed against a single antigenic site. Furthermore, in contrast to polyclonal binding molecule preparations which typically include different binding molecules directed against different determinants (epitopes), each monoclonal binding molecule is directed against a single determinant on the antigen. The modifier "monoclonal" indicates the character of the binding molecule as being obtained from a substantially homogeneous population of binding molecules, and is not to be construed as requiring production of the binding molecule by any particular method. For example, the monoclonal binding molecules to be used in accordance with the present invention may be made by the hybridoma method first described by Kohler, et al., *Nature* 256:495 (1975), or may be made by recombinant DNA methods (see, e.g., U.S. Pat. No. 4,816, 567). The "monoclonal binding molecules" may also be isolated from phage antibody libraries using the techniques described in Clackson, et al., *Nature* 352:624-628 (1991) and Marks et al., *J. Mol. Biol.* 222:581-597 (1991), for example.

The term "chimeric binding molecule" refers to a binding molecule comprising amino acid sequences derived from different species. Chimeric binding molecules can be constructed, for example by genetic engineering, from binding molecule gene segments belonging to different species.

The monoclonal binding molecules herein specifically include "chimeric" binding molecules in which a portion of the heavy and/or light chain is identical with or homologous to corresponding sequences in binding molecules derived from a particular species or belonging to a particular antibody class or subclass, while the remainder of the chain(s) is identical with or homologous to corresponding sequences in binding molecules derived from another species or belonging to another antibody class or subclass, as well as fragments of such binding molecules, so long as they exhibit the desired biological activity (U.S. Pat. No. 4,816,567; and Morrison, et al., *Proc. Natl. Acad. Sci. USA* 81:6851-6855 (1984)). e.g., binding to human ILT3 (hILT3).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

A "variable region" when used in reference to a binding molecule refers to the amino terminal portion of a binding molecule which confers antigen binding onto the molecule and which is not the constant region. The term includes complementarity determining regions and framework regions. The term also includes functional fragments thereof which maintain some or all of the binding function of the whole variable region.

The term "hypervariable region" when used herein refers to the regions of a binding molecule variable domain which are hypervariable in sequence and/or form structurally defined loops. The hypervariable region comprises amino acid residues from a "complementarity determining region" or "CDR".

As used herein, the term "CDR" or "complementarity determining region" means the noncontiguous antigen combining sites found within the variable region of both heavy and light chain polypeptides. These particular regions have been described by Kabat, et al., *J. Biol. Chem.* 252, 6609-6616 (1977) and Kabat, et al., Sequences of protein of immunological interest. (1991), and by Chothia, et al., *J. Mol. Biol.* 196:901-917 (1987) and by MacCallum, et al., *J. Mol. Biol.* 262:732-745 (1996) where the definitions include overlapping or subsets of amino acid residues when compared against each other. Preferably, the Kabat definition is used to describe a CDR of a binding molecule of the invention. Nevertheless, application of either definition to refer to a CDR of a binding molecule or grafted binding molecule or variants thereof is within the scope of the term as defined and used herein.

As used herein, the term "framework region" or "FR" means each domain of the framework that is separated by the CDRs. Therefore, a variable region framework is between about 100-120 amino acids in length but refers only those amino acids outside of the CDRs.

"Humanized" forms of non-human (e.g., murine) binding molecules are chimeric antibodies which contain minimal sequence derived from non-human binding molecule. For the most part, humanized binding molecules are human binding molecules (acceptor/recipient binding molecule) in which residues from a hyper-variable region are replaced by residues from a hypervariable region of a non-human species (donor binding molecule) such as mouse, rat, rabbit or non-human primate having the desired specificity, affinity, and capacity. In some instances, Fv framework region (FR) residues of the human binding molecule are altered, e.g., replaced by, substituted, or backmutated to corresponding non-human residues. Furthermore, humanized binding molecules may comprise residues which are not found in the recipient binding molecule or in the donor binding molecule. These modifications are generally made to further refine binding molecule performance. In general, the humanized binding molecule will comprise substantially all of at least one, and typically two, variable domains, in which all or substantially all of the hypervariable loops correspond to those of a non-human binding molecule and all or substantially all of the FR regions are those of a human binding molecule sequence. The humanized binding molecule optionally also will comprise at least a portion of a binding molecule constant region (Fc), typically that of a human binding molecule. For further details, see Jones, et al., *Nature* 321:522-525 (1986); Riechmann, et al., *Nature* 332:323-329 (1988); and Presta, *Curr. Op. Struct. Biol.* 2:593-596 (1992).

Preferably, a humanized binding molecule of the invention comprises at least one CDR selected from the group consisting of SEQ ID NO:3 (GFAFSSYDMS (VH CDR1)), SEQ ID NO:4 (TISSSGSYTYYPDSVKG (VH CDR2)), SEQ ID NO:5 (LWGAMDY (VH CDR3)), SEQ ID NO:6 (RASQGLTNDLH (VL CDR1)), SEQ ID NO:7 (YASQSIS (VL CDR2)), and SEQ ID NO:8 (QQSNSWPFT (VL CDR3)).

The term "engineered" or "recombinant" binding molecule, as used herein includes binding molecules that are prepared, expressed, created or isolated by recombinant means, such as binding molecules expressed using a recombinant expression vector transfected into a host cell, binding molecules isolated from a recombinant, combinatorial binding molecule library, binding molecules isolated from an animal (e.g., a mouse) that is transgenic for human immunoglobulin genes (see e.g., Taylor, L. D., et al. (1992) *Nucl. Acids Res.* 20:6287-6295) or binding molecules prepared, expressed, created or isolated by any other means that involves splicing of human binding molecule gene sequences to other DNA sequences. In certain embodiments, however, such recombinant human binding molecules are subjected to in vitro mutagenesis (or, when an animal transgenic for human Ig sequences is used, in vivo somatic mutagenesis) and thus the amino acid sequences of the VH and VL regions of the recombinant binding molecules are sequences that, while derived from and related to human germline VH and VL sequences, may not naturally exist within the human binding molecule germline repertoire in vivo.

An "isolated binding molecule", as used herein, refers to a binding molecule that is substantially free of other binding molecules having different antigenic specificities (e.g., an isolated binding molecule that specifically binds ILT3 is substantially free of binding molecules that specifically bind antigens other than ILT3). Moreover, an isolated binding molecule may be substantially free of other cellular material and/or chemicals. An "isolated" binding molecule is one which has been identified and separated and/or recovered from a component of its natural environment. Contaminant components of its natural environment include, e.g., materials which would interfere with diagnostic or therapeutic uses for the binding molecule, and may include enzymes, hormones, and other proteinaceous or nonproteinaceous solutes. In preferred embodiments, the binding molecule will be purified (1) to greater than 95% by weight of binding molecule as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding molecules include binding molecules in situ within recombinant cells since at least one component of the binding molecule's natural environment will not be present. Ordinarily, however, isolated binding molecules will be prepared by at least one purification step.

As used herein the term "binding constant" "(kd)", also referred to as "affinity constant", is a measure of the extent of a reversible association between two molecular species includes both the actual binding affinity as well as the apparent binding affinity. The actual binding affinity is determined by calculating the ratio of the Kassoc in $M^{-1}S^{-1}$ to the Kdissoc in $S^{-1}$ and has the units "$M^{-1}$". Therefore, conferring or optimizing binding affinity includes altering either or both of these components to achieve the desired level of binding affinity. The apparent affinity can include, for example, the avidity of the interaction. For example, a bivalent heteromeric variable region binding fragment can exhibit altered or optimized binding affinity due to its valency. Binding affinity can be determined by measurement of surface plasmon resonance, e.g., using a BIAcore system.

The term "nucleic acid molecule", as used herein, includes DNA molecules and RNA molecules. A nucleic acid molecule may be single-stranded or double-stranded, but preferably is double-stranded DNA.

The term "isolated nucleic acid molecule", as used herein in reference to nucleic acids encoding binding molecules that bind ILT3, refers to a nucleic acid molecule in which the nucleotide sequences encoding the binding molecule are free of other nucleotide sequences which other sequences may naturally flank the nucleic acid in human genomic DNA. These sequences may optionally include 5' or 3'nucleotide sequences important for regulation or protein stability.

The term "vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention includes such other forms of expression vectors, such as viral vectors (e.g., replication defective retroviruses, adenoviruses and adeno-associated viruses), which serve equivalent functions.

The term "recombinant host cell" (or simply "host cell"), as used herein, refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "T cell" (i.e., T lymphocyte) is includes cells within the T cell lineage, including thymocytes, immature T cells, mature T cells and the like, from a mammal (e.g., human). Preferably, T cells are mature T cells that express either CD4 or CD8, but not both, and a T cell receptor. The various T cell populations described herein can be defined based on their cytokine profiles and their function.

As used herein, a "professional antigen presenting cell" or "APC" is a cell that can present antigen in a form in which it can be recognized by cells. The cells that can "present" antigen include B cells, monocytes, macrophages and dendritic cells.

As used herein, the term "dendritic cell" or "DC" includes APCs capable of activating naïve T cells and stimulating the growth and differentiation of B cells. DCs are lineage negative cells, i.e., they lack cell surface markers for T cells, B cells, NK cells, and monocytes/macrophages, however they strongly express various costimulatory molecules (e.g., CD86, CD80, CD83, and HLA-DR) and/or adhesion molecules. Dendritic cells can be subdivided into two main cell types, namely "myeloid-derived dendritic cells" ("MDDC") and "plasmacytoid-derived dendritic cells" ("PDDC"). Cell surface markers, such as ILT3, can be used to distinguish the two dendritic cell lineages, as can the limited proliferative ability of PDDC. See, for example, Santiago-Schwartz, F. (2004) *Rheum. Dis. Clin. Noth Am.* 30:115-134, incorporated herein by reference. Furthermore, DCs can also be divided into "immature DCs" and "mature DCs". Immature DCs are specialized in antigen capture and processing, whereas mature DCs present antigen and have an increased T-cell stimulatory capacity. Immature DCs can be matured using art recognized techniques, such as culturing in the presence of an inflammatory cytokine cocktail.

As used herein, the term "naïve T cells" includes T cells that have not been exposed to cognate antigen and so are not activated or memory cells. Naïve T cells are not cycling and human naïve T cells are CD45RA+. If naïve T cells recognize antigen and receive additional signals depending upon but not limited to the amount of antigen, route of administration and timing of administration, they may proliferate and differentiate into various subsets of T cells, e.g. effector T cells.

As used herein, the term "memory T cell" includes lymphocytes which, after exposure to antigen, become functionally quiescent and which are capable of surviving for long periods in the absence of antigen. Human memory T cells are CD45RA−.

As used herein, the term "effector T cell" or "Teff cell" includes T cells which function to eliminate antigen (e.g., by producing cytokines which modulate the activation of other cells or by cytotoxic activity). The term "effector T cell" includes T helper cells (e.g., Th1 and Th2 cells) and cytotoxic T cells. Th1 cells mediate delayed type hypersensitivity (DTH) responses and macrophage activation (e.g., cellular immune responses) while Th2 cells provide help to B cells and are critical in the allergic response (e.g., humoral immune responses) (Mosmann and Coffman, 1989, *Annu. Rev. Immunol.* 7, 145-173; Paul and Seder, 1994, *Cell* 76, 241-251; Arthur and Mason, 1986, *J. Exp. Med.* 163, 774-786; Paliard, et al., 1988, *J. Immunol.* 141, 849-855; Finkelman, et al., 1988, *J. Immunol.* 141, 2335-2341).

As used herein, the term "T helper type 1 response" (Th1 response) refers to a response that is characterized by the production of one or more cytokines selected from IFN-γ, IL-2, TNF, and lymphotoxin (LT) and other cytokines produced preferentially or exclusively by Th1 cells rather than by Th2 cells. As used herein, a "T helper type 2 response" (Th2 response) refers to a response by CD4+ T cells that is characterized by the production of one or more cytokines selected from IL-4, IL-5, IL-6 and IL-10, and that is associated with efficient B cell "help" provided by the Th2 cells (e.g., enhanced IgG1 and/or IgE production).

As used herein, the term "regulatory T cell" or "Treg cell" includes T cells which produce low levels of IL-2, IL-4, IL-5, and IL-12. Regulatory T cells produce TNFα, TGFβ, IFN-γ, and IL-10, albeit at lower levels than effector T cells. Although TGFβ is the predominant cytokine produced by regulatory T cells, the cytokine is produced at levels less than or equal to that produced by Th1 or Th2 cells, e.g., an order of magnitude less than in Th1 or Th2 cells. Regulatory T cells can be found in the CD4+ CD25+population of cells (see, e.g., Waldmann and Cobbold. 2001. *Immunity*. 14:399). Regulatory T cells actively suppress the proliferation and cytokine production of Th1, Th2, or naïve T cells which have been stimulated in culture with an activating signal (e.g., antigen and antigen presenting cells or with a signal that mimics antigen in the context of MHC, e.g., anti-CD3 antibody, plus anti-CD28 antibody).

As used herein, the term "anergy" or "tolerance" includes refractivity to activating receptor-mediated stimulation. Such refractivity is generally antigen-specific and persists after exposure to the tolerizing antigen has ceased. For example, tolerance is characterized by lack of cytokine production, e.g., IL-2. Tolerance occurs when cells are exposed to antigen and receive a first signal (a T cell receptor or CD-3 mediated signal) in the absence of a second signal (a costimulatory signal) or by modulation, e.g., upmodulation of an inhibitory signal from an inhibitory receptor, such as, for example, ILT3. Under these conditions, reexposure of the cells to the same antigen (even if reexposure occurs in the presence of a costimulatory polypeptide) results in failure to produce cytokines and, thus, failure to proliferate. For example, tolerance is characterized by lack of cytokine production, e.g., IL-2, or can be assessed by use of a mixed lymphocyte culture assay. Tolerance can occur to self antigens or to foreign antigens.

As used herein, the term "inhibitory signal" refers to a signal transmitted via an inhibitory receptor (e.g., ILT3), e.g., on an immune cell, such as a DC, e.g., MDDC. Such a signal antagonizes a signal via an activating receptor (e.g., via a TCR, CD3, BCR, or Fc polypeptide). Transduction of a signal via an inhibitory receptor results in "downmodulation of immune cell activation" in vitro. Transmission of a regulatory signal which can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of tolerance.

In one embodiment, downmodulation of immune cell activation in vitro downmodulates an alloimmune response. As used herein, an "alloimmune response" refers to an immune response that occurs between antigenically distinct cells. An alloimmune response can be measured utilizing a "mixed lymphocyte culture or reaction" ("MLC" or "MLR") which is a type of lymphocyte proliferation test in which lymphocytes, i.e., resting lymphocytes, i.e., lymphocytes that have not been stimulated, from two individuals (a stimulator and a responder), i.e., allogenic lymphocytes, are cultured together and the proliferative response ("mixed lymphocyte reaction") is measured by $^3$H-labeled thymidine uptake and/or cytokine production.

In one embodiment, the MLC is a primary MLC, i.e., responder cells are mixed with stimulator cells at, which may or may not have been inactivated by, e.g., gamma irradiation and cultured for, e.g., 3 days. In another embodiment, the MLC is a secondary MLC, i.e., responder cells are initially cultured in a primary MLC with stimulator cells which may or may not have been inactivated by, e.g., gamma irradiation at, and subsequently viable cells are recovered and restimulated with new stimulators cells, which may or may not have been inactivated by, e.g., gamma irradiation, and cultured for an additional, e.g., 3, 4, 5, 6, 7 days.

In another embodiment, downmodulation of immune cell activation results in downmodulation of the expression of costimulatory molecules on a cell, e.g., a dendritic cell, or a dampening in an increase in costimulatory molecule expression. In yet another embodiment, downmodulation of immune cell activation in vitro results in downmodulation of intracellular calcium flux.

In one embodiment, the activation state of MDDC is downmodulated in vitro. In one embodiment, MDDC are derived from monocytes cultured in the presence of, e.g., GM-CSF and IL-4 added on, e.g., days zero and three. In one embodiment, MDDC are derived from monocytes cultured in the presence of a binding molecule of the invention added on, e.g., days zero and three. In another embodiment the activation state of mature dendritic cells is downmodulated. In one embodiment, mature dendritic cells are derived from blood dendritic cells cultured in the presence of, e.g., IL-6, IL-1 beta, TNF-alpha, and PGE added on, e.g., day one. In another embodiment the activation state of monocytes is downmodulated.

As used herein "upmodulation of an immune response" refers to an increase in a T cell mediated and/or B cell mediated immune response in vivo. Exemplary immune responses include T cell responses, e.g., cytokine production, and cellular cytotoxicity. In addition, the term immune response includes antibody production (humoral responses) and activation of cells of the innate immune system, e.g., cytokine responsive cells such as macrophages.

As used herein, the various forms of the term "modulate" include stimulation (e.g., increasing, upmodulating, or upregulating a particular response or activity) and inhibition (e.g., decreasing, downmodulating, or downregulating a particular response or activity).

"Treatment" refers to both therapeutic treatment and prophylactic or preventative measures. Those in need of treatment may include those already having a disorder as well as those which do not yet have a disorder.

A "disorder" is any condition that would benefit from treatment with the binding molecules of the present invention. This includes chronic and acute disorders or diseases or pathological conditions associated with immune responses that are too high or too low.

Various aspects of the invention are described in further detail in the following subsections.

II. ILT3 Binding Molecules

The present invention provides isolated ILT3 binding molecules. Exemplary binding molecules of the present invention include the 9B11 antibody, or a binding portion thereof. The 9B11 antibody is an anti-ILT3 antibody that binds to ILT3 on APC, e.g., monocytes, macrophages, dendritic cells, e.g., MDDC, e.g., human cells, with high affinity. The binding molecules of the invention are characterized by binding to hILT3 with high affinity and downmodulating immune responses in vitro, e.g., downmodulating alloimmune responses; the production of inflammatory cytokines by dendritic cells, e.g., monocyte-derived dendritic cells (MDDC); the upregulation of costimulatory molecules by DC, e.g., MDDC; and/or calcium flux in monocytes. In addition, the binding molecules upregulate the expression of inhibitory receptors on dendritic cells, e.g., immature dendritic cells.

Surprisingly, these same binding molecules which down-modulate immune responses in vitro, are immunostimulatory in vivo. For example, the binding molecules stimulate immune responses in vivo such as cellular immune responses, e.g., DTH responses.

In one embodiment, the VH domain of a binding molecule of the invention comprises the amino acid sequence set forth in SEQ ID NO: 1. (MEFGLSLVFLVLILKGVQCEVKLVESGGDLVKPGGSLKLSCAASGFAFSSYD MSWVRQTPEKRLEWVATISSSGSYTYYPDSVKGRFTISRDNARNTLYLQMSSLRSEDTALYYCERLWGAMDYWGQGTLVTVSS) (9B11 VH domain, including leader)). It will be understood that although some of the sequences of binding molecules described herein include leader sequences, a binding molecule of the invention may also exclude the leader sequence; which is optional. For example, in one embodiment, a binding molecule of the invention comprises the amino acid sequence of the mature protein shown in SEQ ID NO:1. e.g., amino acids 20-135 of SEQ ID NO:1.

In one embodiment, a VL domain of a binding molecule of the invention comprises the amino acid sequence set forth in SEQ ID NO:2. (METDTILLWVLLLWVPGSTGDIVLTQSPATLSVTPGDSVSLSCRASQGLTND LHWYQQKPHESPRLLIKYASQSISGIPSRFSGSGSGTDFTLTINSVETEDFGVFF CQQSNSWPFTFGAGTKLEIK) (9B11 VL domain, including leader)).

In one embodiment, a VH domain of a binding molecule of the invention comprises amino acid residues 20-135 of SEQ ID NO.: 1. (EVKLVESGGDLVKPGGSLKLSCAASGFAFSSYDMSWVRQTPEKRLEWVATISSSGSYT YYPDSVKGRFTISRDNARNTLYLQMSSLRSEDTALYYCERLWGAMDYWGQGTLVTVSS) (9B11 VH domain, without leader)).

In one embodiment, a VL domain of a binding molecule of the invention comprises amino acid residues 21-127 of SEQ ID NO.:2. (DIVLTQSPATLSVTPGDSVSLSCRASQGLTNDLHWYQQKPHESPRLLIKYASQS ISGIPSRFSGSGSGTDFTLTINSVETEDFGVFFCQQSNSWPFTFGAGTKLEIK) (9B11 VL domain, without leader)).

In one embodiment of the invention a VL chain comprises a leader and/or signal sequence, i.e., amino acid residues 1-20 of SEQ ID NO:2 (SEQ ID NO:21). In one embodiment, the VH chain comprises a leader and/or signal sequence, i.e., amino acid residues 1-19 of SEQ ID NO:1 (SEQ ID NO:22).

In one embodiment, a binding molecule of the invention comprises a VH domain comprising a CDR set forth in SEQ ID NO:3. (9B11 VH CDR1).

In one embodiment, a binding molecule of the invention comprises a VH domain comprising a CDR set forth in SEQ ID NO:4. (9B11 VH CDR2).

In one embodiment, a binding molecule of the invention comprises a VH domain comprising a CDR set forth in SEQ ID NO:5. (9B11 VH CDR3).

In one embodiment, a binding molecule of the invention comprises a VL domain comprising a CDR set forth in SEQ ID NO:6. (9B11 VL CDR1).

In one embodiment, a binding molecule of the invention comprises a VL domain comprising a CDR set forth in SEQ ID NO:7. (9B11 VL CDR2).

In one embodiment, a binding molecule of the invention comprises a VL domain comprising a CDR set forth in SEQ ID NO:8. (9B11 VL CDR3).

The invention also pertains to nucleic acid molecules encoding the above amino acid sequences.

In one embodiment, a VH domain of a binding molecule of the invention comprises the nucleotide sequence set forth in SEQ ID NO:9. (9B11 VH domain, including leader).

In one embodiment, a VH domain of a binding molecule of the invention comprises nucleotides 58-405 of SEQ ID NO.: 9. (9B11 VH domain, without leader).

In one embodiment, the a VL domain of a binding molecule of the invention comprises the nucleotide sequence set forth in SEQ ID NO:10. (9B11 VL domain, including leader).

In one embodiment, the a VL domain of a binding molecule of the invention comprises nucleotides 61-383 of SEQ ID NO.: 10. (9B11 VL domain, without leader).

In one embodiment, a binding molecule of the invention comprises a VH domain comprising a CDR the nucleic acid sequence of which is set forth in SEQ ID NO:11. (9B11 VH CDR1).

In one embodiment, a binding molecule of the invention comprises a VH domain comprising a CDR the nucleic acid sequence of which is set forth in SEQ ID NO: 12. (9B11 VH CDR2).

In one embodiment, a binding molecule of the invention comprises a VH domain comprising a CDR the nucleic acid sequence of which is set forth in SEQ ID NO:13. (9B11 VH CDR3).

In one embodiment, a binding molecule of the invention comprises a VL domain comprising a CDR the nucleic acid sequence of which is set forth in SEQ ID NO:14. (9B11 VL CDR1).

In one embodiment, a binding molecule of the invention comprises a VL domain comprising a CDR the nucleic acid sequence of which is set forth in SEQ ID NO: 15. (9B11 VL CDR2).

In one embodiment, a binding molecule of the invention comprises a VL domain comprising a CDR the nucleic acid sequence of which is set forth in SEQ ID NO:16. (9B11 VL CDR3).

In one embodiment, the a CL domain of a binding molecule of the invention comprises the amino acid sequence set forth in SEQ ID NO:23. (Murine IgG2a light chain constant region).

In one embodiment, the a CH domain of a binding molecule of the invention comprises the amino acid sequence set forth in SEQ ID NO:24. (Murine IgG2a heavy chain constant region).

In one embodiment, a binding molecule of the invention comprises the amino acid sequence set forth in SEQ ID NO:25. (Chimeric 9B11 VL/human CL IgG1).

In one embodiment, a binding molecule of the invention comprises the amino acid sequence set forth in SEQ ID NO:26. (Chimeric 9B13 VH/human Gly-CH IgG1).

In one embodiment, a binding molecule of the invention comprises the amino acid sequence set forth in SEQ ID NO:27. (Chimeric 9B11 VH/human Agly-CH IgG1).

In one embodiment, a binding molecule of the invention comprises the amino acid sequence set forth in SEQ ID NO:28. (Humanized 9B11 VL).

In one embodiment, a binding molecule of the invention comprises the amino acid sequence set forth in SEQ ID NO:29. (Humanized 9B11 VH).

In one embodiment, the a CL domain of a binding molecule of the invention comprises the amino acid sequence set forth in SEQ ID NO:30. (Human IgG1 Gly heavy chain constant region).

In one embodiment, the a CH domain of a binding molecule of the invention comprises the amino acid sequence set forth in SEQ ID NO:31. (Human IgG1 Agly heavy chain constant region).

In one embodiment, the a CL domain of a binding molecule of the invention comprises the amino acid sequence set forth in SEQ ID NO:32. (Human IgG1 light chain constant region).

In one embodiment, a binding molecule of the invention comprises the amino acid sequence set forth in SEQ ID NO:33. (Complete Humanized 9B11 Light).

In one embodiment, a binding molecule of the invention comprises the amino acid sequence set forth in SEQ ID NO:34. (Complete Humanized 9B11 Heavy-Gly).

In one embodiment, a binding molecule of the invention comprises the amino acid sequence set forth in SEQ ID NO:35. (Complete Humanized 9B13 Heavy-Agly).

In one embodiment, a binding molecule of the invention has the VL amino acid sequence of the 9B11 VL region as set forth in SEQ ID NO: 2 and the VH amino acid sequence of the 9B11 VH region as set forth in SEQ ID NO: 1. In another embodiment, a binding molecule of the invention has LC and HC sequences as set forth in SEQ ID NOs:23 and 24, respectively; ADAAPTVSIFPPSSEQLTSGGASVVC-FLNNFYPKDINVKWKIDGSERQNGVLN SWTDQD-SKDSTYSMSSTLTLTKDEYERHNSYTCEATHKTSTS PIVKSFNRNE (SEQ ID NO:23);
AKTTPPSVYPLAPGCGDTTGSSVTLG-
CLVKGYFPESVTVTWNSGSLSSSVHTF PALLQSG-
LYTMSSSVTVPSSTWPSQTVTCSVAH-
PASSTTVDKKLEPSGPISTIN
PCPPCKECKCPAPNLEGGPSVFIFPPNI-
KDVLMISLTPKVTCVVVDVSEDDPDV QISWFVN-
NVEVHTAQTQTHREDYNSTIRV-
VSTLPIQHQDWMSGKEFKCKVN
NKDLPSPIERTISKIKGLVRAQVYILPP-
PAEQLSRKDVSLTCLVVGFNPGDISVE WTSNGH-
TEENYKDTAPVLDSDGSYFIYSKLN-
MKTSKWEKTDSFSCNVRHEG
LKNYYLKKTISRSPGK (SEQ ID NO:24).

In one embodiment of the invention the VL chain comprises a leader and/or signal sequence, e.g., amino acid residues 1-20 of SEQ ID NO:2. In one embodiment, the VH chain comprises a leader and/or signal sequence, e.g., amino acid residues 1-19 of SEQ ID NO:1. In another embodiment, a binding molecule of the invention does not comprise a leader and/or signal sequence.

In one aspect, the invention pertains to 9B11 binding molecules and other binding molecules with equivalent properties to 9B11, such as binding to hILT3 with high affinity and downmodulate immune responses in vitro, e.g., downmodulate alloimmune responses; the production of inflammatory cytokines by dendritic cells, e.g. monocyte-derived dendritic cells (MDDC); the upregulation of costimulatory molecules by DC, e.g., MDDC; and/or calcium flux in monocytes; and upregulate the expression of inhibitory receptors on dendritic cells, e.g., immature dendritic cells and stimulating immune response in vivo, such as a Th1 immune responses. Accordingly, equivalent binding molecules of the invention e.g., generate a negative signal in a cell via ILT3 or block generation of a stimulatory signal via an activating receptor in vitro, while they are immunostimulatory in vivo, e.g., they sequester or dowumodulate ILT3 to prevent its association with an activating receptor, thereby preventing the downmodulation of an immune response.

In one embodiment, the invention provides an isolated human binding molecule with a light chain variable region (VL) comprising the amino acid sequence of SEQ ID NO: 2, and optionally a leader sequence, and a heavy chain variable region (VH) comprising the amino acid sequence of SEQ ID NO: 1, and optionally a leader sequence. In certain embodiments of the invention, the binding molecules of the invention comprise a heavy chain constant region, such as an IgG1, IgG2, IgG3, IgG4, IgA, IgE, IgM or IgD constant region. Furthermore, the binding molecule can comprise a light chain constant region, either a kappa light chain constant region or a lambda light chain constant region. Preferably, the binding molecule comprises a kappa light chain constant region.

In one embodiment, a binding molecule of the invention comprises a light chain constant region as set forth in SEQ ID NO:23. In one embodiment, a binding molecule of the invention comprises a heavy chain constant region as set forth in SEQ ID NO:24. In one embodiment, a binding molecule of the invention comprises a heavy chain constant region as set forth in SEQ ID NO:30. In one embodiment, a binding molecule of the invention comprises a heavy chain constant region as set forth in SEQ ID NO:31. In one embodiment, a binding molecule of the invention comprises a light chain constant region as set forth in SEQ ID NO:32.

In another embodiment, the invention provides a binding molecule having 9B11-related VL CDR domains, for example, a binding molecule with a light chain variable region (VL) having at least one CDR domain comprising an amino acid sequence selected from the group consisting of SEQ ID NO: 6, SEQ ID NO: 7, and SEQ ID NO: 8. In another embodiment, a light chain variable region (VL) has at least two CDR domains comprising an amino acid sequence selected from the group consisting of SEQ ID NO: 6, SEQ ID NO: 7, and SEQ ID NO: 8. In yet another embodiment, a light chain variable region (VL) has CDR domains comprising the amino acid sequences consisting of SEQ ID NO: 6, SEQ ID NO: 7, and SEQ ID NO: 8.

In still other embodiments, the invention provides a binding molecule having 9B11-related VH CDR domain, for example, a binding molecule with a heavy chain variable region (VH) having at least one CDR domain comprising an amino acid sequence selected from the group consisting of SEQ ID NO: 3, SEQ ID NO: 4, and SEQ ID NO: 5. In another embodiment, a heavy chain variable region (VH) has at least two CDR domains comprising an amino acid sequence selected from the group consisting of SEQ ID NO: 3, SEQ ID NO: 4, and SEQ ID NO: 5. In yet another embodiment, a heavy chain variable region (VH) has CDR domains comprising the amino acid sequences consisting of SEQ ID NO: 3, SEQ ID NO: 4, and SEQ ID NO: 5.

In another embodiment, a binding molecule of the invention comprises at least one CDR derived from a murine anti-human ILT3 binding molecule, e.g., a 9B11 binding molecule. As used herein the term "derived from" a designated protein refers to the origin of the polypeptide. In one embodiment, the polypeptide or amino acid sequence which is derived from a particular starting polypeptide is a CDR sequence or sequence related thereto. In another embodiment, the polypeptide or amino acid sequence which is derived from a particular starting polypeptide is a FR sequence or sequence related thereto. In one embodiment, the amino acid sequence which is derived from a particular starting polypeptide is not contiguous.

For example, in one embodiment, one, two, three, four, five, or six CDRs are derived from a murine 9B11 antibody. In one embodiment, a binding molecule of the invention comprises at least one heavy or light chain CDR of a murine 9B11 antibody. In another embodiment, a binding molecule of the invention comprises at least two CDRs from a murine 9B11 antibody. In another embodiment, a binding molecule of the invention comprises at least three CDRs from a murine 9B11 antibody. In another embodiment, a binding molecule of the invention comprises at least four CDRs from a murine 9B11 antibody. In another embodiment, a binding molecule of the invention comprises at least five CDRs from a murine 9B11 antibody. In another embodiment, a binding molecule of the invention comprises at least six CDRs from a murine 9B11 antibody.

It will also be understood by one of ordinary skill in the art that a binding molecule of the invention may be modified such that they vary in amino acid sequence from the 9B11 molecule from which they were derived. For example, nucleotide or amino acid substitutions leading to conservative substitutions or changes at "non-essential" amino acid residues may be made (e.g., in CDR and/or framework residues) and maintain the ability to bind to ILT3, e.g., human ILT3.

In one embodiment, a binding molecule of the invention comprises a polypeptide or amino acid sequence that is essentially identical to that of a 9B11 antibody, or a portion thereof wherein the portion consists of at least 3-5 amino acids, of at least 5-10 amino acids, at least 10-20 amino acids, at least 20-30 amino acids, or at least 30-50 amino acids, or which is otherwise identifiable to one of ordinary skill in the art as having its origin in the starting sequence.

In another embodiment, a VL region of a binding molecule of the invention shares an amino acid sequence identity that is about 80%, 85%, 86%, 87%, 88%, 89%, 90%, 91%, 92%, 93%, 94%, 95%, 96%, 97%, 98%, 99%, to that of a 9B11 VL region wherein the portion consists of at least 3-5 amino acids, of at least 5-10 amino acids, at least 10-20 amino acids, at least 20-30 amino acids, or at least 30-50 amino acids, or which is otherwise identifiable to one of ordinary skill in the art as having its origin in the starting sequence.

In another embodiment, a VH region of a binding molecule of the invention shares an amino acid sequence identity that is about 80%, 85%, 86%, 87%, 88%, 89%, 90%, 91%, 92%, 93%, 94%, 95%, 96%, 97%, 98%, 99%, to that of a 9B11 VH region wherein the portion consists of at least 3-5 amino acids, of at least 5-10 amino acids, at least 10-20 amino acids, at least 20-30 amino acids, or at least 30-50 amino acids, or which is otherwise identifiable to one of ordinary skill in the art as having its origin in the starting sequence.

In another embodiment, a CDR of a binding molecule of the invention shares an amino acid sequence identity that is about 80%, 85%, 86%, 87%, 88%, 89%, 90%, 91%, 92%, 93%, 94%, 95%, 96%, 97%, 98%, 99%, to that of a 9B11 CDR, or which is otherwise identifiable to one of ordinary skill in the art as having its origin in the starting sequence.

In another embodiment, the polypeptide or amino acid sequence which is derived from a particular starting polypeptide or amino acid sequence shares an amino acid sequence identity that is about 80%, 85%, 86%, 87%, 88%, 89%, 90%, 91%, 92%, 93%, 94%, 95%, 96%, 97%, 98%, 99%, or which is otherwise identifiable to one of ordinary skill in the art as having its origin in the starting sequence.

An isolated nucleic acid molecule encoding a non-natural variant of a polypeptide can be created by introducing one or more nucleotide substitutions, additions or deletions into the nucleotide sequence of the binding molecule such that one or more amino acid substitutions, additions or deletions are introduced into the encoded protein. Mutations may be introduced by standard techniques, such as site-directed mutagenesis and PCR-mediated mutagenesis. In one embodiment, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan; histidine). Thus, a nonessential amino acid residue in a binding molecule polypeptide may be replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the binding molecule coding sequence.

Preferred binding molecules of the invention comprise framework and constant region amino acid sequences derived from a human amino acid sequence. However, binding molecules may comprise framework and/or constant region sequences derived from another mammalian species. For example, a primate framework region (e.g., non-human primate), heavy chain portion, and/or hinge portion may be included in the subject binding molecules. In one embodiment, one or more murine amino acids may be present in the framework region of a binding polypeptide, e.g., a human or non-human primate framework amino acid sequence may comprise one or more amino acid substitutions and/or back-mutations in which the corresponding murine amino acid residue is present. Preferred binding molecules of the invention are less immunogenic than the starting 9B11 murine antibody.

The present invention also features chimeric and/or humanized binding molecules (i.e., chimeric and/or humanized immunoglobulins) specific for ILT3. Chimeric and/or humanized binding molecules have the same or similar binding specificity and affinity as a mouse or other nonhuman binding molecules that provide the starting material for construction of a chimeric or humanized binding molecule.

A chimeric binding molecule is one whose light and heavy chain genes have been constructed, typically by genetic engineering, from immunoglobulin gene segments belonging to different species. For example, the variable (V) segments of the genes from a mouse monoclonal binding molecule may be joined to human constant (C) segments, such as IgG1 or IgG4. Human isotype IgG1 is preferred. An exemplary chimeric binding molecule is thus a hybrid protein consisting of the V or antigen-binding domain from a mouse binding molecule and the C or effector domain from a human binding molecule.

In one embodiment, the invention pertains to humanized variable regions of the 9B11 binding molecule and polypeptides comprising such humanized variable regions. In one embodiment, a binding molecule of the invention comprises at least one humanized 9B11 binding molecule variable region, e.g., a light chain or heavy chain variable region.

The term "humanized binding molecule" refers to a binding molecule comprising at least one chain comprising variable region framework residues derived from a human binding molecule chain (referred to as the acceptor immunoglobulin or binding molecule) and at least one complementarity determining region derived from a mouse-binding molecule, (referred to as the donor immunoglobulin or binding molecule). Humanized binding molecules can be produced using recombinant DNA technology, which is discussed below. See for example, e.g., Hwang, W. Y. K., et al. (2005) *Methods* 36:35; Queen et al., Proc. Natl. Acad. Sci. USA, (1989), 86:10029-10033; Jones et al., Nature, (1986), 321:522-25; Riechmann et al., Nature, (1988), 332:323-27; Verhoeyen et al., Science, (1988), 239:1534-36; Orlandi et al., Proc. Natl. Acad. Sci. USA, (1989), 86:3833-37; U.S. Pat. Nos. 5,225,539; 5,530,101; 5,585,089; 5,693,761; 5,693,762; 6,180,370, Selick et al., WO 90/07861, and Winter, U.S. Pat. No. 5,225,539 (incorporated by reference in their entirety for all purposes). The constant region(s), if present, are preferably is also derived from a human immunoglobulin.

When a preferred non-human donor binding molecule has been selected for humanization, an appropriate human acceptor binding molecule may be obtained, e.g., from sequence databases of expressed human antibody genes, from germline Ig sequences or a consensus sequence of several human binding molecules.

In one embodiment, a CDR homology based method is used for humanization (see, e.g., Hwang, W. Y. K., et al. (2005) *Methods* 36:35, the contents of which is incorporated in its entirety herein by this reference). This method generally involves substitution of mouse CDRs into a human variable domain framework based on similarly structured mouse and human CDRs rather than similarly structured mouse and human frameworks. The similarity of the mouse and human CDRs is generally determined by identifying human genes of the same chain type (light or heavy) that have the same combination of canonical CDR structures as the mouse binding molecules and thus retain three-dimensional conformation of CDR peptide backbones. Secondly, for each of the candidate variable genes with matching canonical structures, residue to residue homology between the mouse and candidate human CDRs is evaluated. Finally, to generate a humanized binding molecule, CDR residues of the chosen human candidate CDR not already identical to the mouse CDR are converted to the mouse sequence. In one embodiment, no mutations of the human framework are introduced into the humanized binding molecule.

In one embodiment, human germline sequences are evaluated for CDR homology to the ILT3 binding molecule CDRs. For example, for the murine 9B11 antibody, all germ line light chain kappa chain V genes with a 2-1-1 canonical structure in the IMGT database were compared with the 9B11 antibody sequence. The same was done for the heavy chain where all 1-3 germ line heavy chain V genes were compared to the 9B11 amino acid sequence. Accordingly, in one embodiment, a binding molecule of the invention comprises a human kappa chain V region framework with a 2-1-1 canonical structure. In another embodiment, a binding molecule of the invention comprises a human heavy chain V region framework with a 1-3 canonical structure.

The following potential human light chain germline sequences were identified and may provide framework regions for a binding molecule of the invention. More specifically, such molecules may provide a scaffold in which any residue of the human light chain germline CDR not identical to the 9B11 light chain CDR may be changed to the mouse CDR amino acid:

There are two alleles of the IGKV1-17 gene. The IMGT accession number of allele *01 of the IGKV1-17 gene is X72808. The amino acid sequence is:

(SEQ ID NO:36)
DIQMTQSPSSLSASVGDRVTITCRASQGIRNDLGWYQQKPGKAPKRLIYA

ASSLQSGVPSRFSGSGSGTEFTLTISSLQPEDFATYYCLQHNSYP.

The IMGT accession number of allele *02 of the IGKV1-17 gene is D88255. The amino acid sequence is:

(SEQ ID NO:37)
DIQMTQSPSSLSASVGDRVTITCRASQGIRNDLGWYQQKPGKAPKRLIYA

ASSLQSGVPSRFSGSGSGTEFTLTISNLQPEDFATYYCLQHNSYP.

The IMGT accession number of the IGKV1-6 gene is M64858. The amino acid sequence is:

(SEQ ID NO:38)
AIQMTQSPSSLSASVGDRVTITCRASQGIRNDLGWYQQKPGKAPKLLIYA

ASSLQSGVPSRFSGSGSGTDFTLTISSLQPEDFATYYCLQDYNYP.

The IMGT accession number of the IGKV1-9 gene is Z00013. The amino acid sequence is:

(SEQ ID NO:39)
DIQLTQSPSFLSASVGDRVTITCRASQGISSYLAWYQQKPGKAPKLLIYA

ASTLQSGVPSRFSGSGSGTEFTLTISSLQPEDFATYYCQQLNSYP.

There are two alleles of the IGKV1-12 gene. The IMGT accession number of allele *01 of the IGKV1-12 gene is V01577. The amino acid sequence is:

(SEQ ID NO:40)
DIQMTQSPSSVSASVGDRVTITCRASQGISSWLAWYQQKPGKAPKLLIYA

ASSLQSGVPSRFSGSGSGTDFTLTISSLQPEDFATYYCQQANSFP.

The IMGT accession number of allele *02 of the IGKV1-12 gene is V01576. The amino acid sequence is:

(SEQ ID NO:41)
DIQMTQSPSSVSASVGDRVTITCRASQGISSWLAWYQQKPGKAPKLLIYA

ASSLQSGVPSRFSGSGSGTDFTLTISSLQPEDFATYYCQQANSFP.

There are two alleles of the IGKV1D-16 gene. The IMGT accession number of allele *01 of the IGKV1D-16 gene is K01323. The amino acid sequence is:

(SEQ ID NO:42)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYP.

The IMGT accession number of allele *02 of the IGKV1 D-16 gene is V00558. The amino acid sequence is:

(SEQ ID NO:43)
DIQMTQSPSSLSASVGDRVTITCRARQGISSWLAWYQQKPEKAPKSLIYA

ASSLQSGVPSRFSGSGSGTDFTLTISSLQPEDFATYYCQQYNSYP.

The IMGT accession number of the IGKV1-27 gene is X63398. The amino acid sequence is:

(SEQ ID NO:44)
DIQMTQSPSSLSASVGDRVTITCRASQGISNYLAWYQQKPGKVPKLLIYA

ASTLQSGVPSRFSGSGSGTDFTLTISSLQPEDVATYYCQKYNSAP.

There are two alleles of the IGKV1-39 gene. The IMGT accession number of allele *01 of the IGKV1-39 gene is X59315. The amino acid sequence is:

(SEQ ID NO:45)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTP.

The IMGT accession number of allele *02 of the IGKV1-39 gene is X59318. The amino acid sequence is:

(SEQ ID NO:46)
DIQMTQSPSFLSASVGDRVTITCRASQSISSYLNWYQQKPGKAPKLLIYA

ASSLQSGVPSRFSGSGSGTDFTLTISSLQPEDFATYYCQCGYSTP.

The IMGT accession number of the IGKV1D-43 gene is X72817. The amino acid sequence is:

(SEQ ID NO:47)
AIRMTQSPFSLSASVGDRVTITCWASQGISSYLAWYQQKPAKAPKLFIYY

ASSLQSGVPSRFSGSGSGTDYTLTISSLQPEDFATYYCQQYYSTP.

The following potential human heavy chain germline sequences were identified and may provide framework regions for a binding molecule of the invention. More specifically, such molecules may provide a scaffold in which any residue of the human light chain germline CDR not identical to the 9B11 light chain CDR may be changed to the mouse CDR amino acid:

There are two alleles of the IGHV3-21 gene. The IMGT accession number of allele *01 of the IGHV3-21 gene is AB019439. The amino acid sequence is:

(SEQ ID NO:48)
EVQLVESGGGLVKPGGSLRLSCAASGFTFSSYSMNWVRQAPGKGLEWVSS

ISSSSSYIYYADSVKGRFTISRDNAKNSLYLQMNSLRAEDTAVYYCAR.

The IMGT accession number of allele *02 of the IGHV3-21 gene is M99658. The amino acid sequence is:

(SEQ ID NO:49)
EVQLVESGGGLVKPGGSLRLSCAASGFTFSSYSMNWVRQAPGKGLEWVSS

ISSSSSYIYYADSVKGRFTISRDNAKNSLYLQMNSLRAEDTAVYYCAR.

There are two alleles and a pseudogene of the IGHV3-11 gene. The IMGT accession number of allele *01 of the IGHV3-11 gene is M99652. The amino acid sequence is:

(SEQ ID NO:50)
QVQLVESGGGLVKPGGSLRLSCAASGFTFSDYYMSWIRQAPGKGLEWVSY

ISSSGSTIYYADSVKGRFTISRDNAKNSLYLQMNSLRAEDTAVYYCAR.

The IMGT accession number of allele *03 of the IGHV3-11 gene is X92287. The amino acid sequence is:

(SEQ ID NO:51)
QVQLVESGGGLVKPGGSLRLSCAASGFTFSDYYMSWIRQAPGKGLEWVSY

ISSSGSTNYADSVKGRFTISRDNAKNSLYLQMNSLRAEDTAVYYCAR.

There are three alleles of the IGHV3-23 gene. The IMGT accession number of allele *01 of the IGHV3-23 gene is M99660. The amino acid sequence is:

(SEQ ID NO:52)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAK.

The IMGT accession number of allele *02 of the IGHV3-23 gene is J00236. The amino acid sequence is:

(SEQ ID NO:53)
EVQLLESGGGLVQPGGSLRLSCAASGFTFSSYAMSWVRQAPGKGLEWVSA

ISGSGGSTYYGDSVKGRFTISRDNSKNTLYLQMNSLRAEDTAVYYCAK.

The IMGT accession number of allele *03 of the IGHV3-23 gene is U29481. The amino acid sequence is:

(SEQ ID NO:54)
EVQLLESGGGLVQPGGSLRLSCAASGFTFSSYAMSWVRQAPGKGLEWVSV

IYSGGSSTYYADSVKGRFTISRDNSKNTLYLQMNSLRAEDTAVYYCAK.

There are three alleles of the IGHV3-48 gene. The IMGT accession number of allele *01 of the IGHV3-48 gene is M99675. The amino acid sequence is:

(SEQ ID NO:55)
EVQLVESGGGLVQPGGSLRLSCAASGFTFSSYSMNWVRQAPGKGLEWVSY

ISSSSSTIYYADSVKGRFTISRDNAKNSLYLQMNSLRAEDTAVYYCAR.

The IMGT accession number of allele *02 of the IGHV3-48 gene is AB019438. The amino acid sequence is:

(SEQ ID NO:56)
EVQLVESGGGLVQPGGSLRLSCAASGFTFSSYSMNWVRQAPGKGLEWVSY

ISSSSSTIYYADSVKGRFTISRDNAKNSLYLQMNSLRDEDTAVYYCAR.

The IMGT accession number of allele *03 of the IGHV3-48 gene is Z12358. The amino acid sequence is:

(SEQ ID NO:57)
EVQLVESGGGLVQPGGSLRLSCAASGFTFSSYEMNWVRQAPGKGLEWVSY

ISSSGSTIYYADSVKGRFTISRDNAKNSLYLQMNSLRAEDTAVYYCAR.

There are five alleles of the IGHV3-64 gene. The IMGT accession number of allele *01 of the IGHV3-64 gene is M99682. The amino acid sequence is:

(SEQ ID NO:58)
EVQLVESGGGLVQPGGSLRLSCAASGFTFSSYAMHWVRQAPGKGLEYVSA

ISSNGGSTYYANSVKGRFTISRDNSKNTLYLQMGSLRAEDMAVYYCAR.

The IMGT accession number of allele *02 of the IGHV3-64 gene is AB019437. The amino acid sequence is:

(SEQ ID NO:59)
EVQLVESGEGLVQPGGSLRLSCAASGFTFSSYAMHWVRQAPGKGLEYVSA

ISSNGGSTYYADSVKGRFTISRDNSKNTLYLQMGSLRAEDMAVYYCAR.

The IMGT accession number of allele *03 of the IGHV3-64 gene is M77298. The amino acid sequence is:

(SEQ ID NO:60)
EVQLVESGGGLVQPGGSLRLSCSASGFTFSSYAMHWVRQAPGKGLEYVSA

ISSNGGSTYYADSVKGRFTISRDNSKNTLYVQMSSLRAEDTAVYYCVK.

The IMGT accession number of allele *04 of the IGHV3-64 gene is M77299. The amino acid sequence is:

(SEQ ID NO:61)
QVQLVESGGGLVQPGGSLRLSCSASGFTFSSYAMHWVRQAPGKGLEYVSA

ISSNGGSTYYADSVKGRFTISRDNSKNTLYLQMNSLRAEDTAVYYCAR.

The IMGT accession number of allele *05 of the IGHV3-64 gene is M77301. The amino acid sequence is:

(SEQ ID NO:62)
EVQLVESGGGLVQPGGSLRLSCSASGFTFSSYAMHWVRQAPGKGLEYVSA

ISSNGGSTYYADSVKGRFTISRDNSKNTLYVQMSSLRAEDTAVYYCVK.

Each of these germline sequences may be used to provide framework regions for use with one or more 9B11 CDRs.

As used herein, "canonical structures" are conserved hypervariable loop conformations made by different CDRs by which the binding molecule forms the antigen contacts. The assignment of canonical structure classes to a new binding molecule can be achieved using publicly available software.

In another embodiment, the substitution of mouse CDRs into a human variable domain framework is based on the retention of the correct spatial orientation of the mouse variable domain framework by identifying human variable domain frameworks which will retain the same conformation as the mouse variable domain frameworks from which the CDRs were derived. In one embodiment, this is achieved by obtaining the human variable domains from human binding molecules whose framework sequences exhibit a high degree of sequence identity with the murine variable framework domains from which the CDRs were derived. See Kettleborough et al., Protein Engineering 4:773 (1991); Kolbinger et al., Protein Engineering 6:971 (1993) and Carter et al., WO 92/22653.

Preferably the human acceptor binding molecule retains the canonical and interface residues of the donor binding molecule. Additionally, the human acceptor binding molecule preferably has substantial similarity in the length of CDR loops. See Kettleborough et al., Protein Engineering 4:773 (1991); Kolbinger et al., Protein Engineering 6:971 (1993) and Carter et al., WO 92/22653.

In another embodiment, appropriate human acceptor sequences may be selected based on homology to framework regions of the 9B11 binding molecule. For example, the amino acid sequence of the 9B11 binding molecule may be compared to the amino acid sequence of other known binding molecules by, for example, by comparing the FR regions or the variable region sequences of the 9B11 amino acid sequence against a publicly available database of known binding molecules and selecting those sequences with the highest percent identity of amino acids in the variable or FR region, i.e., 80%, 85%, 86%, 87%, 88%, 89%, 90%, 91%, 92%, 93%, 94%, 95%, 96%, 97%, 98%, 99%, 99.5%. In one embodiment, the framework sequence set forth in SEQ ID NO:63 may be used EVQLVESGG GLVKPGGS LRLSCAAS GFAFSSYDM SWVRQAPGKGLEWVSTISSSGS YTYYPDS VKGRFT ISRDNAKNSLYLQMN SLRAEDTA VYYCARL WGAMDYWGQGTLVTVSS(SEQ ID NO:63; (Framework residues are in bold))).

In another embodiment, the framework sequence set forth in SEQ ID NO:64 may be used
DIQMTQ SPSSLSAS VGDRVTITCRASQGLTN DLHWYQQK PGKAPKRLIYY ASQSISGV PSRFSGS GSGTEFTI TISSLQPED FATYYCQQSNSWPFTFG QGT KLEIKR(SEQ ID NO:64; Framework residues are in bold))).

Having identified the complementarity determining regions of the murine donor immunoglobulin and appropriate human acceptor immunoglobulins, the next step is to determine which, if any, residues from these components should be substituted to optimize the properties of the resulting humanized binding molecule. In general, substitution of human amino acid residues with murine should be minimized, because introduction of murine residues increases the risk of the binding molecule eliciting a human-anti-mouse-antibody (HAMA) response in humans. Art-recognized methods of determining immune response can be performed to monitor a HAMA response in a particular patient or during clinical trials. Patients administered humanized binding molecules can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis.

When necessary, one or more residues in the human framework regions can be changed or substituted to residues at the corresponding positions in the murine antibody so as to preserve the binding affinity of the humanized antibody to the antigen. This change is sometimes called "backmutation". Certain amino acids from the human variable region framework residues are selected for back mutation based on their possible influence on CDR conformation and/or binding to antigen. The placement of murine CDR regions with human variable framework region can result in conformational restraints, which, unless corrected by substitution of certain amino acid residues, lead to loss of binding affinity.

In one embodiment, the selection of amino acid residues for backmutation can be determined, in part, by computer modeling, using art recognized techniques. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid may be substituted by the equivalent framework amino acid from the mouse binding molecule when it is reasonably expected that the amino acid: (1) noncovalently binds antigen directly, (2) is adjacent to a CDR region, (3) otherwise interacts with a CDR region (e.g., is within about 3-6 Å of a CDR region as determined by computer modeling), or (4) participates in the VL-VH interface.

Residues which "noncovalently bind antigen directly" include amino acids in positions in framework regions which are have a good probability of directly interacting with amino acids on the antigen according to established chemical forces, for example, by hydrogen bonding, Van der Waals forces, hydrophobic interactions, and the like.

Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk *JMB* 196:901 (1987)). These amino acids are particularly likely to interact with the amino acids in the CDRs and, if chosen from the acceptor, may distort the donor CDRs and reduce affinity. Moreover, the adjacent amino acids may interact directly with the antigen (Amit et al., *Science*, 233:747 (1986), which is incorporated herein by reference) and selecting these amino acids from the donor may be desirable to keep all the antigen contacts that provide affinity in the original binding molecule.

Residues that "otherwise interact with a CDR region" include those that are determined by secondary structural analysis to be in a spatial orientation sufficient to effect a CDR region. In one embodiment, residues that "otherwise interact with a CDR region" are identified by analyzing a three-dimensional model of the donor immunoglobulin (e.g., a computer-generated model). A three-dimensional model, typically of the original donor binding molecule, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 Å of some atom in the CDRs and must contain an atom that could interact with the CDR atoms according to established chemical forces, such as those listed above.

In the case of atoms that may form a hydrogen bond, the 3 Å is measured between their nuclei, but for atoms that do not form a bond, the 3 Å is measured between their Van der Waals surfaces. Hence, in the latter case, the nuclei must be within about 6 Å (3 Å plus the sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact binding molecule, and (2) in a hypothetical molecule consisting of the binding molecule with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an binding molecule, using algorithms known in the art (e.g., Connolly, *J. Appl. Cryst.* 16:548 (1983) and Lee and Richards, *J. Mol. Biol.* 55:379 (1971), both of which are incorporated herein by reference). Framework amino acids may also occasionally interact with the CDRs indirectly, by affecting the conformation of another framework amino acid that in turn contacts the CDRs.

The amino acids at several positions in the framework are known to be capable of interacting with the CDRs in many binding molecules (Chothia and Lesk, supra, Chothia et al., supra and Tramontano et al., J. Mol. Biol. 215:175 (1990), all of which are incorporated herein by reference). Notably, the amino acids at positions 2, 48, 64 and 71 of the light chain and 26-30, 71 and 94 of the heavy chain (numbering according to Kabat) are known to be capable of interacting with the CDRs in many binding molecules. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized binding molecule.

Residues which "participate in the VL-VH interface" or "packing residues" include those residues at the interface between VL and VH as defined, for example, by Novotny and Haber (*Proc. Natl. Acad. Sci. USA*, 82:4592-66 (1985)) or Chothia et al, supra. Generally, unusual packing residues should be retained in the humanized binding molecule if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant binding molecules are produced, one of which has that particular substitution, the other of which does not. Alternative variant binding molecules so produced can be tested in any of the assays described herein for the desired activity, and the preferred binding molecule selected.

Usually the CDR regions in humanized binding molecules are substantially identical, and more usually, identical to the corresponding CDR regions of the donor binding molecule. Although not usually desirable, it is sometimes possible to make one or more conservative amino acid substitutions of CDR residues without appreciably affecting the binding affinity of the resulting humanized binding molecule. By conservative substitutions it is meant combinations such as Gly, Ala; Val, Ile, Leu; Asp, Glu; Asn, Gln; Ser, Thr; Lys, Arg; and Phe, Tyr.

Additional candidates for substitution are acceptor human framework amino acids that are unusual or "rare" for a human immunoglobulin at that position. These amino acids can be substituted with amino acids from the equivalent position of the mouse donor binding molecule or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criterion help ensure that an atypical amino acid in the human framework does not disrupt the binding molecule structure. Moreover, by replacing an unusual human acceptor amino acid with an amino acid from the donor binding molecule that happens to be typical for human binding molecules, the humanized binding molecule may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions. Notably, CDR1 in the variable heavy chain is defined as including residues 26-32.

Additional candidates for substitution are acceptor framework residues that correspond to a rare or unusual donor framework residue. Rare or unusual donor framework residues are those that are rare or unusual (as defined herein) for murine binding molecules at that position. For murine binding molecules, the subgroup can be determined according to Kabat and residue positions identified which differ from the consensus. These donor specific differences may point to somatic mutations in the murine sequence which enhances activity. Unusual residues that are predicted to affect binding are retained, whereas residues predicted to be unimportant for binding can be substituted.

Additional candidates for substitution are non-germline residues occurring in an acceptor framework region. For example, when an acceptor binding molecule chain (i.e., a human binding molecule chain sharing significant sequence identity with the donor binding molecule chain) is aligned to a germline binding molecule chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized binding molecules are usually substantially identical, and more usually, identical to the framework regions of the human binding molecules from which they were derived. Of course, many of the amino acids in the framework region make little or no direct contribution to the specificity or affinity of a binding molecule. Thus, many individual conservative substitutions of framework residues can be tolerated without appreciable change of the specificity or affinity of the resulting humanized binding molecule. Thus, in one embodiment the variable framework region of the humanized binding molecule shares at least 85% sequence identity to a human variable framework region sequence or consensus of such sequences. In another embodiment, the variable framework region of the humanized binding molecule shares at least 90%, preferably 95%, more preferably 96%, 97%, 98% or 99% sequence identity to a human variable framework region sequence or consensus of such sequences. In general, however, such substitutions are undesirable.

In one embodiment, a binding molecule of the invention further comprises at least one backmutation of a human amino acid residue to the corresponding mouse amino acid residue where the amino acid residue is an interface packing residue. "Interface packing residues" include those residues at the interface between VL and VH as defined, for example, by Novotny and Haber, Proc. Natl. Acad. Sci. USA, 82:4592-66 (1985).

In one embodiment, a binding molecule of the invention further comprises at least one backmutation of a human amino acid residue to the corresponding mouse amino acid residue is a canonical residue. "Canonical residues" are conserved framework residues within a canonical or structural class known to be important for CDR conformation (Tramontano et al., J. Mol. Biol. 215:175 (1990), all of which are incorporated herein by reference). Canonical residues include 2, 25, 27B, 28, 29, 30, 33, 48, 51, 52, 64, 71, 90, 94 and 95 of the light chain and residues 24, 26, 27 29, 34, 54, 55, 71 and 94 of the heavy chain. Additional residues (e.g., CDR structure-determining residues) can be identified according to the methodology of Martin and Thorton (1996) J. Mol. Biol. 263:800.

In one embodiment, a binding molecule of the invention further comprises at least one backmutation of a human amino acid residue to the corresponding mouse amino acid residue where the amino acid residue is at a position capable of interacting with a CDR. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs.

Based on CLUSTAL W analysis, several amino acid residues in the human framework were identified for potential substitution, e.g., with corresponding amino acid residues from the 9B11 light chain. These included positions 3, 4, 9, 10, 13, 14, 15, 18, 20, 21, 22, 41, 42, 43, 45, 46, 49, 58, 70, 76, 78, 79, 80, 84, 85, 86, 87, and 100.

In one embodiment, a variable light chain framework of a binding molecule of the invention further comprises at least one substitution of a human amino acid residue to the corresponding mouse amino acid residue selected from the group consisting of: Q3V, (i.e., the Q at position 3 of the CDR-grafted antibody which comprises murine CDRs and human FR regions is mutated to a V, which is the corresponding amino acid residue in the 9B11 antibody (without leader)), Q3L, Q3I, M4L, M4V, M4I, S9A, S9G, S9V, S9L, S9I, S10T, S10Y, A13V, A13L, A13I, S14T, S14Y, VP15, R18S, R18T, R18Y, T20S, T20Y, I21L, I21V, T22S, T22Y, G41H, G41C, K42E, K42D, A43S, A43T, A43Y, K45R, R46L, R46I, R46V, Y49K, Y49R, V58I, V58L, E70D, S76N, S76Q, L78V, L78I, Q79E, Q79D, P80T, P80S, P80Y, A84G, A84A, T85L, T85I, Y86F, Y86W, Y86V, Y86L, Y86I, Y87F, Y87W, Y87V, Y87L, Y87I, Q100A, Q100P, and Q100G.

Based on CLUSTAL W analysis, several amino acid residues in the human framework were identified for potential substitution, e.g., with corresponding amino acid residues from the 9B11 heavy chain. These included positions 3, 10, 19, 40, 42, 44, 49, 76, 78, 84, 88, 93, and 97.

In one embodiment, a variable heavy chain framework of a binding molecule of the invention further comprises at least one substitution of a human amino acid residue to the corresponding mouse amino acid residue selected from the group consisting of: Q3K (i.e., the Q at position 3 of the CDR-grafted antibody which comprises murine CDRs and human FR regions is mutated to a K, which is the corresponding amino acid residue in the 9B11 antibody), Q3H, Q3R, G10D, G10E, R19K, R19H, A40T, A40Y, A40S, G42E, G42D, G44R, G44K, S49A, S49G, S49V, S49L, S49I, K76R, K76H, S78T, S78Y, N84S, N84T, N84Y, A88S, A88T, A88Y, V93L, V93I, V93A, V93G, A97E, and A97D.

The humanized binding molecules preferably exhibit a specific binding affinity for antigen of at least $10^7$, $10^8$, $10^9$ or $10^{10}$ M$^{-1}$. Usually the upper limit of binding affinity of the humanized binding molecules for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized binding molecule having no substitutions (e.g., a binding molecule having donor CDRs and acceptor FRs, but no FR substitutions). In such instances, the binding of the optimized binding molecule (with substitutions) is preferably at least two- to three-fold greater, or three- to four-fold greater, than that of the unsubstituted binding molecule. For making comparisons, activity of the various binding molecules can be determined, for example, by BIACORE (i.e., surface plasmon resonance using unlabelled reagents) or competitive binding assays.

Having conceptually selected the CDR and framework components of humanized binding molecules, a variety of methods are available for producing such binding molecules. Because of the degeneracy of the code, a variety of nucleic acid sequences will encode each binding molecule amino acid sequence. The desired nucleic acid sequences can be produced by de novo solid-phase DNA synthesis or by PCR mutagenesis of an earlier prepared variant of the desired polynucleotide.

Oligonucleotide-mediated mutagenesis is a preferred method for preparing substitution, deletion and insertion variants of target polypeptide DNA. See Adelman et al. (DNA 2:183 (1983)). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

The variable segments of binding molecules produced as described supra (e.g., the heavy and light chain variable regions of chimeric, humanized, or human binding molecules) are typically linked to at least a portion of an immunoglobulin constant region (Fc), typically that of a human immunoglobulin. Human constant region DNA sequences can be isolated in accordance with well known procedures from a variety of human cells, but preferably immortalized B cells (see Kabat et al., supra, and Liu et al., WO87/02671) (each of which is incorporated by reference in its entirety for all purposes). Ordinarily, the binding molecule will contain both light chain and heavy chain constant regions. The heavy chain constant region usually includes CH1, hinge, CH2, CH3, and CH4 regions. A binding molecule described herein include antibodies having all types of constant regions, including IgM, IgG, IgD, IgA and IgE, and any isotype, including IgG1, IgG2, IgG3 and IgG4. The choice of constant region depends, in part, or whether binding molecule-dependent complement and/or cellular mediated toxicity is desired. For example, isotypes IgG1 and IgG3 have complement activity and isotypes IgG2 and IgG4 do not. When it is desired that the binding molecule (e.g., humanized binding molecule) exhibit cytotoxic activity, the constant domain is usually a complement fixing constant domain and the class is typically IgG1. When such cytotoxic activity is not desirable, the constant domain may be, e.g., of the IgG2 class. Choice of isotype can also affect passage of antibody into the brain. Human isotype IgG1 is preferred. Light chain constant regions can be lambda or kappa. The humanized binding molecule may comprise sequences from more than one class or isotype. Binding molecules can be expressed as tetramers containing two light and two heavy chains, as separate heavy chains, light chains, as Fab, Fab' F(ab')2, and Fv, or as single chain binding molecules in which heavy and light chain variable domains are linked through a spacer.

III. Production of Binding Molecules

The present invention features binding molecules having specificity for ILT3, e.g., human ILT3. Such binding molecules can be used in formulating various therapeutic compositions of the invention or, preferably, provide complementarity determining regions for the production of humanized or chimeric binding molecules (described in detail below). The production of non-human monoclonal binding molecules, e.g., murine, guinea pig, primate, rabbit or rat, can be accomplished by, for example, immunizing the animal with ILT3 or with a nucleic acid molecule encoding ILT3. For example, the 9B11 binding molecule was made by placing the gene encoding human ILT3 in an expression vector and immunizing animals. A longer polypeptide comprising ILT3 or an immunogenic fragment of ILT3 or anti-idiotypic binding molecule of ILT3 can also be used. (see, for example, Harlow & Lane, supra, incorporated by reference for all purposes). Such an immunogen can be obtained from a natural source, by peptide synthesis or by recombinant expression. Optionally, the immunogen can be administered, fused or otherwise complexed with a carrier protein, as described below. Optionally, the immunogen can be administered with an adjuvant. The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages. Several types of adjuvants can be used as described below. Complete Freund's adjuvant followed by incomplete adjuvant is preferred for immunization of laboratory animals.

Rabbits or guinea pigs are typically used for making polyclonal binding molecules. Exemplary preparation of polyclonal binding molecules, e.g., for passive protection, can be performed as follows. Animals are immunized with 100 µg ILT3, plus adjuvant, and euthanized at 4-5 months. Blood is collected and IgG is separated from other blood components. Binding molecules specific for the immunogen may be partially purified by affinity chromatography. An average of about 0.5-1.0 mg of immunogen-specific binding molecule is obtained per animal, giving a total of 60-120 mg.

Mice are typically used for making monoclonal binding molecules. Monoclonals can be prepared against a fragment by injecting the fragment or longer form of ILT3 into a mouse, preparing hybridomas and screening the hybridomas for a binding molecule that specifically binds to ILT3. Optionally, binding molecules are screened for binding to a specific region or desired fragment of ILT3 without binding to other nonoverlapping fragments of ILT3. The latter screening can be accomplished by determining binding of a binding molecule to a collection of deletion mutants of a ILT3 peptide and determining which deletion mutants bind to the binding molecule. Binding can be assessed, for example, by Western blot or ELISA. The smallest fragment to show specific binding to the binding molecule defines the epitope of the binding molecule. Alternatively, epitope specificity can be determined by a competition assay in which a test and reference binding molecule compete for binding to ILT3. If the test and reference binding molecule compete, then they bind to the same epitope (or epitopes sufficiently proximal) such that binding of one binding molecule interferes with binding of the other. The preferred isotype for such binding molecules is mouse isotype IgG2a or equivalent isotype in other species. Mouse isotype IgG2a is the equivalent of human isotype IgG1.

In another embodiment, DNA encoding a binding molecule may be readily isolated and sequenced using conventional procedures (e.g., by using oligonucleotide probes that are capable of binding specifically to genes encoding the heavy and light chains of murine binding molecules). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture of binding molecules as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. Transformed cells expressing the desired antibody may be produced in relatively large quantities to provide clinical and commercial supplies of the binding molecule.

Those skilled in the art will also appreciate that DNA encoding binding molecules or fragments thereof (e.g., antigen binding sites) may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. *Immunol. Today* 21:371; Nagy et al. 2002. *Nat. Med.* 8:801; Huie et al. 2001. *Proc. Natl. Acad. Sci. USA* 98:2682; Lui et al. 2002. *J. Mol. Biol.* 315:1063, each of which is incorporated herein by reference. Several publications (e.g., Marks et al. *Bio/Technology* 10:779-783 (1992)) have described the production of high affinity human binding molecules by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad. Sci. USA* 98:3750; or Irving et al. 2001 *J. Immunol. Methods* 248:31. In yet another embodiment, cell surface libraries can be screened for binding molecules (Boder et al. 2000. Proc. Natl. Acad. Sci. USA 97:10701; Daugherty et al. 2000 *J. Immunol. Methods* 243:211. Such procedures provide alternatives to traditional hybridoma techniques for the isolation and subsequent cloning of monoclonal binding molecules.

Yet other embodiments of the present invention comprise the generation of human or substantially human binding molecules in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human binding molecules upon antigen challenge. Another preferred means of generating human binding molecules using SCID mice is disclosed in U.S. Pat. No. 5,811,524 which is incorporated herein by reference. It will be appreciated that the genetic material associated with these human binding molecules may also be isolated and manipulated as described herein.

Yet another highly efficient means for generating recombinant binding molecules is disclosed by Newman, *Biotechnology*, 10: 1455-1460 (1992). Specifically, this technique results in the generation of primatized binding molecules that contain monkey variable domains and human constant sequences. This reference is incorporated by reference in its entirety herein. Moreover, this technique is also described in U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the polypeptides of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or synthetic to provide obtain polypeptides of the present invention.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the binding molecule may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the binding molecule light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In one embodiment, a binding molecule of the invention comprises or consists of an antigen binding fragment of an antibody. The term "antigen-binding fragment" refers to a polypeptide fragment of an immunoglobulin or antibody that binds antigen or competes with intact antibody (i.e., with the intact antibody from which they were derived) for antigen binding (i.e., specific binding). As used herein, the term "fragment" of an antibody molecule includes antigen-binding fragments of antibodies, for example, an antibody light chain (VL), an antibody heavy chain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

In one embodiment, a binding molecule of the invention is an engineered or modified antibody. Engineered forms of antibodies include, for example, minibodies, diabodies, diabodies fused to CH3 molecules, tetravalent antibodies, intra-diabodies (e.g., Jendreyko et al. 2003. J. Biol. Chem. 278: 47813), bispecific antibodies; fusion proteins (e.g., antibody cytokine fusion proteins) or, bispecific antibodies. Other immunoglobulins (Ig) and certain variants thereof are described, for example in U.S. Pat. No. 4,745,055; EP 256, 654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In one embodiment, the modified antibodies of the invention are minibodies. Minibodies are dimeric molecules made up of two polypeptide chains each comprising an ScFv molecule (a single polypeptide comprising one or more antigen binding sites, e.g., a VL domain linked by a flexible linker to a VH domain fused to a CH3 domain via a connecting peptide.

ScFv molecules can be constructed in a VH-linker-VL orientation or VL-linker-VH orientation.

The flexible hinge that links the VL and VH domains that make up the antigen binding site preferably comprises from about 10 to about 50 amino acid residues. An exemplary connecting peptide for this purpose is (Gly4Ser)3 (SEQ ID NO:20) (Huston et al. 1988. Proc. Natl. Acad. Sci. USA 85:5879). Other connecting peptides are known in the art.

Methods of making single chain antibodies are well known in the art, e.g., Ho et al. 1989. Gene 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

Minibodies can be made by constructing an ScFv component and connecting peptide-CH3 component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis.

Diabodies are similar to scFv molecules, but usually have a short (less than 10 and preferably 1-5) amino acid residue linker connecting both V-domains, such that the VL and VH domains on the same polypeptide chain can not interact. Instead, the VL and VH domain of one polypeptide chain interact with the VH and VL domain (respectively) on a second polypeptide chain (WO 02/02781). In one embodiment, a binding molecule of the invention is a diabody fused to at least one heavy chain portion. In a preferred embodiment, a binding molecule of the invention is a diabody fused to a CH3 domain.

Other forms of modified antibodies are also within the scope of the instant invention (e.g., WO 02/02781 A1; U.S. Pat. Nos. 5,959,083; 6,476,198 B1; US 2002/0103345 A1; WO 00/06605; Byrn et al. 1990. Nature. 344:667-70; Chamow and Ashkenazi. 1996. Trends Biotechnol. 14:52).

In one embodiment, a binding molecule of the invention comprises an immunoglobulin constant region. It is known in the art that the constant region mediates several effector functions. For example, binding of the C1 component of complement to binding molecules activates the complement system. Activation of complement is important in the opsonisation and lysis of cell pathogens. The activation of complement also stimulates the inflammatory response and may also be involved in autoimmune hypersensitivity. Further, binding molecules bind to cells via the Fc region, with a Fc receptor site on the binding molecule Fc region binding to a Fc receptor (FcR) on a cell. There are a number of Fc receptors which are specific for different classes of binding molecule, including IgG (gamma receptors), IgE (epsilon receptors), IgA (alpha receptors) and IgM (mu receptors). Binding of binding molecule to Fc receptors on cell surfaces triggers a number of important and diverse biological responses including engulfment and destruction of binding molecule-coated particles, clearance of immune complexes, lysis of binding molecule-coated target cells by killer cells (called antibody-dependent cell-mediated cytotoxicity, or ADCC), release of inflammatory mediators, placental transfer and control of immunoglobulin production.

In one embodiment, effector functions may be eliminated or reduced by using a constant region of an IgG4 binding molecule, which is thought to be unable to deplete target cells, or making Fc variants, wherein residues in the Fc region critical for effector function(s) are mutated using techniques known in the art, for example, U.S. Pat. No. 5,585,097. For example, the deletion or inactivation (through point mutations or other means) of a constant region domain may reduce Fc receptor binding of the circulating modified binding molecule thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or binding molecule flexibility. More generally, those skilled in the art will realize that binding molecules modified as described herein may exert a number of subtle effects that may or may not be readily appreciated. However the resulting physiological profile, bioavailability and other biochemical effects of the modifications, such as tumor localization, biodistribution and serum half-life, may easily be measured and quantified using well know immunological techniques without undue experimentation.

In one embodiment, a binding molecule of the invention can be derivatized or linked to another functional molecule (e.g., another peptide or protein). Accordingly, a binding molecule of the invention include derivatized and otherwise modified forms of the anti-ILT3 binding molecules described herein, including immunoadhesion molecules. For example, a binding molecule of the invention can be functionally linked (by chemical coupling, genetic fusion, noncovalent association or otherwise) to one or more other molecular entities, such as another binding molecule (e.g., a bispecific antibody or a diabody), a detectable agent, a cytotoxic agent, a pharmaceutical agent, and/or a protein or peptide that can mediate association of the binding molecule with another molecule (such as a streptavidin core region or a polyhistidine tag).

One type of derivatized binding molecule is produced by crosslinking two or more binding molecules (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which a binding molecule of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. A binding molecule may also be derivatized with detectable enzymes, such as alkaline phosphatase, horseradish peroxidase, glucose oxidase and the like. When a binding molecule is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding molecule may also be derivatized with biotin, and detected through indirect measurement of avidin or streptavidin binding.

IV. Expression of Binding Molecules

A binding molecule of the invention can be prepared by recombinant expression of immunoglobulin light and heavy chain genes in a host cell. To express a binding molecule recombinantly, a host cell is transfected with one or more recombinant expression vectors carrying DNA fragments encoding the immunoglobulin light and heavy chains of the binding molecule such that the light and heavy chains are expressed in the host cell and, preferably, secreted into the medium in which the host cells are cultured, from which medium a binding molecule can be recovered. Standard recombinant DNA methodologies are used to obtain antibody heavy and light chain genes, incorporate these genes into recombinant expression vectors, and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss, et al.

To express a binding molecule of the invention, DNAs encoding partial or full-length light and heavy chains may be inserted into expression vectors such that the genes are operatively linked to transcriptional and translational control sequences. In this context, the term "operatively linked" means that a binding molecule gene is ligated into a vector such that transcriptional and translational control sequences within the vector serve their intended function of regulating the transcription and translation of the binding molecule gene. In one embodiment, the expression vector and expression control sequences are chosen to be compatible with the expression host cell used. The binding molecule light chain gene and the binding molecule heavy chain gene may be inserted into separate vector or, more typically, both genes are inserted into the same expression vector. The binding molecule genes may be inserted into the expression vector by standard methods (e.g., ligation of complementary restriction sites on the binding molecule gene fragment and vector, or blunt end ligation if no restriction sites are present). Prior to insertion of the binding molecule light or heavy chain sequences, the expression vector may already carry binding molecule constant region sequences. For example, one approach to converting VH and VL sequences to full-length binding molecule genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the binding molecule chain from a host cell. The binding molecule chain gene can be cloned into the vector such that the signal peptide is linked in-frame to the amino terminus of the binding molecule chain gene. The signal peptide can be an immunoglobulin signal peptide or a heterologous signal peptide (i.e., a signal peptide from a non-immunoglobulin protein).

In addition to the binding molecule chain genes, the recombinant expression vectors of the invention carry regulatory sequences that control the expression of the binding molecule chain genes in a host cell. The term "regulatory sequence" includes promoters, enhancers and other expression control elements (e.g., polyadenylation signals) that control the transcription or translation of the binding molecule chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner, et al.

In addition to the binding molecule chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the binding molecule heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express a binding molecule of the invention in either prokaryotic or eukaryotic host cells, expression of binding molecules in eukaryotic cells, and most preferably mammalian host cells, is the most preferred because such eukaryotic cells, and in particular mammalian cells, are more likely than prokaryotic cells to assemble and secrete a properly folded and immunologically active binding molecule.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding binding molecules). See Winnacker, From Genes to Clones, VCH Publishers, N.Y., N.Y. (1987). Eukaryotic cells are actually preferred, because a number of suitable host cell lines capable of secreting heterologous proteins (e.g., intact binding molecules) have been developed in the art, and include CHO cell lines, various Cos cell lines, HeLa cells, myeloma cell lines, or transformed B-cells or hybridomas. Preferably, the cells are nonhuman. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149(1992).

Alternatively, binding molecule-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Preferred mammalian host cells for expressing the recombinant binding molecules of the invention include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding binding molecule genes are introduced into mammalian host cells, binding molecules are produced by culturing the host cells for a period of time sufficient to allow for expression of the binding molecule in the host cells or, more preferably, secretion of the binding molecule into the culture medium in which the host cells are grown. Binding molecules can be recovered from the culture medium using standard protein purification methods.

The vectors containing the polynucleotide sequences of interest (e.g., the binding molecule heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole binding molecules, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure binding molecules of at least about 90 to 95% homogeneity are preferred, and 98 to 99% or more homogeneity most preferred, for pharmaceutical uses.

Host cells can also be used to produce portions of intact binding molecules, such as Fab fragments or scFv molecules. It will be understood that variations on the above procedure are within the scope of the present invention. For example, it may be desirable to transfect a host cell with DNA encoding either the light chain or the heavy chain (but not both) of a binding molecule of this invention. Recombinant DNA technology may also be used to remove some or all of the DNA encoding either or both of the light and heavy chains that is not necessary for binding to ILT3. The molecules expressed from such truncated DNA molecules are also encompassed by a binding molecule of the invention. In addition, bifunctional binding molecules may be produced in which one heavy and one light chain are a binding molecule of the invention and the other heavy and light chain are specific for an antigen other than ILT3 by crosslinking a binding molecule of the invention to a second binding molecule by standard chemical crosslinking methods.

In view of the foregoing, another aspect of the invention pertains to nucleic acid, vector and host cell compositions that can be used for recombinant expression of the binding molecules of the invention. The nucleotide sequence encoding the 9B11 light chain variable region is shown in SEQ ID NO: 10. The CDR1 domain of the VL encompasses nucleotides 130-162, the CDR2 domain encompasses nucleotides 208-228, and the CDR3 domain encompasses nucleotides 325-351 of SEQ ID NO: 10. The nucleotide sequence encoding the 9B11 heavy chain variable region is also shown in SEQ ID NO: 9. The CDR1 domain of the VH encompasses nucleotides 133-162, the CDR2 domain encompasses nucleotides 205-255, and the CDR3 domain encompasses nucleotides 352-372 of SEQ ID NO:9. It will be appreciated by the skilled artisan that nucleotide sequences encoding 9B11-related binding molecule can be derived from the nucleotide sequences encoding the 9B11 LCVR and HCVR using the genetic code and standard molecular biology techniques.

In one embodiment, the invention provides isolated nucleic acids encoding a 9B11-related CDR domain, e.g., comprising an amino acid sequence selected from the group consisting of: SEQ ID NO: 3, SEQ ID NO: 4, SEQ ID NO: 5, SEQ ID NO: 6, SEQ ID NO: 7, and SEQ ID NO: 8.

In still another embodiment, the invention provides an isolated nucleic acid encoding a binding molecule light chain variable region comprising the amino acid sequence of SEQ ID NO: 2, although the skilled artisan will appreciate that due to the degeneracy of the genetic code, other nucleotide sequences can encode the amino acid sequence of SEQ ID NO: 2. The nucleic acid can encode only the VL or can also encode a binding molecule light chain constant region, operatively linked to the VL. In one embodiment, this nucleic acid is in a recombinant expression vector.

In still another embodiment, the invention provides an isolated nucleic acid encoding a binding molecule heavy chain variable region comprising the amino acid sequence of SEQ ID NO: 1, although the skilled artisan will appreciate that due to the degeneracy of the genetic code, other nucleotide sequences can encode the amino acid sequence of SEQ ID NO: 1. The nucleic acid can encode only the VH or can also encode a heavy chain constant region, operatively linked to the VH. For example, the nucleic acid can comprise an IgG1 or IgG2 constant region. In one embodiment, this nucleic acid is in a recombinant expression vector.

The invention also provides recombinant expression vectors encoding a binding molecule heavy chain and/or a binding molecule light chain. For example, in one embodiment, the invention provides a recombinant expression vector encoding:
a) a binding molecule light chain having a variable region comprising the amino acid sequence of SEQ ID NO: 2; and
b) a binding molecule heavy chain having a variable region comprising the amino acid sequence of SEQ ID NO: 1.

In another embodiment, the invention provides a recombinant expression vector encoding:
a) a binding molecule light chain having a variable region comprising the amino acid sequence of SEQ ID NO: 28; and
b) a binding molecule heavy chain having a variable region comprising the amino acid sequence of SEQ ID NO: 29.

In one embodiment, the invention provides a recombinant expression vector encoding:
a) a binding molecule light chain having a variable region comprising the amino acid sequence of SEQ ID NO: 25; and
b) a binding molecule heavy chain having a variable region comprising the amino acid sequence of SEQ ID NO: 26.

In yet another embodiment, the invention provides a recombinant expression vector encoding:
a) a binding molecule light chain having a variable region comprising the amino acid sequence of SEQ ID NO: 25; and
b) a binding molecule heavy chain having a variable region comprising the amino acid sequence of SEQ ID NO: 27.

In another embodiment, the invention provides a recombinant expression vector encoding:
a) a binding molecule light chain having a variable region comprising the amino acid sequence of SEQ ID NO: 33; and
b) a binding molecule heavy chain having a variable region comprising the amino acid sequence of SEQ ID NO: 34.

In yet another embodiment, the invention provides a recombinant expression vector encoding:
a) a binding molecule light chain having a variable region comprising the amino acid sequence of SEQ ID NO: 33; and
b) a binding molecule heavy chain having a variable region comprising the amino acid sequence of SEQ ID NO: 35.

The invention also provides host cells into which one or more of the recombinant expression vectors of the invention have been introduced. Preferably, the host cell is a mammalian host cell.

Still further the invention provides a method of synthesizing a recombinant binding molecule of the invention by culturing a host cell of the invention in a suitable culture medium until a recombinant binding molecule of the invention is synthesized. The method can further comprise isolating the recombinant binding molecule from the culture medium.

V. Uses of the Binding Molecules of the Invention

Given their ability to bind to ILT3, the binding molecules of the invention can be used to detect ILT3 (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting hILT3 in a biological sample comprising contacting a biological sample with a binding molecule of the invention and detecting either the binding molecule bound to hILT3 or unbound binding molecule, to thereby detect hILT3 in the biological sample. The binding molecule is directly or indirectly labeled with a detectable substance to facilitate detection of the bound or unbound binding molecule. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

Alternative to labeling the binding molecule, hILT3 can be assayed in biological fluids by a competition immunoassay utilizing ILT3 standards labeled with a detectable substance and an unlabeled anti-hILT3 binding molecule. In this assay, the biological sample, the labeled ILT3 standards and the anti-hILT3 binding molecule are combined and the amount of labeled ILT3 standard bound to the unlabeled binding molecule is determined. The amount of hILT3 in the biological sample is inversely proportional to the amount of labeled ILT3 standard bound to the anti-hILT3 binding molecule.

An anti-ILT3 binding molecule of the invention can also be used to detect ILT3s from species other than humans, in particular ILT3s from primates (e.g., chimpanzee, baboon, marmoset, cynomolgus and rhesus).

Methods of Downmodulating Immune Responses In Vitro and In Vivo

As described in the appended examples, the binding molecules of the invention can be used as immunoinhibitory compositions in vitro to inhibit immune cell activation, such as an alloimmune response (e.g., an MLC), by cells. In one embodiment, cells are treated with an ILT-3 binding molecule in vitro, e.g., for one, two, three, four, five, six, seven days, e.g., to reduce their state of activation prior to their infusion into a subject.

Accordingly, in one embodiment, the invention provides a method for modulating, e.g., downmodulating, immune cell activation, e.g., an alloimmune response, in vitro. In another embodiment, the invention provides a method of downmodulating immune cell activation in vivo comprising introducing cells treated in vitro with an ILT-3 binding molecule into a subject. Modulation of an alloimmune response can be assayed using art recognized techniques, for example, by measuring the ability of the binding molecule to modulate the proliferative ability of T cells, e.g., in a mixed lymphocyte reaction.

The binding molecules of the invention may also be used to downmodulate the production of inflammatory cytokines, e.g., IL12p40, IL12p70, and TNFα, by DC, e.g., MDDC, in vitro, e.g., prior to introduction into a subject. Downmodulation of inflammatory cytokine production by DC can be assayed, for example, by ELISA.

In another embodiment, the binding molecules of the invention may also be used to downmodulate the upregulation of costimulatory molecules, e.g., CD86, CD80, CD83, and HLA-DR, by DC, e.g., MDDC, in vitro, e.g., prior to introduction into a subject. Downmodulation of the upregulation of costimulatory molecules by DC can be assayed, for example, by FACs analysis.

In yet another embodiment, the binding molecules of the invention may also be used to downmodulate calcium flux in monocytes in vitro, e.g., prior to their introduction into a subject. Calcium flux in monocytes can be measured, for example, by FACs analysis or by calcium-chelation luminescence spectrophotometry. See for example, Rabin, et al. (1999) *J Immunol.* 162:3840-3850, Youn, B. S., et al. (1998) *Blood* 91:3118, and Youn, B. S., et al. (1997) *J. Immunol.* 159:5201, the contents of each of these references is hereby incorporated herein by reference.

In one embodiment, the binding molecules of the invention may be used to upregulate the expression of inhibitory receptors on a cell, such as a dendritic cell, e.g., an immature dendritic cell. Exemplary inhibitory receptors whose expression is upregulated by the binding molecules of the invention include, but are not limited to, CD200R, CD40L and IDO (indolamine).

In one aspect, the invention relates to a method for preventing in a subject, a disease or condition associated with unwanted immune cell activation comprising treating cells in vitro with an ILT-3 binding agent and introducing them into a compatible subject or reintroducing them into the same subject. Subjects at risk for a disease that would benefit from treatment with the claimed agents or methods can be identified, for example, by any or a combination of diagnostic or prognostic assays known in the art. Administration of a prophylactic agent can occur prior to the manifestation of symptoms associated with an unwanted or less than desirable immune response.

Diseases or pathological conditions that would benefit from downmodulating the activity of ILT3 on APC, e.g., monocytes, macrophages, and DC, e.g., MDDC, include situations of tissue, skin and organ transplantation or graft-versus-host disease (GVHD). For example, blockage of immune cell activation results in reduced tissue destruction in tissue transplantation. Typically, in tissue transplants, rejection of the transplant is initiated through its recognition as foreign by immune cells, followed by an immune reaction that destroys the transplant. The cells treated in vitro with an anti-ILT3 binding molecule can be administered alone or in conjunction with another agent which downmodulates immune cell activation, prior to or at the time of transplantation to reduce immune cell activation to the transplant (e.g., hormonal therapy, immunotherapy, e.g., immunosuppressive therapy, antibiotics, and immunoglobulin). Generally, administration of products of a species origin or species reactivity (in the case of binding molecules) that is the same species as that of the patient is preferred. It may also be desirable to block the costimulatory function of other polypeptides. For example, it may be desirable to block the function of B7-1, B7-2, or B7-1 and B7-2 by administering a soluble form of a combination of peptides having an activity of each of these antigens, blocking antibodies against these antigens or blocking small molecules (separately or together in a single composition) prior to or at the time of transplantation. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers or soluble forms of other receptor ligand pairs (e.g., agents that disrupt the interaction between CD40 and CD40 ligand (e.g., anti CD40 ligand antibodies)), antibodies against cytokines, or immunosuppressive drugs.

Moreover, modulation of ILT3, and/or inhibition of costimulatory signals, and/or upregulation of other inhibitory receptors, may also be sufficient to anergize the immune cells, thereby inducing tolerance in a subject. Induction of long-term tolerance by modulating ILT3 may avoid the necessity of repeated administration of these blocking reagents.

Accordingly, the methods of the invention can be used to treat a subject suffering from a disorder, which method comprises contacting a cell from a subject with a binding molecule of the invention such that an immune response is down-modulated. Preferably, the subject is a human subject. Alternatively, the subject can be a mammal expressing ILT3 with which a binding molecule of the invention cross-reacts.

Methods of Upmodulating Immune Responses In Vivo

As described in the appended examples, the binding molecules of the invention can be used as immunostimulatory compositions, e.g., alone or as part of a vaccine, to promote B cell, and/or T cell activation, e.g., either Th1 or Th2 cell activation, in a subject. That is, the binding molecules of the invention can serve as adjuvants used in combination with an antigen of interest to enhance an immune response to that antigen of interest in vivo. For example, to stimulate an antibody or cellular immune response to an antigen of interest (e.g., for vaccination purposes), the antigen and a binding molecules of the invention can be coadministered (e.g., coadministered at the same time in the same or separate compositions, or sequentially in time such that an enhanced immune response occurs). The antigen of interest and the binding molecules can be formulated together into a single pharmaceutical composition or in separate compositions. In a preferred embodiment, the antigen of interest and the binding molecule are administered simultaneously to the subject. Alternatively, in certain situations it may be desirable to administer the antigen first and then the binding molecule or vice versa (for example, in the case of an antigen that naturally evokes a Th1 response, it may be beneficial to first administer the antigen alone to stimulate a Th1 response and then administer a binding molecule, alone or together with a boost of antigen, to shift the immune response to a Th2 response). In preferred embodiments, an ILT3 binding molecule of the invention is administered at the time of priming with antigen, i.e., at the time of the first administration of antigen. For example, day −3, −2, −1, 0, +1, +2, +3. A particularly preferred day of administration of an ILT3 binding molecule of the invention is day −1.

In one embodiment, an ILT-3 binding molecule is administered with an antigen of interest. An antigen of interest is one to which an immune response is desired. For example, one capable of providing protection in subject against challenge by an infectious agent from which the antigen was derived. In another embodiment, the invention pertains to administration of an ILT-3 binding molecule of the invention to increase immune responses without having to administer an antigen.

Exemplary antigens of interest therefore include those derived from infectious agents, wherein an immune response directed against the antigen serves to prevent or treat disease caused by the agent. Such antigens include, but are not limited to, viral, bacterial, fungal or parasite proteins and any other proteins, glycoproteins, lipoprotein, glycolipids, and the like. Antigens of interest also include those which provide benefit to a subject which is at risk for acquiring or which is diagnosed as having a tumor. The subject is preferably a mammal and most preferably, is a human.

Typical antigens of interest may be classified as follows: protein antigens, such as ceruloplasmin and serum albumin; bacterial antigens, such as teichoic acids, flagellar antigens, capsular polysaccharides, and extra-cellular bacterial products and toxins; glycoproteins and glycolipids; viruses, such as animal, plant, and bacterial viruses; conjugated and synthetic antigens, such as proteinhapten conjugates, molecules expressed preferentially by tumors, compared to normal tissue; synthetic polypeptides; and nucleic acids, such as ribonucleic acid and deoxyribonucleic acid. The term "infectious agent," as used herein, includes any agent which expresses an antigen which elicits a host cellular immune response. Non-limiting examples of viral antigens which may be considered useful as include, but are not limited to, the nucleoprotein (NP) of influenza virus and the Gag proteins of HIV. Other heterologous antigens include, but are not limited to, HIV Env protein or its component parts gp120 and gp41, HIV Nef protein, and the HIV Pol proteins, reverse transcriptase and protease. In addition, other viral antigens such as Ebola virus (EBOV) antigens, such as, for example, EBOV NP or glycoprotein (GP), either full-length or GP deleted in the mucin region of the molecule (Yang Z-Y, et al. (2000) Nat Med 6:886-9, 2000), small pox antigens, hepatitis A, B or C virus, human rhinovirus such as type 2 or type 14, Herpes simplex virus, poliovirus type 2 or 3, foot-and-mouth disease virus (FMDV), rabies virus, rotavirus, influenza virus, coxsackie virus, human papilloma virus (HPV), for example the type 16 papilloma virus, the E7 protein thereof, and fragments containing the E7 protein or its epitopes; and simian immunodeficiency virus (SIV) may be used. The antigens of interest need not be limited to antigens of viral origin. Parasitic antigens, such as, for example, malarial antigens are included, as are fungal antigens, bacterial antigens and tumor antigens. Examples of antigens derived from bacteria are those derived from *Bordetella pertussis* (e.g., P69 protein and filamentous haemagglutinin (FHA) antigens), *Vibrio cholerae*, *Bacillus anthracis*, and *E. coli* antigens such as *E. coli* heat Labile toxin B subunit (LT-B), *E. coli* K88 antigens, and enterotoxigenic *E. coli* antigens. Other examples of antigens include *Schistosoma mansoni* P28 glutathione S-transferase antigens (P28 antigens) and antigens of flukes, mycoplasma, roundworms, tapeworms, *Chlamydia trachomatis*, and malaria parasites, e.g., parasites of the genus *plasmodium* or *babesia*, for example *Plasmodium falciparum*, and peptides encoding immunogenic epitopes from the aforementioned antigens.

By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells. The types of tumor antigens and tumor-related antigens include any known or heretofore unknown tumor antigen, including, without limitation, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer.

An infection, disease or disorder which may be treated or prevented by the administration of a composition of the invention includes any infection, disease or disorder wherein a host immune response acts to prevent the infection, disease or disorder. Diseases, disorders, or infection which may be treated or prevented by the administration of the compositions of the invention include, but are not limited to, any infection, disease or disorder caused by or related to a fungus, parasite, virus, or bacteria, diseases, disorders or infections caused by or related to various agents used in bioterrorism, listeriosis, Ebola virus, SARS, small pox, hepatitis A, hepatitis B, hepatitis C, diseases and disorders caused by human rhinovirus, HIV and AIDS, Herpes, polio, foot-and-mouth disease, rabies, diseases or disorders caused by or related to: rotavirus, influenza, coxsackie virus, human papilloma virus, SIV, malaria, cancer, e.g., tumors, and diseases or disorders caused by or related to infection by *Bordetella pertussis, Vibrio cholerae, Bacillus anthracis, E. coli*, flukes, *mycoplasma*, roundworms, tapeworms, *Chlamydia trachomatis*, and malaria parasites, etc.

Immune Responses to Tumor Cells

Regulatory T cells play an important role in the maintenance of immunological self-tolerance by suppressing immune responses against autoimmune diseases and cancer. Accordingly, in one embodiment, upmodulating an immune response would be beneficial for enhancing an immune response in cancer. Therefore, the binding molecules of the invention can be used in the treatment of malignancies, to inhibit tumor growth or metastasis. The binding molecules may be administered systemically or locally to the tumor site.

In one embodiment, modulation of ILT3 function may be useful in the induction of tumor immunity. An ILT3 binding molecule can be administered to a patient having tumor cells (e.g., sarcoma, melanoma, lymphoma, leukemia, neuroblastoma, carcinoma) to overcome tumor-specific tolerance in the subject.

As used herein, the term "neoplastic disease" is characterized by malignant tumor growth or in disease states characterized by benign hyperproliferative and hyperplastic cells. The common medical meaning of the term "neoplasia" refers to "new cell growth" that results as a loss of responsiveness to normal growth controls, e.g., neoplastic cell growth.

As used herein, the terms "hyperproliferative", "hyperplastic", malignant" and "neoplastic" are used interchangeably, and refer to those cells in an abnormal state or condition characterized by rapid proliferation or neoplasia. The terms are meant to include all types of hyperproliferative growth, hyperplastic growth, cancerous growths or oncogenic processes, metastatic tissues or malignantly transformed cells, tissues, or organs, irrespective of histopathologic type or stage of invasiveness. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be either benign, premalignant or malignant.

The terms "neoplasia," "hyperplasia," and "tumor" are often commonly referred to as "cancer," which is a general name for more than 100 disease that are characterized by uncontrolled, abnormal growth of cells. Examples of cancer include, but are not limited to: breast; colon; non-small cell lung, head and neck; colorectal; lung; prostate; ovary; renal; melanoma; and gastrointestinal (e.g., pancreatic and stomach) cancer; and osteogenic sarcoma.

In one embodiment, the cancer is selected from the group consisting of: pancreatic cancer, melanomas, breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues.

Immune Responses to Infectious Agents

Upregulation of immune responses may be in the form of enhancing an existing immune response or eliciting an initial immune response. For example, enhancing an immune response by modulation of ILT3 may be useful in cases of viral infection. As anti-ILT3 binding molecules act to enhance immune responses, they would be therapeutically useful in situations where more rapid or thorough clearance of pathogenic agents, e.g., bacteria and viruses would be beneficial.

As used herein, the term "viral infection" includes infections with organisms including, but not limited to, HIV (e.g., HIV-1 and HIV-2), human herpes viruses, cytomegalovirus (esp. Human), Rotavirus, Epstein-Barr virus, Varicella Zoster Virus, hepatitis viruses, such as hepatitis B virus, hepatitis A virus, hepatitis C virus and hepatitis E virus, paramyxoviruses: Respiratory Syncytial virus, parainfluenza virus, measles virus, mumps virus, human papilloma viruses (for example HPV6, 11, 16, 18 and the like), flaviviruses (e.g. Yellow Fever Virus, Dengue Virus, Tick-borne encephalitis virus, Japanese Encephalitis Virus) or influenza virus.

As used herein, the term "bacterial infections" include infections with a variety of bacterial organisms, including gram-positive and gram-negative bacteria. Examples include, but are not limited to, *Neisseria* spp, including *N. gonorrhea* and *N. meningitidis, Streptococcus* spp, including *S. pneumoniae, S. pyogenes, S. agalactiae, S. mutans; Haemophilus* spp, including *H. influenzae* type B, non typeable *H. influenzae, H. ducreyi; Moraxella* spp, including *M. catarrhalis*, also known as *Branhamella catarrhalis; Bordetella* spp., including *B. pertussis, B. parapertussis* and *B. bronchiseptica; Mycobacterium* spp., including *M. tuberculosis, M. bovis, M. leprae, M. avium, M. paratuberculosis, M. smegmatis; Legionella* spp, including *L. pneumophila; Escherichia* spp, including enterotoxic *E. coli*, enterohemorragic *E. coli*, enteropathogenic *E. coli; Vibrio* spp, including *V. cholera, Shigella* spp, including *S. sonnei, S. dysenteriae, S. flexnerii; Yersinia* spp, including *Y. enterocolitica, Y. pestis, Y. pseudotuberculosis, Campylobacter* spp, including *C. jejuni* and *C. coli; Salmonella* spp, including *S. typhi, S. paratyphi, S. choleraesuis, S. enteritidis; Listeria* spp., including *L. monocytogenes; Helicobacter* spp, including H pylori; *Pseudomonas* spp, including *P. aeruginosa, Staphylococcus* spp., including *S. aureus, S. epidermidis; Enterococcus* spp., including *E. faecalis, E. faecium; Clostridium* spp., including *C. tetani, C. botulinum, C. difficile; Bacillus* spp., including *B. anthracis; Corynebacterium* spp., including *C. diphtheriae; Borrelia* spp., including *B. burgdorferi, B. garinii, B. afzelii, B. andersonii, B. hermsii; Ehrlichia* spp., including *E. equi* and the agent of the Human Granulocytic Ehrlichiosis; *Rickettsia* spp, including *R. rickettsii; Chlamydia* spp., including *C. trachomatis, C. neumoniae, C. psittaci; Leptsira* spp., including *L. interrogans; Treponema* spp., including *T. pallidum, T. denticola, T. hyodysenteriae*. Preferred bacteria include, but are not limited to, *Listeria*, mycobacteria, mycobacteria (e.g., tuberculosis), Anthrax, *Salmonella* and *Listeria monocytogenes*.

In another embodiment, T cells can be removed from a patient, and contacted in vitro with an anti-ILT3 binding molecule, optionally with an activating signal (e.g., antigen plus APCs or a polyclonal antibody) and reintroduced into the patient.

Anti-ILT3 binding molecules may also be used prophylactically in vaccines against various pathogens. Immunity against a pathogen, e.g., a virus, could be induced by vaccinating with a viral protein along with an ILT3 binding molecule (as described above). Alternately, an expression vector which encodes genes for both a pathogenic antigen and an ILT3 binding molecule, e.g., a vaccinia virus expression vector engineered to express a nucleic acid encoding a viral protein and a nucleic acid encoding an ILT3 binding molecule, can be used for vaccination. Pathogens for which vaccines may be useful include, for example, hepatitis B, hepatitis C, Epstein-Barr virus, cytomegalovirus, HIV-1, HIV-2, tuberculosis, malaria and schistosomiasis.

The present invention further encompasses binding molecules conjugated to a diagnostic or therapeutic agent. The binding molecules can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the binding molecule or indirectly, through an intermediate (such as, for example, a linker known in the art) using techniques known in the art. See, for example, U.S. Pat. No. 4,741,900 for metal ions which can be conjugated to binding molecules for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material $I^{125}I^{131}$, $I^{111}$, $In^{99Tc}$.

Further, a binding molecule may be conjugated to a therapeutic moiety such as a cytotoxin, e.g., a cytostatic or cytocidal agent, a therapeutic agent or a radioactive metal ion, e.g., alpha-emitters such as, for example, $^{213}Bi$. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, camustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The present invention is further directed to binding molecule-based therapies which involve administering binding molecules of the invention to an animal, preferably a mammal, and most preferably a human, patient for treating, detecting, and/or preventing one or more of the disclosed diseases, disorders, or conditions. Therapeutic compounds of the invention include, but are not limited to, binding molecules of the invention (including analogs and derivatives thereof as described herein) and anti-idiotypic binding molecules as described herein. The binding molecules of the invention can be used to treat, diagnose, inhibit or prevent diseases, disorders or conditions associated with aberrant activity of ILT3, including, but not limited to, any one or more of the diseases, disorders, or conditions described herein (e.g., binding molecules of the invention may be provided in pharmaceutically acceptable compositions as known in the art or as described herein.

The binding molecules of this invention may be advantageously utilized in combination with other monoclonal or chimeric binding molecules, or with lymphokines or hematopoietic growth factors (such as, e.g., IL-2, IL-3 and IL-7), for example, which serve to increase the number or activity of effector cells which interact with the binding molecules.

The binding molecules of the invention may be administered alone or in combination with other types of treatments, e.g., immunostimulatory treatments or treatments designed to control the proliferation of a target of activated immune cells (e.g., cancer cells or pathogens). Exemplary therapies include e.g., radiation therapy, chemotherapy, hormonal therapy, immunotherapy and anti-tumor agents, antibiotics, and immunoglobulin. Generally, administration of products of a species origin or species reactivity (in the case of binding molecules) that is the same species as that of the patient is preferred. Thus, in a preferred embodiment, human binding molecules, derivatives, analogs, or nucleic acids, are administered to a human patient for therapy or prophylaxis.

A binding molecule of the invention can be administered to a human subject for therapeutic purposes. Moreover, a binding molecule of the invention can be administered to a non-human mammal expressing ILT3 with which the binding molecule cross-reacts (e.g., a primate) for veterinary purposes or as an animal model of human disease. Regarding the latter, such animal models may be useful for evaluating the therapeutic efficacy of binding molecules of the invention (e.g., testing of dosages and time courses of administration).

The present invention is further directed to binding molecule-based therapies which involve administering binding molecules of the invention to an animal, preferably a mammal, and most preferably a human, patient for treating, detecting, and/or preventing one or more of the disclosed diseases, disorders, or conditions. Therapeutic compounds of the invention include, but are not limited to, binding molecules of the invention (including analogs and derivatives thereof as described herein) and anti-idiotypic binding molecules as described herein. The binding molecules of the invention can be used to treat, diagnose, inhibit or prevent diseases, disorders or conditions associated with aberrant activity of ILT3, including, but not limited to, any one or more of the diseases, disorders, or conditions described herein (e.g., binding molecules of the invention may be provided in pharmaceutically acceptable compositions as known in the art or as described herein).

VI. Pharmaceutical Compositions

The binding molecules of the invention can be incorporated into pharmaceutical compositions suitable for administration to a subject. Typically, the pharmaceutical composition comprises a binding molecule of the invention and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the binding molecules of the invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The pharmaceutical compositions can be included in a container, pack, or dispenser together with instructions for administration.

VII. Administration of Binding Molecules of the Invention

Binding molecules of the invention are administered to subjects in a biologically compatible form suitable for pharmaceutical administration in vivo. By "biologically compatible form suitable for administration in vivo" is meant a form of the agent to be administered in which any toxic effects are outweighed by the therapeutic effects of the binding molecule.

Administration of a therapeutically active amount of the therapeutic compositions of the present invention is defined as an amount effective, at dosages and for periods of time necessary to achieve the desired result. For example, a therapeutically active amount of binding molecule may vary according to factors such as the disease state, age, sex, and weight of the individual, and the ability of the binding molecule to elicit a desired response in the individual. Dosage regimens can be adjusted to provide the optimum therapeutic response. For example, several divided doses can be administered daily or the dose can be proportionally reduced as indicated by the exigencies of the therapeutic situation.

The pharmaceutical compositions of the invention may include a "therapeutically effective amount" or a "prophylactically effective amount" of a binding molecule of the invention. A "therapeutically effective amount" refers to an amount effective, at dosages and for periods of time necessary, to achieve the desired therapeutic result. A therapeutically effective amount of the binding molecule may vary according to factors such as the disease state, age, sex, and weight of the individual, and the ability of the binding molecule to elicit a desired response in the individual. A therapeutically effective amount is also one in which any toxic or detrimental effects of the binding molecule are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a binding molecule of the invention is, e.g. from about 0.1-25 mg/kg, from about 1.0-10 mg/kg, from about 0.5-2.5 mg/kg, from about 5-25 mg/kg, from about 1-400 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Additional, non-limiting ranges for a therapeutically or prophylactically effective amount of a binding molecule of the invention is from about 0.0001 to 100 mg/kg, and from about 0.01 to 5 mg/kg (e.g., 0.02 mg/kg, 0.25 mg/kg, 0.5 mg/kg, 0.75 mg/kg, 1 mg/kg, 2 mg/kg, etc.), of the subject body weight. For example, dosages can be 1 mg/kg body weight or 10 mg/kg body weight or within the range of 1-10 mg/kg, preferably at least 1 mg/kg. Doses intermediate in the above ranges are also intended to be within the scope of the invention.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly.

Binding molecules of the invention can be administered on multiple occasions. Intervals between single dosages can be, e.g., daily, weekly, monthly or yearly. Intervals can also be irregular as indicated by measuring blood levels of binding molecule in the patient.

Binding molecules of the invention can optionally be administered in combination with other agents that are effective in treating the disorder or condition in need of treatment (e.g., prophylactic or therapeutic). Preferred additional agents are those which are art recognized and are standardly administered for a particular disorder.

The binding molecule can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, to administer the agent by other than parenteral administration, it may be desirable to coat, or co-administer the agent with, a material to prevent its inactivation.

A binding molecule of the present invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, a binding molecule of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Binding molecules can be co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

When the active compound is suitably protected, as described above, the binding molecule can be orally administered, for example, with an inert diluent or an assimilable edible carrier.

Supplementary active compounds can also be incorporated into the compositions. In certain embodiments, a binding molecule of the invention is coformulated with and/or coadministered with one or more additional therapeutic agents. For example, an anti-ILT3 binding molecule of the invention may be coformulated and/or coadministered with one or more additional antibodies that bind other targets e.g., antibodies that bind other cytokines or that bind cell surface molecules. Such combination therapies may advantageously utilize lower dosages of the administered therapeutic agents, thus avoiding possible toxicities or complications associated with the various monotherapies.

The present invention further encompasses binding molecules conjugated to a diagnostic or therapeutic agent. A binding molecule can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the binding molecule or indirectly, through an intermediate (such as, for example, a linker known in the art) using techniques known in the art. See, for example, U.S. Pat. No. 4,741,900 for metal ions which can be conjugated to binding molecules for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material $I^{125}$ $I^{131}$, $I^{111}$, $In^{99Tc}$.

Further, a binding molecule may be conjugated to a therapeutic moiety such as a cytotoxin, e.g., a cytostatic or cytocidal agent, a therapeutic agent, a radioactive metal ion, e.g., alpha-emitters such as, for example, $^{213}Bi$, biological toxins, prodrugs, peptides, proteins, enzymes, viruses, lipids, biological response modifiers, pharmaceutical agents, immunologically active ligands (e.g., lymphokines or other antibodies). In another embodiment, a binding molecule of the invention can be conjugated to a molecule that decreases vascularization of tumors. In other embodiments, the disclosed compositions may comprise binding molecules of the invention coupled to drugs or prodrugs. Still other embodiments of the present invention comprise the use of binding molecules of the invention conjugated to specific biotoxins or their cytotoxic fragments such as ricin, gelonin, pseudomonas exotoxin or diphtheria toxin. The selection of which conjugated or unconjugated binding molecule to use will depend on the type and stage of cancer, use of adjunct treatment (e.g., chemotherapy or external radiation) and patient condition. It will be appreciated that one skilled in the art could readily make such a selection in view of the teachings herein.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carnustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

This invention is further illustrated by the following examples, which should not be construed as limiting. The contents of all references, patents and published patent applications cited throughout this application, as well as the Figures, are incorporated herein by reference.

EXAMPLES

Example 1

Isolation and Purification of 9B11

The gene encoding ILT3 was cloned and used to immunize mice for generation of anti-ILT3 monoclonal antibodies. The 9B11 antibody is an IgG1 antibody.

The 9B11 antibody was purified as follows:
1. Washed 20 ml Protein G (Pharmacia HR 10/30) with 5CV of dPBS
2. Loaded 1 L (run 1) or 2 L (run 2) of mouse anti-human ILT3 supernatant
3. Washed with 10 CV of dPBS
4. Eluted with 100 mM Citrate, pH 2.8 directly into 1 M Tris (20-25% v: v)
5. Stripped with 100 mM Citrate, pH 2.8, 0.3 M NaCl The 9B11 antibody was shown to cross-react to cynomolgus monkey and baboon monocytes.

Example 2

Dendritic Cells Treated In Vitro with 9B11 have Lower Expression of Cell Surface Co-Stimulatory Molecules MDDC were derived in the presence of either IL-10 or anti-ILT3 mAbs (5A1, 9B11, or 9G3). Immature and mature dendritic cells were used as controls. In addition MDDC were also derived in the presence of TRx1 as a negative control. The results are shown in FIG. 1 which demonstrates that MDDC differentiated in the presence of 9B11 have lower expression of cell surface co-stimulatory molecules, such as CD86, CD80, CD83 and HLA-DR as measured by flow cytometry.

Figure 2:
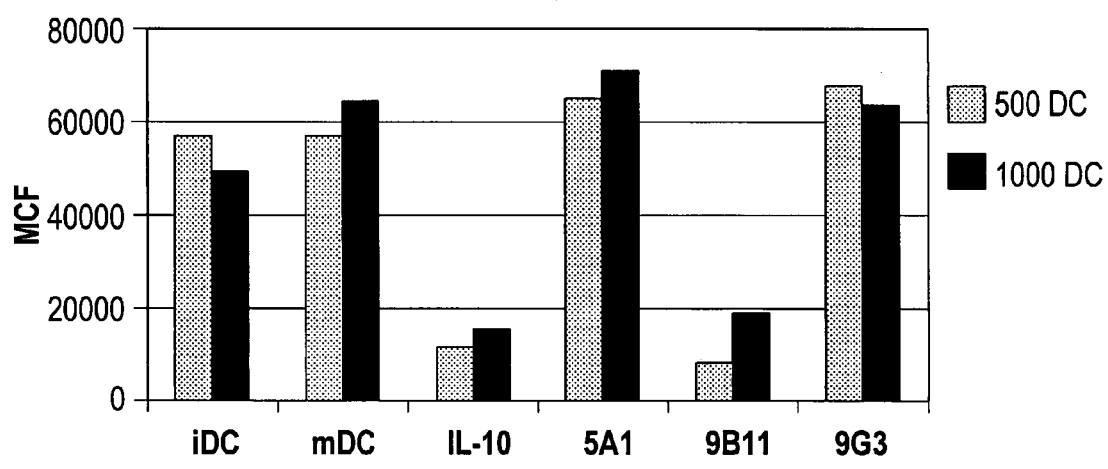
FIG. 2 is a graph demonstrating that MDDCs were unable to generate an allogeneic T cell response in a mixed lymphocyte reaction.
Figure 3A:
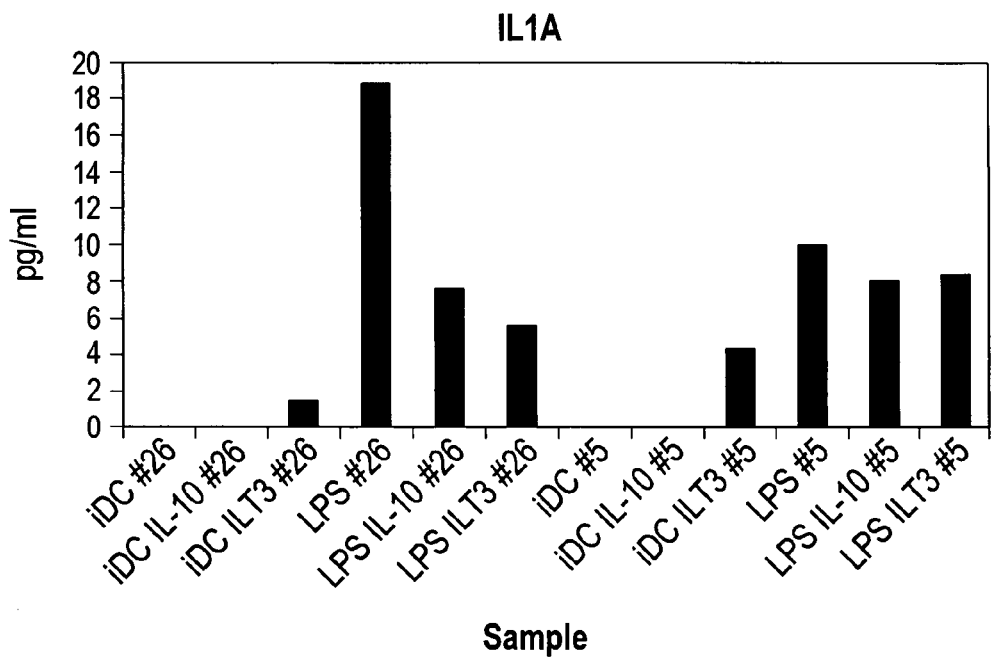
FIG. 3A shows production of IL-1α.
Figure 3B:
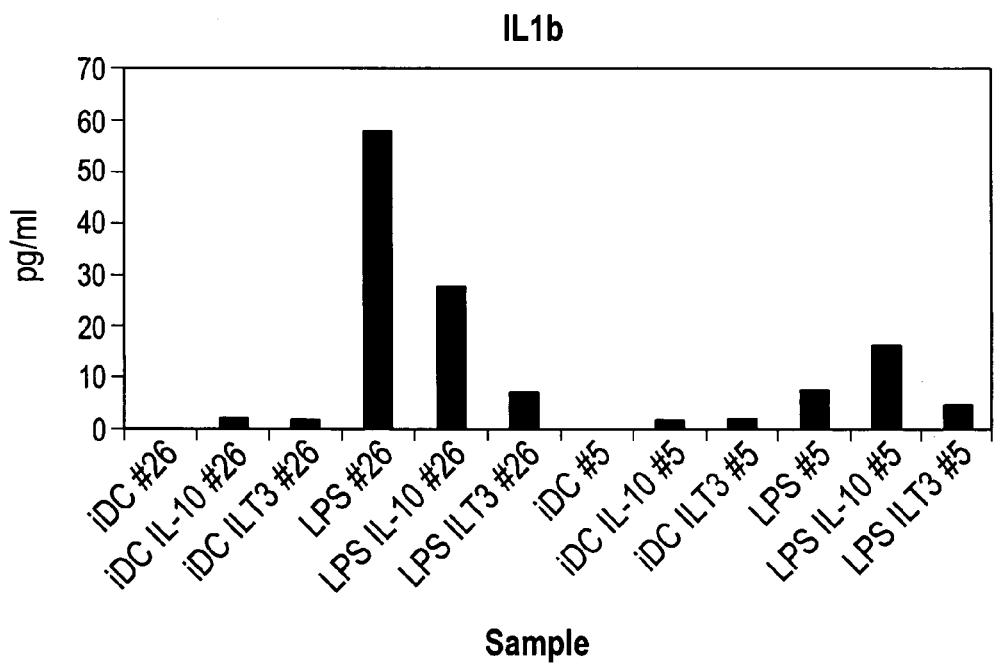
FIG. 3B shows production of IL-1β.
Figure 3C:
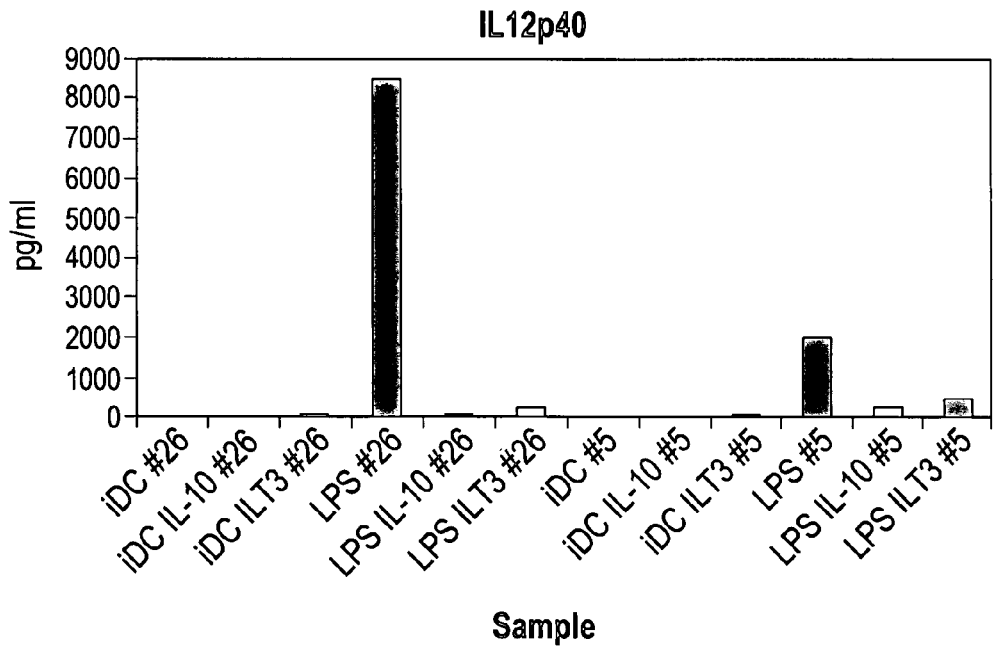
FIG. 3C shows production of IL-12p40.
Figure 3D:
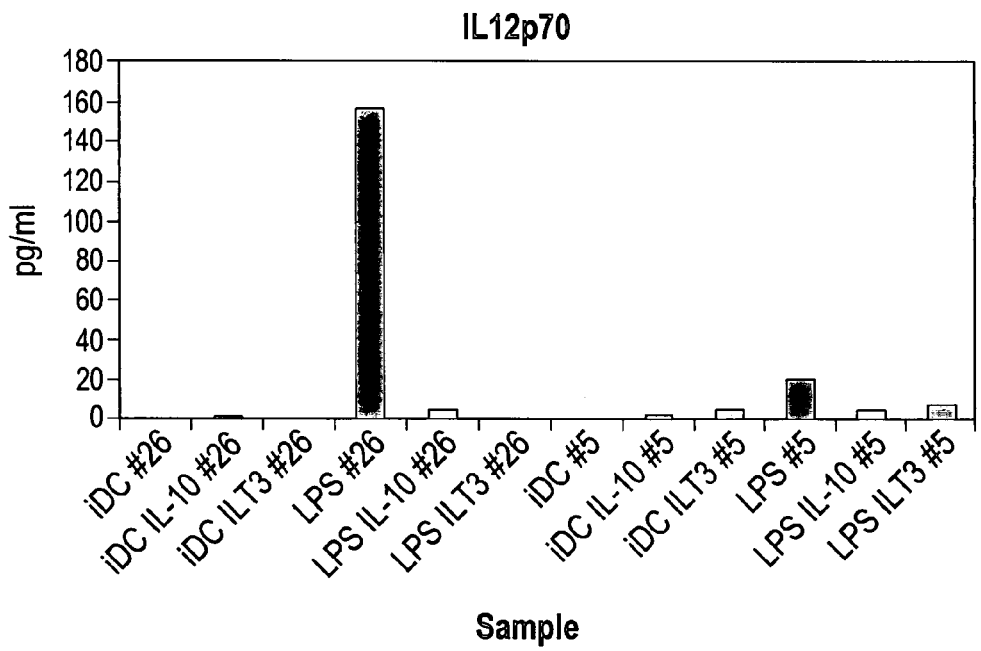
FIG. 3D shows production of IL-12p70.
Figure 3E:
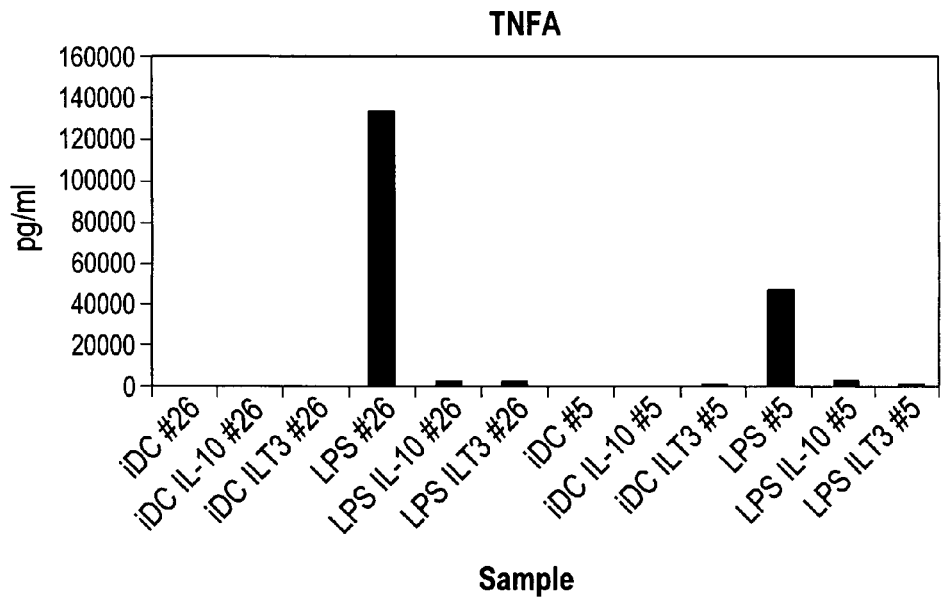
FIG. 3E shows production of TNFα.

As shown above, cells that are differentiated in the presence of 9B11 demonstrate a decreased cell surface expression pattern of costimulatory molecules. Therefore, it is likely that these cells will be unable to generate an allogenic response of T cells in a mixed lymphocyte reaction. As shown in FIG. 2, MDDCs differentiated in the presence of 9B11 result in anergic T cell stimulation in a mixed lymphocyte reaction. DCs were added at either 500 or 1000 cells to $2 \times 10^5$ T cells. The cells were stimulated for 3 days prior to the addition of $^3$H-thymidine.

Furthermore, MDDCs derived in the presence of 9B11 are unable to produce IL-12, TNF-α or IL-1a when stimulated with LPS. Monocytes were treated with GM-CSF and IL-4 on days 0 and 3. IL-10 or ILT3 (9B11; 10 µg/ml) was added on day 0 and 3. On day 5 cells were washed and LPS (5 µg/ml) and were added to the mature cultures. Supernatant fluid was harvested 48 hours after the addition of LPS. Cytokines were measured by ELISA (Pierce Endogen). Two different monocyte donors were used (donor #26 and donor #5) (FIG. 3).

Figure 4:
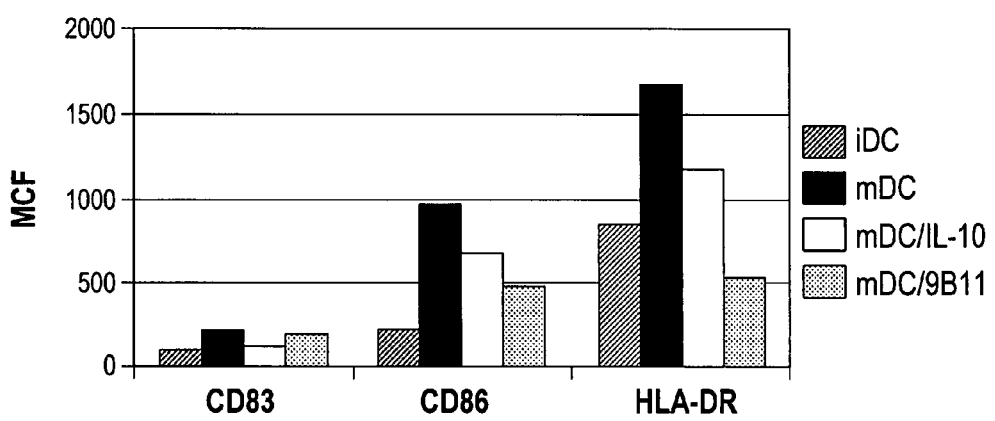
FIG. 4 is a graph demonstrating that freshly isolated blood dendritic cells incubated with 9B11 were unable to fully upregulate the expression of co-stimulatory molecules when a cocktail of cytokines (IL-6, IL-10, TNFα, and PGE) are used to mature the cells.
Figure 5A:
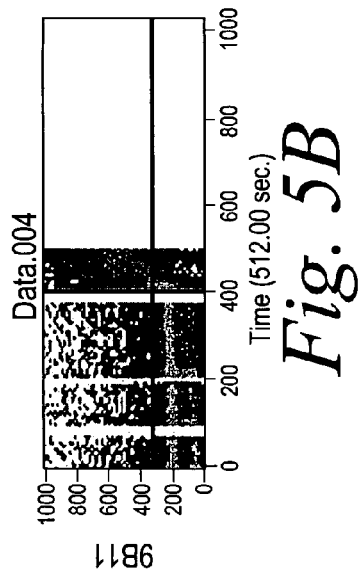
FIG. 5A shows the results obtained with control IgG and IgM antibodies.
Figure 5B:
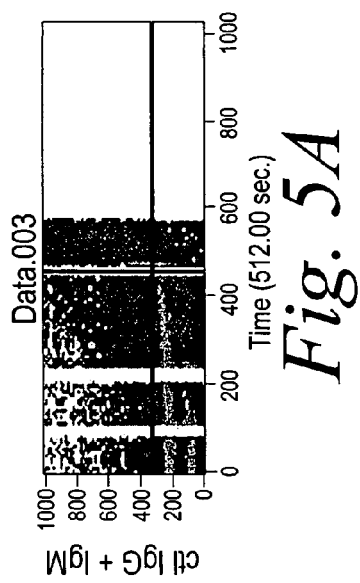
FIG. 5B shows the results achieved with the 9B11 antobody.
Figure 5C:
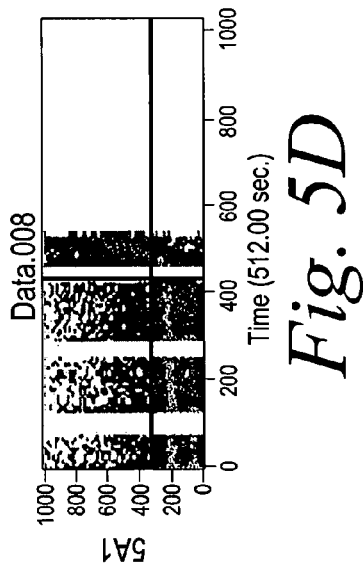
FIG. 5C shows the results obtained with the 9G3 antibody.
Figure 5D:
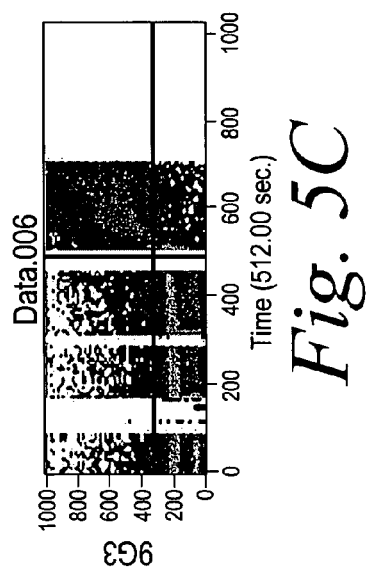
FIG. 5D shows thw reults obtained with the 5A1 antibody.
Figure 5E:
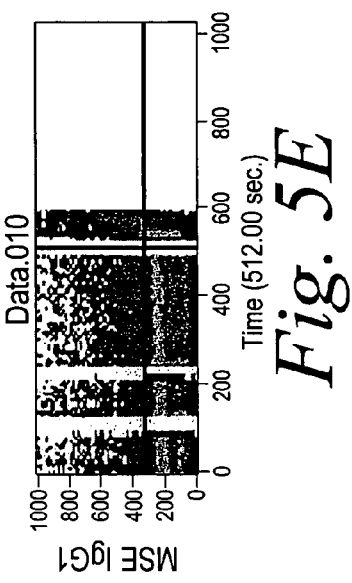
FIG. 5E shows the reults obtained with a mouse IgG1 antibody.

Freshly isolated blood dendritic cells incubated with 9B11 were unable to fully upregulate the expression of co-stimulatory molecules when a cocktail of cytokines (IL-6, IL-1 beta, TNF-alpha, and PGE) was used to mature the cells. Freshly isolated blood dendritic cells were incubated with 9B11 24 hours prior to the addition of the maturation cocktail. The cells were phenotyped 48 hours later to determine if treatment with 9B11 results in decreased expression of co-stimulatory molecules. As shown in FIG. 4, treatment of monocytes with 9B11 resulted in decreased expression of both CD86 and HLA-DR.

9B11 also inhibits $Ca^{+2}$ flux in monocytes induced by the activating immunoreceptor tyrosine-based activation motif (ITAM), CD32. Monocytes were treated with anti-CD32 followed by a goat anti-mouse IgG, IgM to cross-link, which will result in significant Ca+2 flux. However, incubation with 9B11 prior to the addition of CD32 and cross-linking resulted in decreased Ca+2 flux by these monocytes. This was specific for the ILT3 antibodies as an isotype control (mouse IgG1) resulted in less inhibition of Ca+2 flux (FIG. 5).

Intracellular calcium flux studies using flow cytometry analysis was performed as described by Rabin, et al. (*J Immunol.* (1999)162:3840-3850). Briefly, monocyte-derived dendritic cells ($2 \times 10^7$) were suspended in HBSS-HEPES (HBSS supplemented with 10 mM HEPES, $C^{a++}$, $Mg^{++}$, and 1% fetal calf serum). Indo-1 and pleuronic detergent (Molecular Probes, Eugene, Oreg.) were added at final concentrations of 5 µM and 300 µg/mL, respectively. The cell suspension was incubated at 30° C. for 45 minutes with gentle agitation. Cells were then washed twice with the HBSS-HEPES, stained with anti-CD1a$^+$, and washed again. Calcium flux for CD1a+dendritic cells was performed using a FACSVantage flow cytometer (Becton Dickinson) equipped with an argon laser tuned to 488 nM and a krypton laser tuned to 360 nM. Indo-1 fluorescence was analyzed at 390/20 nM and 530/20 nM for bound and free calcium, respectively. Before stimulation, cell suspensions were warmed at 37° C. for 3 minutes. The CD1a$^+$ cell population was gated, and baseline fluorescent ratios were collected for 30 seconds. Cells were then stimulated with either fMLP ($10^5$ M), T-20 peptide ($10^5$ M), or F-peptide ($10^5$ M) followed by fMLP ($10^8$ M). Collections continued until calcium flux returned to basal levels. Changes in Indo-1 fluorescence were expressed as the ratio of bound to free intracellular calcium, and scattergrams represented the entire CD1a+ cell population at the time of stimulation. Data analysis was performed using Flowjo software (Tree Star, San Carlos, Calif.).

Example 3

Dendritic Cells Treated In Vitro with 9B11 have Higher Expression of Cell Surface Inhibitory Receptors 9B11 was also shown to upmodulate the expression of inhibitory receptors, e.g., receptors that generate a negative inhibitory in a cell. Monocytes were isolated using magnetic bead separation technology. The monocytes were treated every other day with 9B11, GM-CSF and IL4. On day 5, a portion of these cells were matured using IL1b, IL6, TNFα, and PGE2. Cells were incubated for a further seven days and then RNA was prepared from immature dendritic cells (iDC) (cells not treated with IL1b, IL6, TNFα, and PGE2) and mature dendritic cells (mDC). The RNA was used to generate cDNA for QPCR. The data is expressed relative to the housekeeping gene 18sRNA. A mouse IgG1 was used as an isotype control and both antibodies were used at a concentration of 10 µg/ml.

The results show that the culturing of monocytes such that they develop into dendritic cells in the presence of an ILT3 binding molecule causes some inhibitory molecules to upregulate. IDO (indolamine) is extremely overexpressed in ILT3 binding molecule treated cells. This molecule is associated with the generation of tolerance. Tolergenic dendritic cells have also been shown to express CD200R and have been shown to be tolergenic in vivo. CD200R and CD40L were also elevated in ILT3 binding molecule treated cells compared to isotype controls, and although 9B111 treatment increased expression of FCGRIIb and FCGRIIa, all of the samples had equal expression of FCGRIIa compared to FCGRIIb. The effect is specific to immature DC, as the expression of the same receptors on mature DC is no different from isotype control.

Example 4

In Vivo Characterization of 9B11

Rhesus macaques were immunized with 9B11 during the priming phase e.g., at days −1, 0, and +1, of a vaccination protocol using *Mycobacterium tuberculosis* as antigen. Subsequent challenge with antigen at day +18 resulted in exacerbation of a cutaneous DTH response. These results indicate that 9B11 acts as an adjuvant useful in enhancing immune responses (e.g., in the case of infection and or malignancy) with less associated morbidity compared to existing adjuvants.

Example 7

Preparation of a Chimeric anti-ILT3 Binding Molecule

The 9B11 variable light chain region was grafted to a human light chain constant region using conventional molecular biological techniques. The IgG1 light chain constant region was used. The amino acid sequence of the complete chimeric light chain GITR binding molecule is shown below:

(SEQ ID NO:25)
DIVLTQSPATLSVTPGDSVSLSCRASQGLTNDLHWYQQKPHESPRLLIKY

ASQSISGIPSRFSGSGSGTDFTLTINSVETEDFGVFFCQQSNSWPFTFGA

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

The 9B11 variable heavy chain was also grafted to a human heavy chain constant region using conventional molecular biological techniques. The IgG1 heavy chain constant region was used. The amino acid sequence of the complete chimeric heavy chain ILT3 binding molecule is shown below (also referred to as "Gly"):

(SEQ ID NO:26)
EVKLVESGGDLVKPGGSLKLSCAASGFAFSSYDMSWVRQTPEKRLEWVAT

ISSSGSYTYYPDSVKGRFTISRDNARNTLYLQMSSLRSEDTALYYCERLW

GAMDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK.

Since the amino acid sequence NX(S/T) is a putative consensus sequence for a glycosylation site which may affect the production of the binding molecule, and IgG1 constant region of the 9B11 heavy chain has the sequence NST, a second version of the heavy chain constant region was prepared to conservatively substitute a glutamine for an asparagine at amino acid residue 296 (bolded and underlined above) of SEQ ID NO:27. Accordingly, a second human constant region was grafted to the 9B11 heavy chain variable region.

The amino acid sequence of the complete chimeric heavy chain ILT3 binding molecule is shown below (also referred to as "Agly"):

(SEQ ID NO:27)
EVKLVESGGDLVKPGGSLKLSCAASGFAFSSYDMSWVRQTPEKRLEWVAT

ISSSGSYTYYPDSVKGRFTISRDNARNTLYLQMSSLRSEDTALYYCERLW

GAMDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK.

Example 8

Preparation of Humanized Forms of the 9B11 Anti-ILT3 Binding Molecule

The CDR homology based strategy described in Hwang et al. (2005) *Methods* (36) 35-42 was used to humanize 9B11. The heavy and light chain amino acid sequences were blasted using a publicly available database, and the results indicated that 9B11 had a 1-3 heavy chain canonical structure and a 2-1-1 light chain canonical structure. From this, all germ line kappa chain V genes with a 2-1-1 canonical structure in the IMGT database were compared with the 9B11 antibody sequence. The same was done for the heavy chain where all 1-3 germ line heavy chain V genes were compared to the 9B11 amino acid sequence. Only the CDR sequences were compared and the frameworks were selected based on which germline sequences had the most matches in the CDRs. (see alignments below).

For the light chain, the 1-17*01 sequence had 15 matches in the CDRs and was selected. The JκC3 J gene segment sequence has the most matches, however, the Jκ2 J gene sequence (GQGTKLEIKR) (SEQ ID NO:19) may also be used.

4/35 Light Chain V Genes with 2-1-1 Canonical Structure IMGT

| Gene Name | CDR1 | CDR2 | CDR3 | IDs |
|---|---|---|---|---|

(CDR1, CDR2 and CDR3 disclosed as residues 24-34, 50-56, and 89-95 of SEQ ID NOS 38, 39, 40, 42, 43, 36, 44, 45, and 47, respectively, in order of appearance).

| Gene Name | CDR1 | CDR2 | CDR3 | IDs |
|---|---|---|---|---|
| IGKV1-6 | RASQGIRNDLG...... | AASSLQS....... | LQDYNYP.. | 12 |
| IGKV1-9 | RASQGISSYLA...... | AASTLQS....... | QQLNSYP.. | 14 |
| IGKV1-12 | RASQGISSWLA...... | AASSLQS....... | QQANSFP.. | 14 |
| IGKV1-16 | RASQGISSWLA...... | AASSLQS....... | QQYNSYP.. | 14 |
| IGKV1D-16 | RARQGISSWLA...... | AASSLQS....... | QQYNSYP.. | 13 |
| IGKV1-17 | RASQGIRNDLG...... | AASSLQS....... | LQHNSYP.. | 15 |
| IGKV1-27 | RASQGISNYLN...... | AASTLQS....... | QKYNSAP.. | 14 |
| IGKV1-39 | RASQSISSYLN...... | AASSLQS....... | QQSYSTP.. | 13 |
| IGKV1D-43 | WASQGISSYLA...... | YASSLQS....... | QQYYSTP.. | 13 |

(CDR1, CDR2 and CDR3 disclosed below as residues 44-54, 70-76, and 109-115 of SEQ ID NO:2).

| | | | | |
|---|---|---|---|---|
| 9B11 | RASQGLTNDLH...... | YASQSTS....... | QQSNSWP | |

All germ line light chain kappa chain V genes with a 2-1-1 canonical structure in the IMGT database were compared with the 9B11 antibody sequence. The same was done for the heavy chain where all 3-1 germ line heavy chain V genes were compared to the 9B11 amino acid sequence Using this methodology one version of the light chain can be made made:

(SEQ ID NO:28)
DIQMTQSPSSLSASVGDRVTITC*RASQGLTNDLH*WYQQKPGKAPKRLIYY

*ASQSISGVPSRFSGSGSGTEFTLTISSLQPEDFATYYCQQSNSWPFT*FGQ

GTKLEIK (the CDRs are italicized)

A number of heavy chain germline sequences had 16 matches to the 9B11 antibody, however, 3-21*01 was selected because the S at the start of CDR 2 is most similar (conservative amino acid substututin) to the T in the chimeric sequence. In addition, the framework of 3-21*01 ends with CAR as opposed to CAK or CAR1 in the other heavy chain germline sequences with 16 matches.

For the J gene segment of the heavy chain, JH4 had the most matches and was therefore, selected. The amino acid sequences are then reverse translated and primers corresponding to the desired nucleotide sequence are obtained from IDT (Coralville, Iowa).

Heavy Chain V Genes with 1-3 Canonical Structures

| IMGT Gene Name | CDR1 | CDR2 | IDs |
|---|---|---|---|
| (CDR1 and CDR2 disclosed as residues 31-35, and 50-66 of SEQ ID NOS 50, 48, 52, 53, 55, and 57, respectively, in order of appearance). | | | |
| IGHV3-11 | DYYMS..... | YISSSGSTTYYADSVKG | 16 |
| IGHV3-21 | SYSMN..... | SISSSSSYIYYADSVKG | 16 |
| IGHV3-23-1 | SYAMS..... | AISGSGGSTYYADSVKG | 16 |
| IGHV3-23-2 | SYAMS..... | AISGSGGSTYYGDSVKG | 16 |
| IGHV3-48 | SYSMN..... | YISSSSSTIYYADSVKG | 15 |
| IGHV3-48-3 | SYEMN..... | YISSSGSTIYYADSVKG | 16 |
| (CDR1 and CDR2 disclosed below as residues 50-54 and 69-85, of SEQ ID NO:1). | | | |
| 9B11 | SYDMS..... | TISSSGSYTYYPDSVKG | |

Using this methodology one version of the heavy chain can be made:

(SEQ ID NO:29)
EVQLVESGGGLVKPGGSLRLSCAAS*GFAFSSYDMS*WVRQAPGKGLEWVS*T*

*ISSSGSYTYYPDSVK*GRFTISRDNAKNSLYLQMNSLRAEDTAVYYCAR*LW*

GAMDYWGQGTLVTVSS.

A CLUSTAL W (1.82) multiple sequence alignment (using a Blosum scoring matrix with a gap penalty of 10) of the 9B11 light chain variable region (residues 21-127 of SEQ ID NO:2 are shown below) and the 1-17*01 germline light chain sequence (SEQ ID NO:36) was also performed. The results are presented below:

```
9B11     DIVLTQSPATLSVTPGDSVSLSCRASQGLTNDLHWYQQKP
1-17*01  DIQMTQSPSSLSASVGDRVTITCRASQGIRNDLGWYQQKP
         ** :****::**.: ** *:::******: *** ******

9B11     HESPRLLIKYASQSISGIPSRFSGSGSGTDFTLTINSVETEDFGVFFCQQSNSWPFTFGA
1-17*01  GKAPKRLIYAASSLQSGVPSRFSGSGSGTEFTLTISSLQPEDFATYYCLQHNSYP-----
          ::*: **  **.  **:***********:*****.*::.***..::* * **:*

9B11     GTKLEIK
1-17*01  -------
```

Based on the CLUSTAL W analyses, several amino acid residues in the human framework were identified for potential substitution with amino acid residues corresponding to the 9B11 framework residues in the humanized 9B11 light chain. Specifically, the Q at position 3, the M at position 4, the S at position 9, the S at position 10, the A at position 13, the S at position 14, the V at position 15, the R at position 18, the T at position 20, the I at position 21, the T at position 22, the G at position 41, the K at position 42, the A at position 43, the K at position 45, the R at position 46, the Y at position 49, the V at position 58, the E at position 70, the S at position 76, the L at position 78, the Q at position 79, the P at position 80, the A at position 84, the T at position 85, the Y at position 86, the Y at position 87, and the Q at position 100.

Similarly, a CLUSTAL W (1.82) multiple sequence alignment (using a Blosum scoring matrix with a gap penalty of 10) of the 9B11 heavy chain variable region (residues 20-117 of SEQ ID NO:1 are shown below) and the germline heavy chain proteins with a 3-21*01 amino acid sequence (SEQ ID NO:8) was also performed. The results are presented below:

```
9B11      EVKLVESGGDLVKPGGSLKLSCAASGFAFSSYDMSWVRQTPEKRLEWVATISSSGSYTYY
3-21-01   EVQLVESGGGLVKPGGSLRLSCAASGFTFSSYSMNWVRQAPGKGLEWVSSISSSSSYIYY
          **:******.********:*********:****.*.****:* * ****::****.** **

9B11      PDSVKGRFTISRDNARNTLYLQMSSLRSEDTALYYCER
3-21-01   ADSVKGRFTISRDNAKNSLYLQMNSLRAEDTAVYYCAR
          .**************:*:*****.***:****:*** *
```

Based on the CLUSTAL W analyses, several amino acid residues in the human framework were identified for potential substitution with amino acid residues corresponding to the 9B11 framework residues in the humanized 9B11 heavy chain.

Specifically, the Q at position 3, the G at position 10, the R at position 19, the A at position 40, the G at position 42, the G at position 44, the S at position 49, the K at position 76, the S at position 78, the N at position 84, the A at position 88, the V at position 93, and/or the A at position 97.

Based on the above, two humanized full-length 9B11 binding molecules can be made having the following humanized heavy and light chain combinations:

Full-length Version 1 (Hu9B11-Gly)—humanized (Hu) 9B11 Light chain (L)/humanized Heavy chain and comprising a constant region having an N ("Gly")

Full-length Version 2 (Hu9B11-Agly)—humanized (Hu) 9B11 Light chain (L)/humanized Heavy chain and comprising a constant region having an A ("Agly")

The amino acid sequence of the glycosylated IgG1 heavy chain constant region that was used to make the full-length binding molecules is shown below:

(SEQ ID NO:30)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKYNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

The amino acid sequence of the aglycosylated IgG1 heavy chain constant region that was used to make the full-length binding molecules is shown below:

(SEQ ID NO:31)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

The amino acid sequence of the IgG1 light chain constant region that was used to make the full-length binding molecules is shown below:

(SEQ ID NO:32)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

The complete amino acid sequence of the humanized 9B11 light chain is shown below:

(SEQ ID NO:33)
DIQMTQSPSSLSASVGDRVTITCRASQGLTNDLHWYQQKPGKAPKRLIYY

ASQSISGVPSRFSGSGSGTEFTLTISSLQPEDFATYYCQQSNSWPFTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

The leader sequence set forth in SEQ ID NO:21 may optionally be included.

The complete amino acid sequences of the humanized 9B11 heavy chain versions Hu9B11-Gly and Hu9B11-Agly are shown below:

Hu9B11-Gly (SEQ ID NO:34)

EVQLVESGGGLVKPGGSLRLSCAASGFAFSSYDMSWVRQAPGKGLEWVST

ISSSGSYTYYPDSVKGRFTISRDNAKNSLYLQMNSLRAEDTAVYYCARLW

GAMDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK;

and

Hu9B11-Agly (SEQ ID NO:35)

EVQLVESGGGLVKPGGSLRLSCAASGFAFSSYDMSWVRQAPGKGLEWVST

ISSSGSYTYYPDSVKGRFTISRDNAKNSLYLQMNSLRAEDTAVYYCARLW

GAMDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

The leader sequence set forth in SEQ ID NO:22 may optionally be included.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. An isolated antibody that specifically binds ILT3, or an antigen binding fragment of the antibody, selected from the group consisting of:
   a) an antibody or antigen binding fragment comprising the amino acid sequence of SEQ ID NO: 28, except that one or more human framework amino acid residues of the antibody or antigen binding fragment are backmutated to one or more corresponding murine framework amino acid residues of SEQ ID No. 2,
   b) an antibody or antigen binding fragment comprising the amino acid sequence of SEQ ID NO: 29, except that one or more human framework amino acid residues of the antibody or antigen binding fragment are backmutated to one or more corresponding murine framework amino acid residues of SEQ ID No. 1, and
   c) an antibody comprising the amino acid sequence of SEQ ID NO: 33 and further comprising the amino acid sequence of SEQ ID NO: 34, except that one or more human framework amino acid residues of the antibody or antigen binding fragment are backmutated to one or more corresponding murine framework amino acid residues of SEQ ID Nos. 1 or 2.

2. An isolated antibody that specifically binds ILT3 or an antigen binding fragment of the antibody, the antibody or antigen binding fragment comprising the amino acid sequence of SEQ ID NO: 28.

3. An isolated antibody that specifically binds ILT3 or an antigen binding fragment of the antibody, the antibody or antigen binding fragment comprising the amino acid sequence of SEQ ID NO: 29.

4. An isolated antibody that specifically binds ILT3 or an antigen binding fragment of the antibody, the antibody or antigen binding fragment comprising a light chain variable region comprising the amino acid sequence of SEQ ID NO:33 and further comprising a heavy chain variable region comprising the amino acid sequence of SEQ ID NO: 34.

5. The isolated antibody or antigen binding fragment thereof, of any one of claims 2, 3 and 4, wherein the isolated antibody or antigen binding fragment downmodulates immune cell activation in vitro.

6. The isolated antibody or antigen binding fragment thereof, of any one of claims 2, 3 and 4, wherein the isolated antibody or antigen binding fragment upmodulates immune response in vivo.

7. The isolated antibody or antigen binding fragment thereof, of any one of claims 2, 3 and 4, wherein the isolated antibody or antigen binding fragment binds to human ILT3 on dendritic cells.

8. The isolated antibody or antigen binding fragment thereof, of any one of claims 2, 3 and 4, wherein the isolated antibody or antigen binding fragment binds to human ILT3 on monocytes.

9. The isolated antibody or antigen binding fragment thereof, of any one of claims 2, 3 and 4, wherein the isolated antibody or antigen binding fragment downmodulates the production of inflammatory cytokines by dendritic cells in vitro.

10. The isolated antibody or antigen binding fragment thereof, of any one of claims 2, 3 and 4, wherein the isolated antibody or antigen binding fragment downmodulates the upregulation of costimulatory molecules on dendritic cells in vitro.

11. The isolated antibody or antigen binding fragment thereof, of any one of claims 2, 3 and 4, wherein the isolated antibody or antigen binding fragment upmodulates the expression of inhibitory receptors on dendritic cells in vitro.

12. A composition comprising the isolated antibody or antigen binding fragment of any one of claims 2, 3 and 4 and a pharmaceutically acceptable carrier.

13. The composition of claim 12, further comprising at least one additional therapeutic agent which upmodulates an immune response in a subject.

14. An isolated antibody that specifically binds ILT3 or an antigen binding fragment of the antibody, the antibody or antigen binding fragment comprising a light chain variable region comprising the amino acid sequence of SEQ ID NO:28 and further comprising a heavy chain variable region comprising the amino acid sequence of SEQ ID NO: 29.

15. The isolated antibody or antigen binding fragment of any one of claims 2, 3, 4, and 14 comprising a heavy chain constant region.

16. The isolated antibody or antigen binding fragment of claim 15, wherein the heavy chain constant region comprises the amino acid sequence of SEQ ID NO: 30.

17. The isolated antibody or antigen binding fragment of claim 15, wherein the heavy chain constant region comprises the amino acid sequence of SEQ ID NO: 31.

18. The isolated antibody or antigen binding fragment of any one of claims 2, 3, 4 and 14 comprising a light chain constant region.

19. The isolated antibody or antigen binding fragment of claim 18, wherein the light chain constant region comprises the amino acid sequence of SEQ ID NO: 32.

20. An isolated antibody that specifically binds ILT3 or an antigen binding fragment of the antibody, the antibody or antigen binding fragment comprising the amino acid sequence of SEQ ID NO: 33.

21. An isolated antibody that specifically binds ILT3 or an antigen binding fragment of the antibody, the antibody or antigen binding fragment comprising the amino acid sequence of SEQ ID NO: 34.

22. An isolated antibody that specifically binds ILT3 or an antigen binding fragment of the antibody, the antibody or antigen binding fragment comprising the amino acid sequence of SEQ ID NO: 35.

23. An isolated antibody that specifically binds ILT3 or an antigen binding fragment of the antibody, the antibody or antigen binding fragment comprising a light chain variable region comprising the amino acid sequence of SEQ ID NO:33 and further comprising a heavy chain variable region comprising the amino acid sequence of SEQ ID NO: 35.

24. The isolated antibody or antigen binding fragment of claim 1, wherein the one or more human framework amino acid residues backmutated to the corresponding murine amino acid residue is selected from the group consisting of amino acid residue number 3, 4, 9, 10, 13, 14, 15, 18, 20, 21, 22, 41, 42, 43, 45, 46, 49, 58, 70, 76, 78, 79, 80, 84, 85, 86, 87, and 100 of SEQ ID NO: 28.

25. The isolated antibody or antigen binding fragment thereof, of any claim 1, wherein the one or more human framework amino acid residues backmutated to the corresponding murine amino acid residue is selected from the group consisting of amino acid residue number 3, 10, 19, 40, 42, 44, 49, 76, 78, 84, 88, 93, and 97 of SEQ ID NO: 29.

26. The isolated antibody or antigen binding fragment of any one of claims 2 3 4, and 14, which is an antigen binding fragment selected from the group consisting of a Fab fragment, a F(ab')2 fragment and a scFv fragment.

27. The isolated antibody or antigen binding fragment of claim 1, wherein amino acid residue number 100 of SEQ ID NO: 28 is backmutated to a corresponding murine framework amino acid residue of SEQ ID No. 2.

28. The isolated antibody or antigen binding fragment of claim 27, wherein amino acid residue number 100 of SEQ ID NO: 28 is backmutated from a glutamine to an alanine.

* * * * *

UNITED STATES PATENT AND TRADEMARK OFFICE
CERTIFICATE OF CORRECTION

PATENT NO. : 7,777,008 B2
APPLICATION NO. : 11/820363
DATED : August 17, 2010
INVENTOR(S) : Paul Ponath, Michael Rosenzweig and Jose F. Ponte It is certified that error appears in the above-identified patent and that said Letters Patent is hereby corrected as shown below:

Column 123: Claim 1, line 21, before "are" delete "or antigen binding fragment".

Column 123: Claim 5, line 39, before "of any" delete "thereof,".

Column 123: Claim 6, line 43, before "of any" delete "thereof,".

Column 123: Claim 6, line 44, after "upmodulates" insert --an--.

Column 123: Claim 7, line 47, before "of any" delete "thereof,".

Column 123: Claim 8, line 51, before "of any" delete "thereof,".

Column 123: Claim 9, line 55, before "of any" delete "thereof,".

Column 123: Claim 10, line 60, before "of any" delete "thereof,".

Column 123: Claim 11, line 65, before "of any" delete "thereof,".

Column 124: Claim 25, line 59, before "of any" delete "thereof,".

Column 124: Claim 25, line 59, before "claim 1" delete "any".

Column 124: Claim 26, line 65, delete "2 3 4," and insert --2, 3, 4,--.

Column 124: Claim 26, line 67, delete "F(ab')2" and insert --F(ab')$_2$--.

Signed and Sealed this

Seventh Day of December, 2010

David J. Kappos
*Director of the United States Patent and Trademark Office*

SEQUENCE LISTING

```
<160> NUMBER OF SEQ ID NOS: 64

<210> SEQ ID NO 1
<211> LENGTH: 135
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 1

Met Glu Phe Gly Leu Ser Leu Val Phe Leu Val Leu Ile Leu Lys Gly
 1               5                  10                  15

Val Gln Cys Glu Val Lys Leu Val Glu Ser Gly Gly Asp Leu Val Lys
             20                  25                  30

Pro Gly Gly Ser Leu Lys Leu Ser Cys Ala Ala Ser Gly Phe Ala Phe
         35                  40                  45

Ser Ser Tyr Asp Met Ser Trp Val Arg Gln Thr Pro Glu Lys Arg Leu
     50                  55                  60

Glu Trp Val Ala Thr Ile Ser Ser Gly Ser Tyr Thr Tyr Tyr Pro
 65                  70                  75                  80

Asp Ser Val Lys Gly Arg Phe Thr Ile Ser Arg Asp Asn Ala Arg Asn
                 85                  90                  95

Thr Leu Tyr Leu Gln Met Ser Ser Leu Arg Ser Glu Asp Thr Ala Leu
            100                 105                 110

Tyr Tyr Cys Glu Arg Leu Trp Gly Ala Met Asp Tyr Trp Gly Gln Gly
        115                 120                 125

Thr Leu Val Thr Val Ser Ser
```

```
<210> SEQ ID NO 2
<211> LENGTH: 127
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 2

Met Glu Thr Asp Thr Ile Leu Leu Trp Val Leu Leu Leu Trp Val Pro
  1               5                  10                  15

Gly Ser Thr Gly Asp Ile Val Leu Thr Gln Ser Pro Ala Thr Leu Ser
             20                  25                  30

Val Thr Pro Gly Asp Ser Val Ser Leu Ser Cys Arg Ala Ser Gln Gly
         35                  40                  45

Leu Thr Asn Asp Leu His Trp Tyr Gln Gln Lys Pro His Glu Ser Pro
     50                  55                  60

Arg Leu Leu Ile Lys Tyr Ala Ser Gln Ser Ile Ser Gly Ile Pro Ser
 65                  70                  75                  80

Arg Phe Ser Gly Ser Gly Ser Gly Thr Asp Phe Thr Leu Thr Ile Asn
                 85                  90                  95

Ser Val Glu Thr Glu Asp Phe Gly Val Phe Phe Cys Gln Gln Ser Asn
            100                 105                 110

Ser Trp Pro Phe Thr Phe Gly Ala Gly Thr Lys Leu Glu Ile Lys
        115                 120                 125

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Ala Phe Ser Ser Tyr Asp Met Ser
  1               5                  10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Ile Ser Ser Ser Gly Ser Tyr Thr Tyr Tyr Pro Asp Ser Val Lys
  1               5                  10                  15

Gly

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Trp Gly Ala Met Asp Tyr
```

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Gly Leu Thr Asn Asp Leu His
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ala Ser Gln Ser Ile Ser
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Ser Asn Ser Trp Pro Phe Thr
 1               5

<210> SEQ ID NO 9
<211> LENGTH: 405
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 9
atggagttcg ggttaagctt ggttttcctt gtcctaattt taaaaggtgt ccagtgtgaa      60
gtgaagctgg tggagtctgg gggagactta gtgaagcctg ggggtccct gaaactctcc      120 tgtgcagcct ctggattcgc tttcagtagc tatgacatgt cttgggttcg ccagactccg      180
gagaagaggc tggaatgggt cgcaaccatt agtagtagtg gtagttacac ctactaccca      240
gacagtgtga aggccgatt caccatctcc agagacaatg ccaggaacac cctgtacctg      300
caaatgagca gtctgaggtc tgaggacacg gccttgtatt actgtgaaag actatggggg      360
gctatggact actggggcca aggacacta gtcacagtct cctca                      405

<210> SEQ ID NO 10
<211> LENGTH: 383
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 10

```
atggagacag acacaatcct gctatgggtg ctgctgctct gggttccagg ctccaccggt      60
gacatcgtgc tgacccagtc tccagccacc ctgtctgtga ctccaggaga tagcgtcagt     120
ctttcctgca gggccagcca aggtcttacc aacgacctac actggtatca acaaaaacca     180
catgagtctc caaggcttct catcaagtat gcttcccagt ccatctctgg gatcccctcc     240
aggttcagtg gcagtggatc agggacagat ttcactctca ctatcaacag tgtggagact     300
gaagattttg gagtgttttt ctgtcaacag agtaacagct ggccattcac gttcggagct     360
gggaccaagc tggaaatcaa acg                                             383
```

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
ggattcgctt tcagtagcta tgacatgtct                                       30
```

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
accattagta gtagtggtag ttacacctac tacccagaca gtgtgaaggg c               51
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
ctatggggggg ctatggacta c                                               21
```

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
agggccagcc aaggtcttac caacgaccta cac                                   33
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
tatgcttccc agtccatctc t                                                21
```

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
caacagagta acagctggcc attcacg                                    27

<210> SEQ ID NO 17
<211> LENGTH: 5354
<212> TYPE: DNA
<213> ORGANISM: Homo sapiens

<400> SEQUENCE: 17
atgatcccca ccttcacggc tctgctctgc ctcggtgaga tttaaagagg gggaggggag    60
acccgagtct tggaggaaat tgcctcaca gccaggccct ggttctttag gagactcaaa    120
aatctcaggg tagccgggcg cggtggctca cgcctgtaat cccagcactt tgggaggccg    180
aggcgggcgg atcacgaggt caggagatcg agaccatcct ggctaacacg gtgaaaccct    240
gtctctacta aaaatacaaa aaattagccg gggtggttg caggcgcctg tggtcccagc    300
cactcgggag gctgaggcag gagaatggcg tgaacccggg aggcggagct gcagtgagc    360 caagatcgca ccaccgcact ccagcctggg tgacagcgag actccgtctc aaaaaaaaaa    420 aaaaaaaaa aaaaaaaaa atctcagggt aaaaaaagga cctgctcagg cttccggggc    480
aaatccctca cagggaactc tcttccaggg ctgagtctgg gccccaggac ccacatgcag    540
gcaggtgatt ctgtccccag ctgtcccagg tccctcctcc tcactgggac aaggggccac    600
ccatgggcag ctggggagg agacagcagt tctgggtgac tgatgaggat gacgggggg    660 tcctggggct gagagctggg atctgagggc tgaggaaggt cttgggatcc agcctctgat    720
tttcttccag gccccctccc caaacccacc ctctgggctg agccaggctc tgtgatcagc    780 tggggaact ctgtgaccat ctggtgtcag gggaccctgg aggctcggga gtaccgtctg    840
gataaagagg aaagcccagc accctgggac agacagaacc cactggagcc caagaacaag    900
gccagattct ccatcccatc catgacagag gactatgcag ggagataccg ctgttactat    960
cgcagccctg taggctggtc acagcccagt gaccccctgg agctggtgat gacaggtgag    1020
aggacactca ggggtcccag ccccaggctc tgccctcagg aagggggtca gctctcaggg    1080
gcatctccct ctcacagccc agccctgggg atgatgtggg aggtgggagc cccatttaac    1140
acggtgcctc cttctctcct aggagcctac agtaaaccca ccctttcagc cctgccgagt    1200
cctcttgtga cctcaggaaa gagcgtgacc ctgctgtgtc agtcacggag cccaatggac    1260
actttccttc tgatcaagga gcgggcagcc catccctac tgcatctgag atcagagcac    1320
ggagctcagc agcaccaggc tgaattcccc atgagtcctg tgacctcagt gcacgggggg    1380
acctacaggt gcttcagctc acacggcttc tcccactacc tgctgtcaca ccccagtgac    1440
cccctggagc tcatagtctc aggtgaggct cctgaccctg tcctctctga gtcagtggc    1500 tccgttcatg ccctgctgcc aggagagctc tgggcaggga tggagggaga ggggctcagc    1560
cagtggggga ctcagccctc agagggagg aggacaacag gggccctccc aggcatgccc    1620
atgctcttct ccctcaccta gggtccagaa ggtgccaggt ggacagagaa atggtccttg    1680
ggaagctgca gggcagatat agggagaggt tcaatttgat gtggagaccc aagggcaacc    1740

```
ccagactctc accctcctct tgtccttcta cccaggatcc ttggagggtc ccaggccctc   1800
acccacaagg tccgtctcaa cagctggtga gtctcagagg cctctgtcca gagagtttcc   1860
aaagcccgag gcctgtctca agacatgctc agtggatcta agtcctcgtt ccaattctca   1920
gctgggcttg cttccacggg tgtgggagtc gggcagcgac ttgggaggca ccacaggctc   1980
ccaaggccct gaggctgggc tggtgagggg tgaggggtc aaggctgaag gagatgttgc   2040
ggggagaaac cgacctgatg cggggagcag ggcagcccca gccctcacat ccctgttcta   2100
acccagcagg ccctgaggac cagcccctca tgcctacagg gtcagtcccc cacagtggtg   2160 agtgagggc tctgagtggg aggtgggcag ggtctagggg agccaagggt gggttctgtc     2220
ctaggttcag gctcctctgg aggtggtgat gtggacaggc ccctcccctg catgggcctc   2280
agtttctcca agtgtaaagg agagaggcct gtgggtggga aagttccttt cagctctgac   2340
tcccagctgt gccctcctgg gagaggaggc ctcccaggga acctcccaga cccgattccg   2400
caggggcctg tccggtccca cctgcagcag agacggtgac ctggggcagg ggaggggagc   2460
agggcggtgg ttcaagacag tcaggctctt ccctgcaac tctggggctt ggctctggtg     2520
caggaacaag ggctgcagct cagactcccg ggtttccttc ccagctctgc cgcttcctgg   2580
ctggaggggt ctgggcagg cgattcccct ctctgagcct cagtttgtgc atctgtgaaa     2640
tgggtggaga gagggtggca atctcaggtt gcacaactgc tgtgagggtt ggaggtaatg   2700
aaagaaagac ccagcacaca cagtaggtgc acacacagta ggtgtgcaca tcaatgacat   2760
catccccatt cctgatgtca tcacgcccaa ggtctgagaa ggcactggga ggtactgatc   2820
ggggtcttgg tggtctccat cctgcttctc tccctcctcc tcttcctcct cctccaacac   2880
tggcgtcagg aaaacacag acattgggt aagtaggaaa ttgggggacc cgtgggctga     2940
tggagggtgg gctcagggca ccagccaaag ggactccaga taggagaggt catcttagaa   3000
actctgctcc agaaattccc agtgagaaaa tctagaaaga agaaaatgaa tgagggagta   3060
atggaagtgc tttattcttt cggttttct aaacttagaa agtatttaaa acatccttgc     3120
aagtgtattt tcaggtttcc tttcctcttg acttgcatgt gcaaggcagg tggttctaac   3180
gttcccagag ctgagactct gtccatcttc ccccagccca gagacaggct gatttccaac   3240
gtcctccagg ggctgccgag ccagagccca aggacggggg cctacagagg aggtaattct   3300
gcccaaagac ctcagactcc cacccatccc aacagccacc tcactgtccc cttacactcc   3360
cgtatcctcc cccaggtcca gcccagctgc tgacgtccag ggagaaaact tctgtgagtg   3420
agaggcagag aaggtgcacc tggggtggag ctgggggtcc caaaatttca atagcaatgg   3480
gggcaggagc acaggctagg attggtcagg gactcaggga gaagtggtct gaacccacat   3540
tgtgggacct cggggacatc gcagcccctc cctgcgttgc agtggcacta atgggaacag   3600
ggcagggacc agcaggaatg agaggtccca gggaaccttc ccaggagatg aaccccttgc   3660
tctactccag caggtgctgc cgtgaagaac acacagcctg aggacggggt ggaaatggac   3720
actcgggtga gaacccgccc ctgtcccag caccaaaggc ctcctggtgc cagatctaat     3780
cctgcaggac ttctctgtcc tccttccccc ggctctcagc atcgtcacgg tggaccctc     3840 cttgtccagc acgctgcctc ctgcctgctg ggacctcact ctctcctgct gtcctgggac   3900
ctcatgggcc tcctcccggg tcccttcct gctcctcatc ctctgtttgg ccatctggtt     3960
gttagagagc tccccaggcc tcaggaggat gacgaataaa tgaaccactc cagtcccctg   4020
ggctcccctt cattcattca tctagtgagt gttcccaggg agctcactgt ggatggggct   4080
```

-continued

```
cccatggga gctgcagaca cagcagggag caaagccgcc cccgcctcct gagctcacct    4140
cgtggtggga gacaaaatgc aaataaatgc atcgtgtcca ggagtgcaac gtgctgtaag    4200
gaacataaac caggtaaagg gcagagagtg tggggcagtg gggccagtct gaatggaaag    4260
ggagggctgt ctgctcagct gtcatctgag aagcctggac ggagagggcc acgtgatcct    4320
ctaatggacg agcccctgca ggcagaggaa acagccgtgc aaaggccccg aggcagcagc    4380
gagctcttgc aggaaggccg cgtgaggctg cagccaaatg gcaaggtca gagtgaggag    4440 cagagaccag aaccacaggg agggagcggc cagaccctcc acggccttag ggcatccctg    4500
agattccgtc aggaaaggga tgtaatcgga tcaccctggg aacagtgggg aaaattgact    4560
ccagggagtc aggaggattc aaggacaccc ccaccactg tctctctcca gcagagccca    4620
cacgatgaag accccaggc agtgacgtat gccgaggtga acactccag acctaggaga    4680 gaaatggcct ctcctccctc ccactgtct ggggaattcc tggacacaaa ggacagacag    4740
gcagaagagg acagacagat ggacactgag gtgagtcctt cctctccag gcccccaggc    4800 ctcccccacc cccaccacgt tccttccctc tcactctccc ccgctgcagg ctgctgcatc    4860
tgaagccccc caggatgtga cctacgccca gctgcacagc tttaccctca gacagaaggc    4920
aactgagcct cctccatccc aggaaggggc ctctccagct gagcccagtg tctatgccac    4980
tctggccatc cactaatcca gggggaccc agacccaca agccatggag actcaggacc    5040
ccagaaggca tggaagctgc ctccagtaga catcactgaa ccccagccag cccagacccc    5100
tgacacagac cactagaaga ttccgggaac gttgggagtc acctgattct gcaaagataa    5160
ataatatccc tgcattatca aaataaagta gcagacctct caattcacaa tgagttaact    5220
gataaaacaa aacagaagtc agacaatgtt ttaaattgaa tgatcatgta aatattacac    5280
atcaaaccaa tgacatggga aaatgggagc ttctatgcag gcaggacaaa aaatagaggg    5340
ggatccacta gttc                                                      5354
```

<210> SEQ ID NO 18
<211> LENGTH: 434
<212> TYPE: PRT
<213> ORGANISM: Homo sapiens

<400> SEQUENCE: 18

```
Met Ile Pro Thr Phe Thr Ala Leu Leu Cys Leu Gly Leu Ser Leu Gly
  1               5                  10                  15

Pro Arg Thr His Met Gln Ala Gly Pro Leu Pro Lys Pro Thr Leu Trp
             20                  25                  30

Ala Glu Pro Gly Ser Val Ile Ser Trp Gly Asn Ser Val Thr Ile Trp
         35                  40                  45

Cys Gln Gly Thr Leu Glu Ala Arg Glu Tyr Arg Leu Asp Lys Glu Glu
     50                  55                  60

Ser Pro Ala Pro Trp Asp Arg Gln Asn Pro Leu Glu Pro Lys Asn Lys
 65                  70                  75                  80

Ala Arg Phe Ser Ile Pro Ser Met Thr Glu Asp Tyr Ala Gly Arg Tyr
                 85                  90                  95

Arg Cys Tyr Tyr Arg Ser Pro Val Gly Trp Ser Gln Pro Ser Asp Pro
            100                 105                 110

Leu Glu Leu Val Met Thr Gly Ala Tyr Ser Lys Pro Thr Leu Ser Ala
        115                 120                 125

Leu Pro Ser Pro Leu Val Thr Ser Gly Lys Ser Val Thr Leu Leu Cys
    130                 135                 140
```

```
Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
            165                 170                 175

Gln Ala Glu Phe Pro Met Ser Pro Val Thr Ser Val His Gly Gly Thr
        180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Gly Pro
210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
            245                 250                 255

His Trp Glu Val Leu Ile Gly Val Leu Val Val Ser Ile Leu Leu Leu
        260                 265                 270

Ser Leu Leu Leu Phe Leu Leu Leu Gln His Trp Arg Gln Gly Lys His
        275                 280                 285

Arg Thr Leu Ala Gln Arg Gln Ala Asp Phe Gln Arg Pro Pro Gly Ala
        290                 295                 300

Ala Glu Pro Glu Pro Lys Asp Gly Gly Leu Gln Arg Arg Ser Ser Pro
305                 310                 315                 320

Ala Ala Asp Val Gln Gly Glu Asn Phe Cys Ala Ala Val Lys Asn Thr
                325                 330                 335

Gln Pro Glu Asp Gly Val Glu Met Asp Thr Arg Gln Ser Pro His Asp
            340                 345                 350

Glu Asp Pro Gln Ala Val Thr Tyr Ala Glu Val Lys His Ser Arg Pro
        355                 360                 365

Arg Arg Glu Met Ala Ser Pro Pro Ser Pro Leu Ser Gly Glu Phe Leu
        370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Gln Leu His
                405                 410                 415

Ser Phe Thr Leu Arg Gln Lys Ala Thr Glu Pro Pro Pro Ser Gln Glu
            420                 425                 430

Gly Ala

<210> SEQ ID NO 19
<211> LENGTH: 10
<212> TYPE: PRT
<213> ORGANISM: Homo sapiens

<400> SEQUENCE: 19

Gly Gln Gly Thr Lys Leu Glu Ile Lys Arg
 1               5                  10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 20

Gly Gly Gly Gly Ser Gly Gly Gly Gly Ser Gly Gly Gly Gly Ser
```

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Met Glu Thr Asp Thr Ile Leu Leu Trp Val Leu Leu Leu Trp Val Pro
1               5                   10                  15

Gly Ser Thr Gly
            20

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Met Glu Phe Gly Leu Ser Leu Val Phe Leu Val Leu Ile Leu Lys Gly
1               5                   10                  15

Val Gln Cys

<210> SEQ ID NO 23
<211> LENGTH: 105
<212> TYPE: PRT
<213> ORGANISM: Mus musculus

<400> SEQUENCE: 23

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu
            100                 105

<210> SEQ ID NO 24
<211> LENGTH: 334
<212> TYPE: PRT
<213> ORGANISM: Mus musculus

<400> SEQUENCE: 24

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser

```
                35                  40                  45
Ser Val His Thr Phe Pro Ala Leu Leu Gln Ser Gly Leu Tyr Thr Met
 50                  55                  60

Ser Ser Ser Val Thr Val Pro Ser Ser Thr Trp Pro Ser Gln Thr Val
 65                  70                  75                  80

Thr Cys Ser Val Ala His Pro Ala Ser Ser Thr Val Asp Lys Lys
                     85                  90                  95

Leu Glu Pro Ser Gly Pro Ile Ser Thr Ile Asn Pro Cys Pro Pro Cys
                100                 105                 110

Lys Glu Cys Lys Cys Pro Ala Pro Asn Leu Glu Gly Gly Pro Ser Val
                115                 120                 125

Phe Ile Phe Pro Pro Asn Ile Lys Asp Val Leu Met Ile Ser Leu Thr
        130                 135                 140

Pro Lys Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Ile Arg Val Val Ser
                180                 185                 190

Thr Leu Pro Ile Gln His Gln Asp Trp Met Ser Gly Lys Glu Phe Lys
        195                 200                 205

Cys Lys Val Asn Asn Lys Asp Leu Pro Ser Pro Ile Glu Arg Thr Ile
        210                 215                 220

Ser Lys Ile Lys Gly Leu Val Arg Ala Gln Val Tyr Ile Leu Pro Pro
225                 230                 235                 240

Pro Ala Glu Gln Leu Ser Arg Lys Asp Val Ser Leu Thr Cys Leu Val
                245                 250                 255

Val Gly Phe Asn Pro Gly Asp Ile Ser Val Glu Trp Thr Ser Asn Gly
                260                 265                 270

His Thr Glu Glu Asn Tyr Lys Asp Thr Ala Pro Val Leu Asp Ser Asp
                275                 280                 285

Gly Ser Tyr Phe Ile Tyr Ser Lys Leu Asn Met Lys Thr Ser Lys Trp
        290                 295                 300

Glu Lys Thr Asp Ser Phe Ser Cys Asn Val Arg His Glu Gly Leu Lys
305                 310                 315                 320

Asn Tyr Tyr Leu Lys Lys Thr Ile Ser Arg Ser Pro Gly Lys
                325                 330

<210> SEQ ID NO 25
<211> LENGTH: 214
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 25

Asp Ile Val Leu Thr Gln Ser Pro Ala Thr Leu Ser Val Thr Pro Gly
 1                   5                  10                  15

Asp Ser Val Ser Leu Ser Cys Arg Ala Ser Gln Gly Leu Thr Asn Asp
                 20                  25                  30

Leu His Trp Tyr Gln Gln Lys Pro His Glu Ser Pro Arg Leu Leu Ile
             35                  40                  45

Lys Tyr Ala Ser Gln Ser Ile Ser Gly Ile Pro Ser Arg Phe Ser Gly
     50                  55                  60
```

-continued

```
Ser Gly Ser Gly Thr Asp Phe Thr Leu Thr Ile Asn Ser Val Glu Thr
 65                  70                  75                  80

Glu Asp Phe Gly Val Phe Phe Cys Gln Gln Ser Asn Ser Trp Pro Phe
                 85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 446
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 26

Glu Val Lys Leu Val Glu Ser Gly Gly Asp Leu Val Lys Pro Gly Gly
  1               5                  10                  15

Ser Leu Lys Leu Ser Cys Ala Ala Ser Gly Phe Ala Phe Ser Ser Tyr
             20                  25                  30

Asp Met Ser Trp Val Arg Gln Thr Pro Glu Lys Arg Leu Glu Trp Val
         35                  40                  45

Ala Thr Ile Ser Ser Ser Gly Ser Tyr Thr Tyr Tyr Pro Asp Ser Val
     50                  55                  60

Lys Gly Arg Phe Thr Ile Ser Arg Asp Asn Ala Arg Asn Thr Leu Tyr
 65                  70                  75                  80

Leu Gln Met Ser Ser Leu Arg Ser Glu Asp Thr Ala Leu Tyr Tyr Cys
                 85                  90                  95

Glu Arg Leu Trp Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 27
<211> LENGTH: 446
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 27

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ser Ser Ser Gly Ser Tyr Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Glu Arg Leu Trp Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala

```
            115                 120                 125
Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 28

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Leu Thr Asn Asp
             20                  25                  30
```

```
Leu His Trp Tyr Gln Gln Lys Pro Gly Lys Ala Pro Lys Arg Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Phe
                85                  90                  95

Thr Phe Gly Gln Gly Thr Lys Leu Glu Ile Lys
            100                 105

<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Ser Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Trp Gly Ala Met Asp Tyr Trp Gly Gln Gly Thr Leu Val
            100                 105                 110

Thr Val Ser Ser
        115

<210> SEQ ID NO 30
<211> LENGTH: 330
<212> TYPE: PRT
<213> ORGANISM: Homo sapiens

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 31
<211> LENGTH: 330
<212> TYPE: PRT
<213> ORGANISM: Homo sapiens

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Ala Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 32
<211> LENGTH: 107
<212> TYPE: PRT
<213> ORGANISM: Homo sapiens

<400> SEQUENCE: 32

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 33
<211> LENGTH: 214
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 33

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Leu Thr Asn Asp
            20                  25                  30
```

Leu His Trp Tyr Gln Gln Lys Pro Gly Lys Ala Pro Lys Arg Leu Ile
            35                  40                  45

Tyr Tyr Ala Ser Gln Ser Ile Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 446
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Ser Ser Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Trp Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser

```
                  165                 170                 175
Gly Leu Tyr Ser Leu Ser Ser Val Val Thr Val Pro Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 35
<211> LENGTH: 446
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 35

Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Ala Phe Ser Ser Tyr
                20                  25                  30
Asp Met Ser Trp Val Arg Gln Ala Pro Gly Lys Gly Leu Glu Trp Val
            35                  40                  45
Ser Thr Ile Ser Ser Ser Gly Ser Tyr Thr Tyr Tyr Pro Asp Ser Val
        50                  55                  60
Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                 85                  90                  95

Ala Arg Leu Trp Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 36
<211> LENGTH: 95
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
  1               5                  10                  15
```

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 37
<211> LENGTH: 95
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Asn Ser Tyr Pro
                85                  90                  95

<210> SEQ ID NO 38
<211> LENGTH: 95
<212> TYPE: PRT
<213> ORGANISM: Homo sapiens

<400> SEQUENCE: 38

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95

<210> SEQ ID NO 39
<211> LENGTH: 95
<212> TYPE: PRT
<213> ORGANISM: Homo sapiens

<400> SEQUENCE: 39

Asp Ile Gln Leu Thr Gln Ser Pro Ser Phe Leu Ser Ala Ser Val Gly
1               5                   10                  15
```

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

<210> SEQ ID NO 40
<211> LENGTH: 95
<212> TYPE: PRT
<213> ORGANISM: Homo sapiens

<400> SEQUENCE: 40

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 41
<211> LENGTH: 95
<212> TYPE: PRT
<213> ORGANISM: Homo sapiens

<400> SEQUENCE: 41

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 42
<211> LENGTH: 95
<212> TYPE: PRT
<213> ORGANISM: Homo sapiens

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp

-continued

```
                    20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 43
<211> LENGTH: 95
<212> TYPE: PRT
<213> ORGANISM: Homo sapiens

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Gly Ile Ser Ser Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 44
<211> LENGTH: 95
<212> TYPE: PRT
<213> ORGANISM: Homo sapiens

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 45
<211> LENGTH: 95
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 46
<211> LENGTH: 95
<212> TYPE: PRT
<213> ORGANISM: Homo sapiens

<400> SEQUENCE: 46

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Gly Tyr Ser Thr Pro
                85                  90                  95
```

<210> SEQ ID NO 47
<211> LENGTH: 95
<212> TYPE: PRT
<213> ORGANISM: Homo sapiens

<400> SEQUENCE: 47

```
Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
            35                  40                  45

Tyr Tyr Ala Ser Ser Leu Gln Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95
```

<210> SEQ ID NO 48
<211> LENGTH: 98
<212> TYPE: PRT
<213> ORGANISM: Homo sapiens

<400> SEQUENCE: 48

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

```
Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 49
<211> LENGTH: 98
<212> TYPE: PRT
<213> ORGANISM: Homo sapiens

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 50
<211> LENGTH: 98
<212> TYPE: PRT
<213> ORGANISM: Homo sapiens

<400> SEQUENCE: 50

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 51
<211> LENGTH: 98
<212> TYPE: PRT
<213> ORGANISM: Homo sapiens

<400> SEQUENCE: 51

Gln Val Gln Leu Leu Glu Ser Gly Gly Gly Leu Val Lys Pro Gly Gly
```

-continued

```
                1               5                  10                 15
Ser Leu Arg Leu Ser Cys Ala Ala Ser Gly Phe Thr Phe Ser Asp Tyr
            20                  25                 30

Tyr Met Ser Trp Ile Arg Gln Ala Pro Gly Lys Gly Leu Glu Trp Val
            35                  40                 45

Ser Tyr Ile Ser Ser Ser Ser Tyr Thr Asn Tyr Ala Asp Ser Val
            50              55                 60

Lys Gly Arg Phe Thr Ile Ser Arg Asp Asn Ala Lys Asn Ser Leu Tyr
 65                     70              75                  80

Leu Gln Met Asn Ser Leu Arg Ala Glu Asp Thr Ala Val Tyr Tyr Cys
                85                  90                 95

Ala Arg

<210> SEQ ID NO 52
<211> LENGTH: 98
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Ser Ser Tyr
            20                  25                 30

Ala Met Ser Trp Val Arg Gln Ala Pro Gly Lys Gly Leu Glu Trp Val
            35                  40                 45

Ser Ala Ile Ser Gly Ser Gly Gly Ser Thr Tyr Tyr Ala Asp Ser Val
            50              55                 60

Lys Gly Arg Phe Thr Ile Ser Arg Asp Asn Ser Lys Asn Thr Leu Tyr
 65                     70              75                  80

Leu Gln Met Asn Ser Leu Arg Ala Glu Asp Thr Ala Val Tyr Tyr Cys
                85                  90                 95

Ala Lys

<210> SEQ ID NO 53
<211> LENGTH: 98
<212> TYPE: PRT
<213> ORGANISM: Homo sapiens

<400> SEQUENCE: 53

Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Ser Ser Tyr
            20                  25                 30

Ala Met Ser Trp Val Arg Gln Ala Pro Gly Lys Gly Leu Glu Trp Val
            35                  40                 45

Ser Ala Ile Ser Gly Ser Gly Gly Ser Thr Tyr Tyr Gly Asp Ser Val
            50              55                 60

Lys Gly Arg Phe Thr Ile Ser Arg Asp Asn Ser Lys Asn Thr Leu Tyr
 65                     70              75                  80

Leu Gln Met Asn Ser Leu Arg Ala Glu Asp Thr Ala Val Tyr Tyr Cys
                85                  90                 95

Ala Lys

<210> SEQ ID NO 54
<211> LENGTH: 98
<212> TYPE: PRT
```

<213> ORGANISM: Homo sapiens

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 55
<211> LENGTH: 98
<212> TYPE: PRT
<213> ORGANISM: Homo sapiens

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 56
<211> LENGTH: 98
<212> TYPE: PRT
<213> ORGANISM: Homo sapiens

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 57
<211> LENGTH: 98
<212> TYPE: PRT
<213> ORGANISM: Homo sapiens

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 58
<211> LENGTH: 98
<212> TYPE: PRT
<213> ORGANISM: Homo sapiens

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg
```

<210> SEQ ID NO 59
<211> LENGTH: 98
<212> TYPE: PRT
<213> ORGANISM: Homo sapiens

<400> SEQUENCE: 59

```
Glu Val Gln Leu Val Glu Ser Gly Glu Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Gly Ser Leu Arg Ala Glu Asp Met Ala Val Tyr Tyr Cys
                85                  90                  95

Ala Arg

<210> SEQ ID NO 60
<211> LENGTH: 98
<212> TYPE: PRT
<213> ORGANISM: Homo sapiens

<400> SEQUENCE: 60

Glu Val Gln Leu Val Glu Ser Gly Gly Gly Leu Val Gln Pro Gly Gly
  1               5                  10                  15

Ser Leu Arg Leu Ser Cys Ser Ala Ser Gly Phe Thr Phe Ser Ser Tyr
             20                  25                  30

Ala Met His Trp Val Arg Gln Ala Pro Gly Lys Gly Leu Glu Tyr Val
         35                  40                  45

Ser Ala Ile Ser Ser Asn Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Val Gln Met Ser Ser Leu Arg Ala Glu Asp Thr Ala Val Tyr Tyr Cys
                85                  90                  95

Val Lys

<210> SEQ ID NO 61
<211> LENGTH: 98
<212> TYPE: PRT
<213> ORGANISM: Homo sapiens

<400> SEQUENCE: 61

Gln Val Gln Leu Val Glu Ser Gly Gly Gly Leu Val Gln Pro Gly Gly
  1               5                  10                  15

Ser Leu Arg Leu Ser Cys Ser Ala Ser Gly Phe Thr Phe Ser Ser Tyr
             20                  25                  30

Ala Met His Trp Val Arg Gln Ala Pro Gly Lys Gly Leu Glu Tyr Val
         35                  40                  45

Ser Ala Ile Ser Ser Asn Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 62
<211> LENGTH: 98
<212> TYPE: PRT
<213> ORGANISM: Homo sapiens

<400> SEQUENCE: 62

Glu Val Gln Leu Val Glu Ser Gly Gly Gly Leu Val Gln Pro Gly Gly
  1               5                  10                  15

Ser Leu Arg Leu Ser Cys Ser Ala Ser Gly Phe Thr Phe Ser Ser Tyr
             20                  25                  30

Ala Met His Trp Val Arg Gln Ala Pro Gly Lys Gly Leu Glu Tyr Val
         35                  40                  45
```

```
Ser Ala Ile Ser Ser Asn Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Val Gln Met Ser Ser Leu Arg Ala Glu Asp Thr Ala Val Tyr Tyr Cys
                85                  90                  95

Val Lys

<210> SEQ ID NO 63
<211> LENGTH: 116
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 63

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Ala Phe Ser Ser Tyr
                20                  25                  30

Asp Met Ser Trp Val Arg Gln Ala Pro Gly Lys Gly Leu Glu Trp Val
            35                  40                  45

Ser Thr Ile Ser Ser Gly Ser Tyr Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Leu Trp Gly Ala Met Asp Tyr Trp Gly Gln Gly Thr Leu Val
            100                 105                 110

Thr Val Ser Ser
        115

<210> SEQ ID NO 64
<211> LENGTH: 108
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 64

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Leu Thr Asn Asp
                20                  25                  30

Leu His Trp Tyr Gln Gln Lys Pro Gly Lys Ala Pro Lys Arg Leu Ile
            35                  40                  45

Tyr Tyr Ala Ser Gln Ser Ile Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Ser Asn Ser Trp Pro Phe
                85                  90                  95

Thr Phe Gly Gln Gly Thr Lys Leu Glu Ile Lys Arg
            100                 105
```